US009410205B2

(12) United States Patent
Bogunovic et al.

(10) Patent No.: US 9,410,205 B2
(45) Date of Patent: Aug. 9, 2016

(54) METHODS FOR PREDICTING SURVIVAL IN METASTATIC MELANOMA PATIENTS

(75) Inventors: Dusan Bogunovic, New York, NY (US); Nina Bhardwaj, West Orange, NJ (US); David O'Neill, New York, NY (US)

(73) Assignee: New York University, New York, NY (US)

( * ) Notice: Subject to any disclaimer, the term of this patent is extended or adjusted under 35 U.S.C. 154(b) by 603 days.

(21) Appl. No.: 12/932,068

(22) Filed: Feb. 17, 2011

(65) Prior Publication Data

US 2011/0275089 A1     Nov. 10, 2011

Related U.S. Application Data

(60) Provisional application No. 61/305,870, filed on Feb. 18, 2010.

(51) Int. Cl.
*G01N 33/574*     (2006.01)
*C12Q 1/68*       (2006.01)

(52) U.S. Cl.
CPC .......... *C12Q 1/6886* (2013.01); *G01N 33/5743* (2013.01); *C12Q 2600/106* (2013.01); *C12Q 2600/118* (2013.01); *C12Q 2600/158* (2013.01); *G01N 2800/52* (2013.01)

(58) Field of Classification Search
USPC ................................................ 435/7.23, 6.14
See application file for complete search history.

(56) References Cited

U.S. PATENT DOCUMENTS

| 7,615,349 B2 | 11/2009 | Riker et al. |
| 2008/0113360 A1 | 5/2008 | Riker et al. |
| 2008/0118462 A1 | 5/2008 | Alani et al. |
| 2010/0076691 A1 | 3/2010 | Palucka et al. |

OTHER PUBLICATIONS

Niezabitowski et al. (Journal of Surgical Oncology 1999, 70:150-160).*
Fecher et al., "Toward a molecular classification of melanoma", J Clin Oncol, 2007, vol. 25, pp. 1606-1620.
Balch et al., "Predicting outcomes in metastatic melanoma", J Clin Oncol, 2008, vol. 26, pp. 168-169.
Haqq et al., "The gene expression signatures of melanoma progression", Proc Natl Acad Sci USA, 2005, vol. 102, pp. 6092-6097.
Jaeger et al., "Gene expression signatures for tumor progression, tumor subtype, and tumor thickness in laser-microdissected melanoma tissues", Clin Cancer Res, 2007, vol. 13, pp. 806-815.
John et al., "Predicting clinical outcome through molecular profiling in stage III melanoma", Clin Cancer Res, 2008, vol. 14, pp. 5173-5180.
Piras et al., "The predictive value of CD8, CD4, CD68, and human leukocyte antigen-D-related cells in the prognosis of cutaneous malignant melanoma with vertical growth phase", Cancer, 2005, vol. 104, pp. 1246-1254.

Sato et al., "Intraepithelial CD8+ tumor-infiltrating lymphocytes and a high CD8+/regulatory T cell ratio are associated with favorable prognosis in ovarian cancer", Proc Natl Acad Sci USA, 2005, vol. 102, pp. 18538-18543.
Galon et al., "Type, density, and location of immune cells within human colorectal tumors predict clinical outcome", Science, 2006, vol. 313, pp. 1960-1964.
Clemente et al., "Prognostic value of tumor infiltrating lymphocytes in the vertical growth phase of primary cutaneous melanoma", Cancer, 1996, vol. 77, pp. 1303-1310.
Mihm et al., "Tumor infiltrating lymphocytes in lymph node melanoma metastases: A histopathologic prognostic indicator and an expression of local immune response", Lab Invest, 1996, vol. 74, pp. 43-47.
Dave et al., "Prediction of survival in follicular lymphoma based on molecular features of tumor-infiltrating immune cells", N Engl J Med, 2004, vol. 351, pp. 2159-2169.
Attis et al., "Mitotic rate in melanoma: A reexamination", Am J Clin Pathol, 2007, vol. 127, pp. 380-384.
Francken et al., "The prognostic importance of tumor mitotic rate confirmed in 1317 patients with primary cutaneous melanoma and long follow-up", Ann Surg Oncol, 2004, vol. 11, pp. 426-433.
Liu et al., "Correlation of subjective self-reported melanoma growth rate with objective tumor proliferation markers", Arch Dermatol, 2008, vol. 144, pp. 555-556.
Reddy et al., "Cell proliferation markers in predicting metastases in malignant melanoma", 1995, J Cutan Pathol, vol. 22, pp. 248-251.
Agarwala, "Current systemic therapy for metastatic melanoma", Expert Rev Anticancer Therapy, 2009, vol. 9, pp. 1-18.
Yang et al., "The history and future of chemotherapy for melanoma", Hematol Oncol Clin N Am, 2009, vol. 23, pp. 583-597.
Bhatia et al., "Treatment of metastatic melanoma: An overview", Oncology, 2009, vol. 23, pp. 488-496.
Mouawad et al., "Treatment for metastatic malignant melanoma: Old drugs and new strategies", Critical Reviews in Oncology/Hematology, 2010, vol. 74, pp. 27-29.
Bhardwaj et al., "TLR Agonists: Are they good adjuvants?", Cancer J, 2010, vol. 16, pp. 382-391.
Rosenberg et al., "Adoptive cell therapy for the treatment of patients with metastatic melanoma", Curr Opin Immunol, 2009, vol. 21, pp. 233-240.

(Continued)

*Primary Examiner* — Yan Xiao
(74) *Attorney, Agent, or Firm* — Klauber & Jackson LLC

(57) ABSTRACT

Cellular and genetic signatures and methods of using same for subcategorizing stage III melanoma tumors are described herein. The signatures and methods are particularly useful with regard to establishing more distinct criteria on which basis to differentiate stage IIIB and IIIC melanoma patients. Assessment of the cellular and genetic signatures of a melanoma sample using methods described herein yields information on which basis differential survival duration and sensitivity to various cancer therapies can be predicted for a Stage IIIB or Stage IIIC melanoma patients. As described herein, gene expression profiling, determination of mitotic index (MI), and quantification of tumor infiltrating leukocytes (TILs) and CD3+ cells in metastatic lesions may be utilized to predict or assess drug response, drug sensitivity, and clinical outcome in metastatic melanoma patients.

23 Claims, 46 Drawing Sheets

(56) References Cited

OTHER PUBLICATIONS

Jager et al., "Recombinant vaccinia/fowlpox NY-ESO-1 vaccines induce both humoral and cellular NY-ESO-1- specific immune responses in cancer patients", Proc Natl Acad Sci USA, 2006, vol. 103, p. 14453-14458.

Hunder et al., "Treatment of metastatic melanoma with autologous CD4+ T cells against NY-ESO-1", N Engl J Med, 2008, vol. 358, pp. 2698-2703.

Tsuji et al., "Antibody-targeted NY-ESO-1 to mannose receptor or DEC-205 in vitro elicits dual human CD8+ and CD4+ T cell responses with broad antigen specificity", J Immunol, 2011, vol. 186, pp. 1218-1227.

Robbins et al., "Tumor regression in patients with metastatic synovial cell sarcoma and melanoma using genetically engineered lymhocytes reactive with NY-ESO-1", J Clin Oncol, epub 2011, vol. 28, pp. 1-9.

Crowson et al., "Prognosticators of melanoma, the melanoma report, and the sentinel lymph node", Modern Pathology, 2006, vol. 19, pp. S71-S87.

Bogunovic et al., "Immune profile and mitotic index of metastatic melanoma lesions enhance clinical staging in predicting patient survival", Proc Nat Acad Sci, 2009, vol. 106, vol. 48, pp. 20429-20434.

Murali et al., "Tumor-infiltrating lymphocytes and mitotic index in metastatic melanoma as predictors of patient survival", Proc Nat Acad Sci, 2010, vol. 107, p. E46.

Lyle et al., "TIA-1 positive tumor-infiltrating lymphocytes in nevi and melanomas", Mod Pathol, 2000, vol. 13, pp. 52-55.

Bogunovic et al., "Gene expression profile for metastatic melanoma and patient survival", J Clin Oncol 2008, vol. 26 (May 20 suppl; abstract 9049).

Bogunovic et al., "Use of gene expression profile and mitotic index of metastatic melanoma lesions as an adjunct to TNM staging in predicting patient survival", J Clin Oncol, 2009, vol. 27, p. 15s (Suppl; abstract 9014).

Harlin et al., "Chemokine expression in melanoma metastases associated with CD8 +T-cell recruitment", Cancer Res, 2009, vol. 69, pp. 3077-3085.

Otto et al., "Prognostic classification of malignant melanomas by combining clinical, histological, and immunohistochemical parameters", Oncology, 1999, vol. 56, pp. 208-214.

Gajewski et al., "Gene signature in melanoma associated with clinical activity", The Cancer Journal, 2010, vol. 16, pp. 399-403.

* cited by examiner

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 1 | 236967_at | LOC645249 | hypothetical protein LOC645249 | Hs.224879 | -14.34 | 0.7 | | | |
| 2 | 1568878_at | --- | --- | Hs.531359 | -6.90 | 1.2 | | | |
| 3 | 205113_at | NEFM | neurofilament, medium polypeptide 150kDa | Hs.458657 | -4.20 | 2.8 | | | |
| 4 | 220117_at | ZNF385D | zinc finger protein 385D | Hs.21026 | 4.00 | 5.3 | | | |
| 5 | 205242_at | CXCL13 | chemokine (C-X-C motif) ligand 13 (B-cell chemoattractant) | Hs.100431 | 3.93 | 3.6 | Immune system process | leukocytes | BCA-1,J6 B-cell chemo-attractant |
| 6 | 234180_at | --- | --- | Hs.540997 | -3.40 | 0.8 | | | |
| 7 | 223750_s_at, 223751_x_at | TLR10 | toll-like receptor 10 | Hs.120551 | 2.91 | 4.2 | Immune system process | leukocytes | |
| 8 | 210072_at | CCL19 | chemokine (C-C motif) ligand 19 | Hs.50002 | 2.75 | 2.5 | Immune system process | leukocytes | |
| 9 | 217480_x_at | LOC339562 | similar to hCG1742442 | Hs.449972 | 2.73 | 5.3 | | | |
| 10 | 209663_s_at, 216331_at | ITGA7 | integrin, alpha 7 | Hs.524484 | -2.71 | 4.2 | | | |
| 11 | 231236_at | ZFP57 | zinc finger protein 57 homolog (mouse) | Hs.156326 | -2.62 | 3.6 | | | |
| 12 | 237731_at | LOC154092 | hypothetical protein LOC154092 | Hs.223718 | -2.59 | 1.4 | | | |
| 13 | 220245_at, 221644_s_at | SLC45A2 | solute carrier family 45, member 2 | Hs.278962 | -2.46 | 1.9 | | | |

FIGURE 5 – Table 1

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 14 | 213539_at | CD3D | CD3d molecule, delta (CD3-TCR complex) | Hs.504048 | 2.44 | 4.8 | Immune system process | T cells | |
| 15 | 1560030_at | LOC283692 | hypothetical protein LOC283692 | Hs.578667 | 2.43 | 4.2 | | | |
| 16 | 231496_at | FCAMR | Fc receptor, IgA, IgM, high affinity | Hs.145519 | 2.39 | 3.6 | | | |
| 17 | 206337_at | CCR7 | chemokine (C-C motif) receptor 7 | Hs.370036 | 2.37 | 3.6 | Response to stimulus | lymphocytes | CD197 |
| 18 | 227030_at | --- | | Hs.371680 | 2.37 | 4.2 | | | |
| 19 | 236301_at | --- | | Hs.371680 | 2.37 | 4.2 | | | |
| 20 | 204890_s_at, 204891_s_at | LCK | lymphocyte-specific protein tyrosine kinase | Hs.470627 | 2.37 | 4.2 | Immune system process | T cells | A Src family protein tyrosine kinase |
| 21 | 205890_s_at | GABBR1 | gamma-aminobutyric acid (GABA) B receptor, 1 ubiquitin D | Hs.44532 | 2.34 | 3.6 | Response to stimulus | | |
| 22 | 209795_at | CD69 | CD69 molecule | Hs.208854 | 2.33 | 4.2 | Immune system process | lymphocytes | |
| 23 | 204116_at | IL2RG | interleukin 2 receptor, gamma (severe combined immuno-deficiency)+D30 | Hs.84 | 2.31 | 4.2 | Immune system process | T cells | IL-2 receptor common gamma chain |

FIGURE 5 – Table 1 (cont)

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 24 | 211663_x_at, 212187_x_at, 211748_x_at | PTGDS | prostaglandin D2 synthase 21kDa (brain) | Hs.446429 | 2.28 | 3.6 | Response to stimulus | multiple | when expressed by hematopoietic cells acts as an allergic mediator |
| 25 | 206641_at | TNFRSF17 | tumor necrosis factor receptor superfamily, member 17 | Hs.2556 | 2.26 | 4.2 | Immune system process | B cells | CD269 |
| 26 | 205831_at | CD2 | CD2 molecule | Hs.523500 | 2.26 | 3.6 | Immune system process | T cells | |
| 27 | 206150_at | CD27 | CD27 molecule | Hs.355307 | 2.24 | 3.6 | Immune system process | T cells | |
| 28 | 203868_s_at | VCAM1 | vascular cell adhesion molecule 1 | Hs.109225 | 2.21 | 4.2 | | | |
| 29 | 204118_at, 237759_at | CD48 | CD48 molecule | Hs.243564 | 2.18 | 4.2 | Response to stimulus | lymphocytes | B cell membrane protein, ligand for CD2 |
| 30 | 214032_at, 1555613_a_at | ZAP70 | zeta-chain (TCR) associated protein kinase 70kDa | Hs.234569 | 2.18 | 4.2 | Immune system process | T cells | |
| 31 | 217549_at | --- | --- | Hs.527860 | 2.18 | 2.8 | | | |
| 32 | 1559754_at, 207339_s_at | LTB | Lymphotoxin beta (TNF superfamily, member 3) | Hs.376208 | 2.16 | 3.6 | Immune system process | leukocytes | |

FIGURE 5 – Table 1 (cont)

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 33 | 240068_at | C21orf130 | chromosome 21 open reading frame 130 | Hs.106234 | -2.15 | 2.5 | | | |
| 34 | 1555779_a_at, 205049_s_at | CD79A | CD79a molecule, immunoglobulin-associated alpha | Hs.631567 | 2.13 | 3.6 | Immune system process | B cells | |
| 35 | 204057_at | IRF8 | interferon regulatory factor 8 | Hs.137427 | 2.12 | 4.2 | Immune system process | leukocytes | |
| 36 | 205922_at | VNN2 | vanin 2 | Hs.293130 | 2.11 | 5.3 | | | |
| 37 | 231563_at | --- | --- | Hs.488388 | -2.11 | 4.2 | | | |
| 38 | 205159_at | CSF2RB | colony stimulating factor 2 receptor, beta, low-affinity (granulocyte-macrophage) | Hs.592192 | 2.10 | 4.2 | Receptor complex | | GM-CSF/IL-3/IL-5 receptor common beta-chain |
| 39 | 205085_at | ORC1L | origin recognition complex, subunit 1-like (yeast) | Hs.17908 | -2.08 | 2.5 | | | |
| 40 | 239340_at, 242715_at | --- | --- | Hs.444181 | -2.07 | 5.3 | | | |
| 41 | 202748_at | GBP2 | guanylate binding protein 2, interferon-inducible | Hs.386567 | 2.06 | 4.2 | Immune system process | multiple | |
| 42 | 215079_at | --- | --- | Hs.612917 | -2.05 | 1.9 | | | |
| 43 | 206651_s_at | CPB2 | carboxypeptidase B2 (plasma) | Hs.512937 | -2.05 | 1.7 | | | |
| 44 | 202531_at | IRF1 | interferon regulatory factor 1 | Hs.436061 | 2.03 | 4.2 | Immune system process | not clear | |

FIGURE 5 – Table 1 (cont)

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 45 | 1559065_a_at | CLEC4G | C-type lectin superfamily 4, member G | Hs.220649 | 2.02 | 4.2 | | | |
| 46 | 1555292_at, 231880_at | FAM40B | family with sequence similarity 40, member B | Hs.489988 | -2.02 | 2.5 | | | |
| 47 | 210642_at | CCIN | calicin | Hs.115460 | -2.01 | 4.8 | | | |
| 48 | 236295_s_at | NLRC3 | NLR family, CARD domain containing 3 | Hs.592091 | 2.00 | 2.8 | Immune system process | T cells | NOD3 |
| 50 | 222346_at, 227048_at | LAMA1 | laminin, alpha 1 | Hs.270364 | -1.99 | 0.7 | | | |
| 51 | 206375_s_at | HSPB3 | heat shock 27kDa protein 3 | Hs.41707 | 1.98 | 4.2 | Response to stimulus | not clear | |
| 52 | 206666_at | GZMK | granzyme K (granzyme 3; tryptase II) | Hs.277937 | 1.98 | 4.8 | | | |
| 53 | 206134_at | ADAMDEC1 | ADAM-like, decysin 1 | Hs.521459 | 1.97 | 4.8 | Cell communication | dendritic cells (DC), macrophages | |
| 54 | 1553856_s_at, 214615_at | P2RY10 | purinergic receptor P2Y, G-protein coupled, 10 | Hs.296433 | 1.96 | 3.6 | Cell communication | leukocytes | |
| 55 | 234675_x_at | --- | --- | Hs.532596 | 1.96 | 4.2 | | | |
| 56 | 208514_at, 236407_at | KCNE1 | potassium voltage-gated channel, Isk-related family, member 1 | Hs.121495 | -1.95 | 1.2 | | | |
| 57 | 1557103_a_at | LMTK3 | lemur tyrosine kinase 3 | Hs.207426 | 1.94 | 4.2 | | | |

FIGURE 5 – Table 1 (cont)

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 59 | 243175_at | UTS2D | urotensin 2 domain containing | Hs.518492 | -1.93 | 0.0 | | | |
| 60 | 205440_s_at | NPY1R | neuropeptide Y receptor Y1 | Hs.519057 | 1.93 | 3.6 | Response to stimulus | central and peripheral nervous system | a neuro-transmitter receptor |
| 61 | 235334_at | ST6GALNAC | ST6 (alpha-N-acetyl-neuraminyl-2,3-beta-galactosyl-1,3)-N-acetylgalactosaminide alpha-2,6-sialyltransferase 3 | Hs.337040 | -1.92 | 1.2 | | | |
| 62 | 210279_at | GPR18 | G protein-coupled receptor 18 | Hs.631765 | 1.91 | 4.2 | | | |
| 63 | 217147_s_at | TRAT1 | T cell receptor associated transmembrane adaptor 1 | Hs.138701 | 1.91 | 4.8 | Immune system process | T cells | |
| 64 | 202523_s_at, 202524_s_at | SPOCK2 | sparc/osteonectin, cwcv and kazal-like domains proteoglycan (testican) 2 | Hs.523009 | 1.90 | 2.5 | | | |
| 65 | 205081_at | CRIP1 | cysteine-rich protein 1 (intestinal) | Hs.70327 | 1.88 | 3.6 | | | |
| 66 | 207145_at | MSTN | myostatin | Hs.41565 | -1.87 | 4.2 | | | |

FIGURE 5 – Table 1 (cont)

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 67 | 218806_s_at, 218807_at, 224221_s_at | VAV3 | vav 3 guanine nucleotide exchange factor | Hs.267659 | -1.87 | 4.2 | | | |
| 68 | 217640_x_at | C18orf24 | chromosome 18 open reading frame 24 | Hs.134726 | -1.86 | 0.7 | M Phase | | |
| 69 | 204923_at | SASH3 | SAM and SH3 domain containing 3 | Hs.61469 | 1.86 | 4.2 | | | |
| 70 | 223836_at | FGFBP2 | fibroblast growth factor binding protein 2 | Hs.98785 | -1.85 | 4.2 | | | |
| 71 | 230245_s_at, 230648_at | LOC283663 | hypothetical protein LOC283663 | Hs.181297 | 1.85 | 4.8 | | | |
| 72 | 208590_x_at, 239572_at | GJA3 | gap junction protein, alpha 3, 46kDa | Hs.130313 | -1.85 | 1.9 | | | |
| 73 | 220892_s_at, 223062_s_at | PSAT1 | phosphoserine aminotransferase 1 | Hs.494261 | -1.84 | 1.6 | Cofactor Binding | | |
| 74 | 1559462_at | --- | --- | Hs.446446 | -1.83 | 1.7 | | | |
| 75 | 229686_at | P2RY8 | purinergic receptor P2Y, G-protein coupled, 8 | Hs.111377 | 1.83 | 3.6 | Cell communication | leukocytes | |
| 76 | 237357_at | --- | --- | Hs.221513 | 1.83 | 4.2 | | | |
| 77 | 1561704_at | --- | --- | Hs.639381 | 1.83 | 4.2 | | | |
| 78 | 1555349_a_at, 202803_s_at, 236988_x_at | ITGB2 | integrin, beta 2 (complement component 3 receptor 3 and 4 subunit) | Hs.375957 | 1.83 | 4.2 | Immune system process | leukocytes | CD18 |

FIGURE 5 – Table 1 (cont)

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 79 | 1554240_a_at, 213475_s_at | ITGAL | integrin, alpha L (antigen CD11A (p180), lymphocyte function-associated antigen 1; alpha polypeptide) | Hs.174103 | 1.81 | 4.2 | Immune system process | leukocytes | CD11a |
| 80 | 238219_at | C12orf50 | chromosome 12 open reading frame 50 | Hs.112930 | -1.80 | 2.1 | | | |
| 81 | 240901_at | --- | --- | Hs.547840 | 1.80 | 3.6 | | | |
| 82 | 1562537_at, 211734_s_at | FCER1A | Fc fragment of IgE, high affinity I, receptor for; alpha polypeptide | Hs.897 | 1.80 | 4.8 | Immune system process | leukocytes | Fc receptor for IgE |
| 83 | 226474_at | NLRC5 | NLR family, CARD domain containing 5 | Hs.528836 | 1.80 | 4.2 | Response to stimulus | not clear | |
| 84 | 1554984_a_at, 205671_s_at | HLA-DOB | major histocompatibility complex, class II, DO beta | Hs.1802 | 1.79 | 5.3 | Immune system process | leukocytes | |
| 85 | 1558522_at | --- | --- | Hs.594275 | -1.78 | 1.7 | | | |
| 86 | 241476_at | --- | --- | Hs.299538 | 1.78 | 3.6 | | | |
| 87 | 1562475_at, 216877_at, 216874_at | DKFZp686O1 | hypothetical gene supported by BC043549; BX648102 | Hs.42192 | -1.78 | 1.6 | | | |
| 88 | 1554474_a_at, 209708_at, 243697_at | MOXD1 | monooxygenase, DBH-like 1 | Hs.6909 | -1.77 | 0.8 | | | |
| 89 | 233767_at | --- | --- | Hs.636837 | 1.77 | 2.5 | | | |

FIGURE 5 – Table 1 (cont)

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 90 | 201502_s_at | NFKBIA | nuclear factor of kappa light polypeptide gene enhancer in B-cells inhibitor, alpha | Hs.81328 | 1.77 | 4.2 | Immune system process | leukocytes | |
| 91 | 244125_at | --- | | Hs.601938 | 1.76 | 4.2 | | | |
| 92 | 243154_at | --- | | Hs.86650 | 1.76 | 2.5 | | | |
| 93 | 223805_at, 236261_at, 238575_at | OSBPL6 | oxysterol binding protein-like 6 | Hs.318775 | -1.75 | 0.8 | | | |
| 94 | 1570469_at | --- | | Hs.460033 | -1.75 | 4.8 | | | |
| 95 | 202307_s_at | TAP1 | transporter 1, ATP-binding cassette, sub-family B (MDR/TAP) | Hs.352018 | 1.75 | 4.2 | Immune system process | multiple | |
| 96 | 1560100_at, 242138_at | DLX1 | distal-less homeobox 1 | Hs.407015 | -1.74 | 2.5 | | | |
| 97 | 228262_at | MAP7D2 | MAP7 domain containing 2 | Hs.127951 | -1.74 | 0.7 | | | |
| 98 | 1561336_at, 205554_s_at | DNASE1L3 | deoxyribonuclease I-like 3 | Hs.476453 | 1.74 | 4.8 | Cell communication | liver and spleen | |
| 99 | 1561021_at | --- | | Hs.255813 | 1.74 | 4.2 | | | |
| 100 | 209294_x_at, 209295_at, 210405_x_at | TNFRSF10B | tumor necrosis factor receptor superfamily, member 10b | Hs.521456 | -1.73 | 2.1 | | | |
| 101 | 227055_at | METTL7B | methyltransferase like 7B | Hs.51483 | -1.73 | 2.8 | | | |
| 102 | 1554834_a_at, 223322_at | RASSF5 | Ras association (RalGDS/AF-6) domain family member 5 | Hs.497579 | 1.73 | 4.2 | Response to stimulus | leukocytes, tumors | |

FIGURE 5 – Table 1 (cont)

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 103 | 206660_at | IGLL1 | immunoglobulin lambda-like polypeptide 1 | Hs.348935 | 1.72 | 2.5 | Immune system process | B cells | |
| 104 | 1569510_at | --- | --- | Hs.621242 | 1.72 | 2.5 | | | |
| 105 | 226219_at, 241346_at | ARHGAP30 | Rho GTPase activating protein 30 | Hs.389374 | 1.72 | 4.8 | Cell communication | | |
| 106 | 1570268_at | --- | --- | Hs.518877 | 1.71 | 2.5 | | | |
| 107 | 219898_at, 234303_s_at | GPR85 | G protein-coupled receptor 85 | Hs.152009 | -1.71 | 0.8 | | | |
| 108 | 206687_s_at | PTPN6 | protein tyrosine phosphatase, non-receptor type 6 | Hs.63489 | 1.71 | 4.8 | Response to stimulus | hematopoietic | PTP-1C, SHP 1, hematopoietic cell protein-tyrosine phosphatase |
| 109 | 239689_at | --- | --- | Hs.369782 | 1.71 | 4.2 | | | |
| 110 | 203440_at, 203441_s_at | CDH2 | cadherin 2, type 1, N-cadherin (neuronal) | Hs.464829 | -1.71 | 0.7 | | | |
| 111 | 219699_at | LGI2 | leucine-rich repeat LGI family, member 2 | Hs.12488 | 1.70 | 3.6 | | | |
| 112 | 241790_at | --- | --- | Hs.385861 | -1.69 | 0.0 | | | |
| 113 | 220485_s_at | SIRPG | signal-regulatory protein gamma | Hs.590883 | 1.69 | 2.8 | Immune system process | T cells | CD172g |
| 114 | 237753_at | --- | --- | Hs.634845 | 1.69 | 3.6 | | | |

FIGURE 5 – Table 1 (cont)

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 115 | 208358_s_at, 228956_at | UGT8 | UDP glycosyltransferase 8 (UDP-galactose ceramide galactosyltransferase) | Hs.144197 | -1.69 | 4.2 | | | |
| 116 | 1561899_at, 244413_at | CLECL1 | C-type lectin-like 1 | Hs.560087 | 1.69 | 2.5 | | | |
| 117 | 220577_at | GVIN1 | GTPase, very large interferon inducible 1 | Hs.494757 | 1.69 | 4.2 | | | |
| 118 | 1560689_s_at, 203809_s_at, 211453_s_at, 225471_s_at, 226156_at, 236664_at | AKT2 | V-akt murine thymoma viral oncogene homolog 2 | Hs.631535 | -1.68 | 5.3 | | | |
| 119 | 238504_at | C6orf57 | chromosome 6 open reading frame 57 | Hs.418495 | -1.68 | 2.8 | | | |
| 120 | 208303_s_at | CRLF2 | cytokine receptor-like factor 2 | Hs.287729 | 1.68 | 4.2 | | | |
| 121 | 206310_at | SPINK2 | serine peptidase inhibitor, Kazal type 2 (acrosin-trypsin inhibitor) | Hs.98243 | 1.68 | 3.6 | | | |
| 122 | 208394_x_at | ESM1 | endothelial cell-specific molecule 1 | Hs.129944 | -1.67 | 3.6 | | | |
| 123 | 230312_at | --- | --- | Hs.88045 | -1.67 | 0.8 | | | |
| 124 | 228094_at | AMICA1 | adhesion molecule, interacts with CXADR antigen 1 | Hs.16291 | 1.67 | 3.6 | | | |
| 125 | 230874_at | --- | --- | Hs.596383 | -1.67 | 2.8 | | | |

FIGURE 5 – Table 1 (cont)

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 126 | 1554362_at, 220766_at | BTG4 | B-cell translocation gene 4 | Hs.128180 | 1.67 | 3.6 | | | |
| 127 | 235572_at | SPC24 | SPC24, NDC80 kinetochore complex component, homolog (S. cerevisiae) | Hs.381225 | -1.66 | 1.6 | M Phase | | |
| 128 | 241190_at | --- | --- | Hs.197082 | 1.66 | 4.8 | | | |
| 129 | 230921_s_at | MAP3K12 | --- | Hs.593270 | 1.66 | 4.2 | Cell communication | Keratinocytes | |
| 130 | 1554717_a_at, 204491_at, 210836_x_at, 210837_s_at, 211840_s_at, 228962_at | PDE4D | phosphodiesterase 4D, cAMP-specific (phosphodiesterase E3 dunce homolog, Drosophila) | Hs.117545 | -1.66 | 2.8 | | | |
| 131 | 214049_x_at, 214551_s_at | CD7 | CD7 molecule | Hs.36972 | 1.65 | 4.2 | Immune system process | T cells | |
| 132 | 1552386_at | C5orf29 | chromosome 5 open reading frame 29 | Hs.547697 | 1.65 | 4.2 | | | |
| 133 | 211353_at | LRIT1 | leucine-rich repeat, immunoglobulin-like and transmembrane domains 1 | Hs.226000 | -1.65 | 3.6 | | | |
| 134 | 223625_at, 227239_at, 231396_s_at, 244115_at | FAM126A | family with sequence similarity 126, member A | Hs.85603 | -1.65 | 3.2 | | | |

FIGURE 5 – Table 1 (cont)

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 136 | 203331_s_at, 203332_s_at | INPP5D | inositol polyphosphate-5-phosphatase, 145kDa | Hs.262886 | 1.65 | 4.8 | Immune system process | leukocytes | SHIP-1 |
| 137 | 201137_s_at | HLA-DPB1 | major histocompatibility complex, class II, DP beta 1 | Hs.485130 | 1.64 | 5.3 | Immune system process | leukocytes | |
| 138 | 237802_at | XKR4 | XK, Kell blood group complex subunit-related family, member 4 | Hs.130197 | 1.64 | 3.6 | | | |
| 139 | 237425_at | LOC474358 | hypothetical BC042079 locus | Hs.348526 | 1.64 | 4.2 | | | |
| 140 | 230339_at, 235644_at | CCDC138 | Coiled-coil domain containing 138 | Hs.362702 | -1.64 | 4.2 | | | |
| 141 | 225415_at | DTX3L | deltex 3-like (Drosophila) | Hs.518201 | 1.64 | 4.2 | | | |
| 142 | 206631_at | PTGER2 | prostaglandin E receptor 2 (subtype EP2), 53kDa | Hs.2090 | 1.63 | 3.6 | Cell communication | placenta and lung | |
| 143 | 1560676_at | LOC283514 | similar to seven in absentia 2 | Hs.368483 | 1.63 | 3.6 | | | |
| 144 | 239922_at | CCDC142 | coiled-coil domain containing 142 | Hs.430199 | -1.63 | 2.1 | | | |
| 145 | 207752_x_at, 211531_x_at, 210597_x_at | PRB1 | proline-rich protein BstNI subfamily 1 | Hs.631726 | 1.63 | 3.6 | | | |
| 146 | 239579_at | ABHD7 | abhydrolase domain containing 7 | Hs.201555 | -1.63 | 2.5 | | | |

FIGURE 5 – Table 1 (cont)

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 147 | 205790_at | SKAP1 | src kinase associated phosphoprotein 1 | Hs.316931 | 1.62 | 4.2 | Immune system process | T cells | |
| 148 | 216030_s_at | SEMG2 | semenogelin II | Hs.537218 | 1.62 | 4.2 | | | |
| 149 | 206256_at | CPN1 | carboxypeptidase N, polypeptide 1 | Hs.2246 | -1.62 | 1.7 | | | |
| 150 | 243942_at | --- | | Hs.575572 | 1.62 | 4.2 | | | |
| 151 | 209040_s_at | PSMB8 | proteasome (prosome, macropain) subunit, beta type, 8 (large multifunctional peptidase 7) | Hs.180062 | 1.62 | 4.2 | Immune system process | leukocytes | immunoproteasome subunit |
| 152 | 238452_at | FCRLB | Fc receptor-like B | Hs.517422 | -1.62 | 0.7 | | | |
| 153 | 233829_at | C20orf118 | chromosome 20 open reading frame 118 | Hs.472630 | 1.62 | 4.2 | | | |
| 154 | 212141_at, 212142_at, 222036_s_at, 222037_at | MCM4 | minichromosome maintenance complex component 4 | Hs.460184 | -1.61 | 0.7 | | | |
| 155 | 208694_at, 210543_s_at, 215757_at | PRKDC | protein kinase, DNA-activated, catalytic polypeptide | Hs.491682 | -1.61 | 2.5 | | | |
| 156 | 218039_at, 219978_s_at | NUSAP1 | nucleolar and spindle associated protein 1 | Hs.615092 | -1.61 | 0.0 | M Phase | | |
| 157 | 205598_at | TRAIP | TRAF interacting protein | Hs.517972 | -1.61 | 2.1 | | | |

FIGURE 5 -- Table 1 (cont)

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 158 | 210432_s_at, 232512_at | SCN3A | sodium channel, voltage-gated, type III, alpha subunit | Hs.435274 | 1.61 | 4.8 | | | |
| 159 | 236226_at | BTLA | lymphocyte B and T associated | Hs.445162 | 1.61 | 4.2 | Immune system process | leukocytes | CD272 |
| 160 | 227051_at | --- | --- | Hs.43047 | -1.60 | 2.8 | | | |
| 161 | 201531_at | ZFP36 | zinc finger protein 36, C3H type, homolog (mouse) | Hs.534052 | 1.60 | 4.2 | Immune system process | not clear | Functions in TNFa effect |
| 162 | 219148_at | PBK | PDZ binding kinase | Hs.104741 | -1.60 | 0.0 | M Phase | | |
| 163 | 1554403_a_at | --- | --- | Hs.553957 | -1.60 | 1.2 | | | |
| 164 | 207329_at | MMP8 | matrix metallopeptidase 8 (neutrophil collagenase) | Hs.161839 | -1.60 | 1.6 | | | |
| 165 | 203393_at, 203394_s_at, 203395_s_at | HES1 | hairy and enhancer of split 1, (Drosophila) | Hs.250666 | -1.60 | 2.1 | | | |
| 166 | 209813_x_at | TARP | TCR gamma alternate reading frame protein | Hs.534032 | 1.59 | 4.2 | | | |
| 167 | 211144_x_at, 217374_x_at, 216920_s_at | TRGC2 /// TARP | T cell receptor gamma constant 2 /// TCR gamma alternate reading frame protein | Hs.534032 | 1.59 | 4.2 | | | |
| 168 | 227554_at, 229480_at, 235267_at | --- | --- | Hs.31474 | -1.59 | 4.8 | | | |
| 169 | 210439_at | ICOS | inducible T-cell co-stimulator | Hs.56247 | 1.59 | 3.6 | Immune system process | T cells | ICOS |

FIGURE 5 – Table 1 (cont)

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 170 | 1554908_at, 1554907_a_at, 243354_at, 232984_at, 220098_at, 204252_at, | HYDIN | hydrocephalus inducing homolog (mouse) | Hs.461229 | 1.59 | 4.8 | | | |
| 171 | 211803_at, 211804_s_at | CDK2 | cyclin-dependent kinase 2 | Hs.19192 | -1.59 | 3.2 | M Phase | | |
| 172 | 203470_s_at, 203471_s_at | PLEK | pleckstrin | Hs.468840 | 1.59 | 4.2 | Cell communication | not clear | substrate of platelets |
| 173 | 205519_at | WDR76 | WD repeat domain 76 | Hs.250154 | -1.59 | 3.2 | | | |
| 174 | 205543_at | HSPA4L | heat shock 70kDa protein 4-like | Hs.135554 | -1.59 | 2.1 | | | |
| 175 | 206323_x_at | OPHN1 | oligophrenin 1 | Hs.128824 | 1.59 | 4.2 | | | |
| 176 | 207444_at | SLC22A13 | solute carrier family 22, member 13 | Hs.225941 | -1.59 | 4.2 | | | |
| 177 | 204018_x_at, 217414_x_at, 214414_x_at, 211745_x_at, 211699_x_at, 209458_x_at | HBA1///HBA2 | hemoglobin, alpha 1///hemoglobin, alpha 2 | Hs.449630 | 1.59 | 4.8 | | | |
| 178 | 204265_s_at, 214847_s_at | GPSM3 | G-protein signaling modulator 3 (AGS3-like, C. elegans) | Hs.520046 | 1.59 | 2.8 | Immune system process | not clear | |
| 179 | 233669_s_at | TRIM54 | tripartite motif-containing 54 | Hs.516036 | 1.59 | 4.2 | Cell communication | | |
| 180 | 201008_s_at, 201009_s_at, 201010_s_at | TXNIP | thioredoxin interacting protein | Hs.533977 | 1.59 | 4.8 | Response to stimulus | multiple | required for NK cell maturation |

FIGURE 5 – Table 1 (cont)

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 181 | 208206_s_at, 214369_s_at, 214368_at, 214367_at | RASGRP2 | RAS guanyl releasing protein 2 (calcium and DAG-regulated) | Hs.99491 | 1.58 | 4.2 | Response to stimulus | multiple | |
| 182 | 202223_at | STT3A | STT3, subunit of the oligosaccharyl-transferase complex, homolog A (S. cerevisiae) | Hs.504237 | -1.58 | 1.2 | | | |
| 183 | 1561737_at | --- | --- | Hs.573815 | 1.58 | 2.5 | | | |
| 184 | 205901_at | PNOC | prepronociceptin | Hs.88218 | 1.58 | 5.3 | Cell communication | central and peripheral nervous system | |
| 185 | 238815_at | LRRTM1 | leucine rich repeat transmembrane neuronal 1 | Hs.591580 | -1.58 | 5.3 | | | |
| 186 | 209733_at | LOC286440 | hypothetical protein LOC286440 | Hs.348844 | 1.58 | 3.6 | | | |
| 187 | 218782_s_at, 222740_at, 228401_at, 235266_at | ATAD2 | ATPase family, AAA domain containing 2 | Hs.370834 | -1.57 | 0.0 | | | |
| 188 | 239509_at | --- | hypothetical protein LOC283711 | Hs.111539 | -1.57 | 3.2 | | | |
| 189 | 1564463_at | LOC283711 | | Hs.585100 | 1.57 | 4.2 | | | |
| 190 | 219249_s_at | FKBP10 | FK506 binding protein 10, 65 kDa | Hs.463035 | -1.57 | 3.6 | | | |
| 191 | 229490_s_at | --- | --- | Hs.133294 | -1.57 | 0.7 | | | |

FIGURE 5 – Table 1 (cont)

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 192 | 1563137_at, 238445_x_at | MGAT5B | mannosyl (alpha-1,6-)-glycoprotein beta-1,6-N-acetyl-glucosaminyltransferase, isozyme B | Hs.144531 | -1.56 | 0.7 | | | |
| 193 | 210313_at | LILRA4 | leukocyte immunoglobulin-like receptor, subfamily A (with TM domain), member 4 | Hs.406708 | 1.56 | 3.6 | Immune system process | Plasmacytoid DCs | CD85g |
| 194 | 218614_at, 227152_at | C12orf35 | chromosome 12 open reading frame 35 | Hs.445129 | 1.56 | 4.2 | | | |
| 195 | 230423_at | --- | --- | Hs.120204 | -1.56 | 2.5 | | | |
| 196 | 1566215_at, 1566217_at | --- | --- | Hs.606954 | 1.56 | 4.2 | | | |
| 197 | 209309_at, 217014_s_at | AZGP1 | alpha-2-glycoprotein 1, zinc-binding | Hs.546239 | -1.56 | 4.2 | | | |
| 198 | 1557154_at, 1557155_a_at, 241440_at, 205048_s_at | FLJ30375 | Hypothetical gene supported by AK054937 | Hs.535724 | -1.56 | 0.8 | | | |
| 199 | 205194_at, 244819_x_at | PSPH | phosphoserine phosphatase | Hs.512656 | -1.56 | 2.1 | | | |
| 200 | 240315_at | --- | --- | Hs.363386 | 1.56 | 3.6 | | | |
| 201 | 210712_at | LDHAL6B | lactate dehydrogenase A-like 6B | Hs.307052 | 1.56 | 4.2 | | | |
| 202 | 241483_at | --- | --- | Hs.62772 | 1.55 | 2.5 | | | |
| 203 | 1562997_a_at | --- | --- | Hs.436357 | -1.55 | 2.8 | | | |

FIGURE 5 – Table 1 (cont).

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 205 | 224920_x_at, 225673_at | MYADM | myeloid-associated differentiation marker | Hs.380906 | 1.55 | 4.8 | | | |
| 206 | 1565818_s_at, 231929_at, 220567_at, 1555060_a_at, 216901_s_at, 205039_s_at | IKZF1 | IKAROS family zinc finger 1 (Ikaros) | Hs.435949 | 1.55 | 4.2 | | | |
| 207 | 206141_at | MOCS3 | molybdenum cofactor synthesis 3 | Hs.159410 | -1.55 | 2.1 | | | |
| 208 | 204603_at | EXO1 | exonuclease 1 | Hs.498248 | -1.54 | 0.7 | M Phase | | |
| 209 | 221134_at | ANGPT4 | angiopoietin 4 | Hs.278973 | 1.54 | 4.2 | Cell communication | lungs | |
| 210 | 223820_at | RBP5 | retinol binding protein 5, cellular | Hs.246046 | 1.54 | 4.2 | | | |
| 211 | 220418_at | UBASH3A | ubiquitin associated and SH3 domain containing, A | Hs.473912 | 1.54 | 3.6 | Immune system process | T cells | Suppressor of T-cell signalling |
| 212 | 227552_at | SEP1 | septin 1 | Hs.632176 | 1.54 | 3.6 | | | |
| 213 | 244479_at | --- | | Hs.126664 | -1.54 | 1.2 | | | |
| 214 | 219926_at | POPDC3 | popeye domain containing 3 | Hs.458336 | -1.54 | 0.7 | | | |
| 215 | 204470_at | CXCL1 | chemokine (C-X-C motif) ligand 1 (melanoma growth stimulating activity, alpha) | Hs.789 | -1.54 | 5.3 | | | |
| 216 | 1561625_at | --- | | Hs.563806 | 1.54 | 4.8 | | | |

FIGURE 5 – Table 1 (cont)

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 217 | 204727_at, 204728_s_at, 216228_s_at | WDHD1 | WD repeat and HMG-box DNA binding protein 1 | Hs.385998 | -1.54 | 1.2 | | | |
| 218 | 205195_at, 205196_s_at, 209635_at | AP1S1 | adaptor-related protein complex 1, sigma 1 subunit | Hs.563509 | -1.54 | 3.2 | | | |
| 219 | 208050_s_at, 209811_at, 209812_x_at, 211140_s_at, 226032_at, 226036_x_at, 34449_at | CASP2 | caspase 2, apoptosis-related cysteine peptidase (neural precursor cell expressed, developmentally down-regulated 2) | Hs.368982 | -1.54 | 2.8 | | | |
| 220 | 221008_s_at | AGXT2L1 | alanine-glyoxylate aminotransferase 2-like 1 | Hs.106576 | -1.54 | 1.7 | Cofactor Binding | | |
| 221 | 1564139_at | LOC144571 | hypothetical protein LOC144571 | Hs.592432 | 1.53 | 4.2 | | | |
| 222 | 213172_at, 213174_at | TTC9 | tetratricopeptide repeat domain 9 | Hs.79170 | 1.53 | 4.2 | | | |
| 223 | 223593_at | AADAT | aminoadipate aminotransferase | Hs.529735 | -1.53 | 4.2 | Cofactor Binding | | |
| 224 | 1552818_a_at, 207369_at | BRS3 | bombesin-like receptor 3 | Hs.121484 | -1.53 | 3.2 | | | |
| 225 | 212092_at, 212094_at | PEG10 | paternally expressed 10 | Hs.147492 | -1.53 | 4.8 | | | |
| 226 | 218994_s_at, 222801_s_at, 231521_at | STAG3L4 | stromal antigen 3-like 4 | Hs.632013 | -1.53 | 4.2 | | | |

FIGURE 5 – Table 1 (cont)

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 227 | 1557370_s_at, 201960_s_at, 201959_s_at, 1561082_at | MYCBP2 | MYC binding protein 2 | Hs.591221 | 1.53 | 2.8 | | | |
| 228 | 202007_at, 202008_s_at | NID1 | nidogen 1 | Hs.356624 | -1.53 | 0.8 | | | |
| 229 | 225203_at | PPP1R16A | protein phosphatase 1, regulatory (inhibitor) subunit 16A | Hs.521937 | -1.53 | 0.7 | | | |
| 230 | 217412_at | --- | | Hs.494972 | 1.53 | 3.6 | | | |
| 231 | 1564074_at | --- | | Hs.562365 | 1.53 | 4.2 | | | |
| 232 | 230956_at, 238701_x_at | FLJ45803 | FLJ45803 protein | Hs.125166 | 1.52 | 4.2 | | | |
| 233 | 205937_at | CGREF1 | cell growth regulator with EF-hand domain 1 | Hs.159525 | -1.52 | 3.6 | Cell Cycle Phase | | |
| 234 | 202314_at, 216607_s_at | CYP51A1 | cytochrome P450, family 51, subfamily A, polypeptide 1 | Hs.417077 | -1.52 | 0.7 | | | |
| 235 | 201870_at | TOMM34 | translocase of outer mitochondrial membrane 34 | Hs.517066 | -1.52 | 0.7 | | | |
| 236 | 1552623_at | HSH2D | hematopoietic SH2 domain containing | Hs.631617 | 1.52 | 2.5 | Immune system process | T cells | mediates signalling through TCR and CD28 |
| 237 | 230805_at | --- | | Hs.355944 | 1.52 | 4.2 | | | |
| 238 | 230980_x_at, 231038_s_at | --- | | Hs.355944 | 1.52 | 4.2 | | | |

FIGURE 5 – Table 1 (cont)

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 239 | 200737_at, 227068_at, 217383_at, 217356_s_at, 200738_s_at | PGK1 | phosphoglycerate kinase 1 | Hs.78771 | -1.52 | 0.8 | | | |
| 240 | 238576_at | --- | | Hs.592734 | -1.52 | 3.2 | | | |
| 241 | 1570300_at | --- | | Hs.348434 | 1.52 | 4.8 | | | |
| 242 | 1552619_a_at, 222608_s_at | ANLN | anillin, actin binding protein | Hs.62180 | -1.51 | 0.8 | M Phase | | |
| 243 | 235736_at | --- | | Hs.178144 | -1.51 | 0.7 | | | |
| 244 | 221117_at | --- | | Hs.543586 | 1.51 | 4.2 | | | |
| 245 | 208277_at | PITX3 | paired-like homeodomain 3 | Hs.137568 | 1.51 | 3.6 | | | |
| 246 | 204033_at | TRIP13 | thyroid hormone receptor interactor 13 | Hs.436187 | -1.51 | 0.7 | | | |
| 247 | 205959_at | MMP13 | matrix metallopeptidase 13 (collagenase 3) | Hs.2936 | -1.51 | 4.2 | | | |
| 248 | 203233_at, 242743_at | IL4R | interleukin 4 receptor | Hs.513457 | 1.50 | 4.8 | Immune system process | leukocytes | CD124, IL4Ra |
| 249 | 240049_at | DLG5 | --- | Hs.626305 | 1.50 | 4.2 | Cell communication | Epithelial cells | |
| 250 | 229147_at | RASSF6 | Ras association (RalGDS/AF-6) domain family 6, Ras association domain-containing protein 6. | Hs.529677 | 1.50 | 4.2 | Cell communication | multiple | |
| 251 | 203408_s_at | SATB1 | SATB homeobox 1 | Hs.517717 | 1.50 | 4.2 | | | |

FIGURE 5 – Table 1 (cont)

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 252 | 210090_at | ARC | activity-regulated cytoskeleton-associated protein | Hs.40888 | -1.50 | 4.8 | | | |
| 253 | 219556_at | C16orf59 | chromosome 16 open reading frame 59 | Hs.534491 | -1.50 | 0.0 | | | |
| 254 | 228298_at | FAM113B | family with sequence similarity 113, member B | Hs.560100 | 1.50 | 3.6 | | | |
| 255 | 205676_at | CYP27B1 | cytochrome P450, family 27, subfamily B, polypeptide 1 | Hs.524528 | -1.50 | 4.2 | | | |
| 256 | 207256_at | MBL2 | mannose-binding lectin (protein C) 2, soluble (opsonic defect) | Hs.499674 | 1.50 | 4.2 | Immune system process | leukocytes | MBP1 |
| 257 | 227929_at | --- | | Hs.586760 | 1.49 | 3.6 | | | |
| 258 | 218984_at | PUS7 | pseudouridylate synthase 7 homolog (S. cerevisiae) | Hs.520619 | -1.49 | 2.5 | | | |
| 259 | 235428_at, 243749_s_at, 244411_at | --- | | Hs.446671 | -1.49 | 4.8 | | | |
| 260 | 230896_at, 238101_at | CCDC4 | coiled-coil domain containing 4 | Hs.120591 | 1.49 | 3.6 | | | |

FIGURE 5 – Table 1 (cont)

| Probe # | AFFY ID(s) | Gene Symbol | Gene Title | UniGene ID | FC | q-value (%) | Top Functional Gene Category (DAVID) | Cells expressing | Notes and aliases |
|---|---|---|---|---|---|---|---|---|---|
| 261 | 1554540_at, 242283_at | DNAH14 | dynein, axonemal, heavy chain 14 /// chromosome 1 open reading frame 67 /// similar to CG7092-PA | Hs.133977 | -1.49 | 0.0 | | | |
| 262 | 227165_at | C13orf3 | chromosome 13 open reading frame 3 | Hs.88523 | -1.49 | 1.4 | | | |
| 263 | 225798_at, 225800_at | JAZF1 | JAZF zinc finger 1 | Hs.368944 | -1.49 | 4.8 | | | |
| 264 | 235949_at | --- | --- | Hs.133020 | -1.49 | 0.0 | | | |
| 265 | 1552660_a_at, 1565939_at, 203738_at | C5orf22 | chromosome 5 open reading frame 22 | Hs.519246 | -1.48 | 4.8 | | | |
| 266 | 1561990_at | LOC157931 | hypothetical protein LOC157931 | Hs.97461 | 1.48 | 4.2 | | | |

FIGURE 5 – Table 1 (cont)

FIGURE 6

Table 2 (TOP 100 GENES)

| Probe # | AFFY ID(s) | Gene Symbol | Gene Title | UniGene ID | FC | q-value (%) | Top Functional Gene Category (DAVID) |
|---|---|---|---|---|---|---|---|
| 59 | 243175_at | UTS2D | urotensin 2 domain containing | Hs.518492 | -1.93 | 0.0 | |
| 112 | 241790_at | --- | --- | Hs.385861 | -1.69 | 0.0 | |
| 156 | 218039_at, 219978_s_at | NUSAP1 | nucleolar and spindle associated protein 1 | Hs.615092 | -1.61 | 0.0 | M Phase |
| 162 | 219148_at | PBK | PDZ binding kinase | Hs.104741 | -1.60 | 0.0 | M Phase |
| 187 | 218782_s_at, 222740_at, 228401_at, 235266_at | ATAD2 | ATPase family, AAA domain containing 2 | Hs.370834 | -1.57 | 0.0 | |
| 253 | 219556_at | C16orf59 | chromosome 16 open reading frame 59 | Hs.534491 | -1.50 | 0.0 | |
| 261 | 1554540_at, 242283_at | DNAH14 | dynein, axonemal, heavy chain 14 /// chromosome 1 open reading frame 67 /// similar to CG7092-PA | Hs.133977 | -1.49 | 0.0 | |
| 264 | 2335949_at | --- | --- | Hs.133020 | -1.49 | 0.0 | |
| 1 | 236967_at | LOC645249 | hypothetical protein LOC645249 | Hs.224879 | -14.34 | 0.7 | |
| 50 | 2223346_at, 227048_at | LAMA1 | laminin, alpha 1 | Hs.270364 | -1.99 | 0.7 | |

FIGURE 6 (continued)

| | | | | | |
|---|---|---|---|---|---|
| 68 | 217640_x_at | C18orf24 | chromosome 18 open reading frame 24 | Hs.134726 | -1.86 | 0.7 | M Phase |
| 97 | 228262_at | MAP7D2 | MAP7 domain containing 2 | Hs.127951 | -1.74 | 0.7 | |
| 110 | 203440_at, 203441_s_at | CDH2 | cadherin 2, type 1, N-cadherin (neuronal) | Hs.464829 | -1.71 | 0.7 | |
| 59 | 243175_at | UTS2D | urotensin 2 domain containing | Hs.518492 | -1.93 | 0.0 | |
| 152 | 238452_at | FCRLB | Fc receptor-like B | Hs.517422 | -1.62 | 0.7 | |
| 154 | 212141_at, 212142_at, 222036_s_at, 222037_at | MCM4 | minichromosome maintenance complex component 4 | Hs.460184 | -1.61 | 0.7 | |
| 191 | 229490_s_at | --- | --- | Hs.133294 | -1.57 | 0.7 | |
| 192 | 1563137_at, 238445_x_at | MGAT5B | mannosyl (alpha-1,6-)-glycoprotein beta-1,6-N-acetyl-glucosaminyltransferase, isozyme B | Hs.144531 | -1.56 | 0.7 | |
| 208 | 204603_at | EXO1 | exonuclease 1 | Hs.498248 | -1.54 | 0.7 | M Phase |
| 214 | 219926_at | POPDC3 | popeye domain containing 3 | Hs.458336 | -1.54 | 0.7 | |
| 229 | 225203_at | PPP1R16A | protein phosphatase 1, regulatory (inhibitor) subunit 16A | Hs.521937 | -1.53 | 0.7 | |
| 234 | 202314_at, 216607_s_at | CYP51A1 | cytochrome P450, family 51, subfamily A, polypeptide 1 | Hs.417077 | -1.52 | 0.7 | |

FIGURE 6 (continued)

| | | | | | | |
|---|---|---|---|---|---|---|
| 235 | 201870_at | TOMM34 | translocase of outer mitochondrial membrane 34 | Hs.517066 | -1.52 | 0.7 | |
| 243 | 235736_at | --- | --- | Hs.178144 | -1.51 | 0.7 | |
| 246 | 204033_at | TRIP13 | thyroid hormone receptor interactor 13 | Hs.436187 | -1.51 | 0.7 | |
| 6 | 234180_at | --- | --- | Hs.540997 | -3.40 | 0.8 | |
| 88 | 1554474_a_at, 209708_at, 243697_at | MOXD1 | monooxygenase, DBH-like 1 | Hs.6909 | -1.77 | 0.8 | |
| 93 | 223805_at, 236261_at, 238575_at | OSBPL6 | oxysterol binding protein-like 6 | Hs.318775 | -1.75 | 0.8 | |
| 107 | 219898_at, 234303_s_at | GPR85 | G protein-coupled receptor 85 | Hs.152009 | -1.71 | 0.8 | |
| 123 | 230312_at | --- | --- | Hs.88045 | -1.67 | 0.8 | |
| 198 | 1557154_at, 1557155_a_at, 241440_at | FLJ30375 | Hypothetical gene supported by AK054937 | Hs.535724 | -1.56 | 0.8 | |
| 228 | 1561082_at, 202007_at, 202008_s_at | NID1 | nidogen 1 | Hs.356624 | -1.53 | 0.8 | |
| 239 | 200737_at, 227068_at, 217383_at, 217356_s_at, 200738_s_at | PGK1 | phosphoglycerate kinase 1 | Hs.78771 | -1.52 | 0.8 | |
| 242 | 1552619_a_at, 222608_s_at | ANLN | anillin, actin binding protein | Hs.62180 | -1.51 | 0.8 | M Phase |
| 2 | 1568878_at | --- | --- | Hs.531359 | -6.90 | 1.2 | |

FIGURE 6 (continued)

| 56 | 208514_at, 236407_at | KCNE1 | potassium voltage-gated channel, Isk-related family, member 1 | Hs.121495 | -1.95 | 1.2 | |
|---|---|---|---|---|---|---|---|
| 61 | 235334_at | ST6GALNAC3 | ST6 (alpha-N-acetyl-neuraminyl-2,3-beta-galactosyl-1,3)-N-acetylgalactosaminide alpha-2,6-sialyltransferase 3 | Hs.337040 | -1.92 | 1.2 | |
| 163 | 1554403_a_at | --- | --- | Hs.553957 | -1.60 | 1.2 | |
| 182 | 202223_at | STT3A | STT3, subunit of the oligosaccharyltransferase complex, homolog A (S. cerevisiae) | Hs.504237 | -1.58 | 1.2 | |
| 213 | 244479_at | --- | --- | Hs.126664 | -1.54 | 1.2 | |
| 217 | 204727_at, 204728_s_at, 216228_s_at | WDHD1 | WD repeat and HMG-box DNA binding protein 1 | Hs.385998 | -1.54 | 1.2 | |
| 12 | 237731_at | LOC154092 | hypothetical protein LOC154092 | Hs.223718 | -2.59 | 1.4 | |
| 262 | 227165_at | C13orf3 | chromosome 13 open reading frame 3 | Hs.88523 | -1.49 | 1.4 | |
| 73 | 220892_s_at, 223062_s_at | PSAT1 | phosphoserine aminotransferase 1 | Hs.494261 | -1.84 | 1.6 | Cofactor Binding |
| 87 | 1562475_at, 216877_at, 216874_at | DKFZp686O1327 | hypothetical gene supported by BC043549; BX648102 | Hs.42192 | -1.78 | 1.6 | |

FIGURE 6 (continued)

| | | | | | | |
|---|---|---|---|---|---|---|
| 127 | 235572_at | SPC24 | SPC24, NDC80 kinetochore complex component, homolog (S. cerevisiae) | Hs.381225 | -1.66 | 1.6 | M Phase |
| 164 | 207329_at | MMP8 | matrix metallopeptidase 8 (neutrophil collagenase) | Hs.161839 | -1.60 | 1.6 | |
| 43 | 206651_s_at | CPB2 | carboxypeptidase B2 (plasma) | Hs.512937 | -2.05 | 1.7 | |
| 74 | 1559462_at | --- | --- | Hs.446446 | -1.83 | 1.7 | |
| 85 | 1558522_at | --- | --- | Hs.594275 | -1.78 | 1.7 | |
| 149 | 206256_at | CPN1 | carboxypeptidase N, polypeptide 1 | Hs.2246 | -1.62 | 1.7 | |
| 220 | 221008_s_at | AGXT2L1 | alanine-glyoxylate aminotransferase 2-like 1 | Hs.106576 | -1.54 | 1.7 | Cofactor Binding |
| 13 | 220245_at, 221644_s_at | SLC45A2 | solute carrier family 45, member 2 | Hs.278962 | -2.46 | 1.9 | |
| 42 | 215079_at | --- | --- | Hs.612917 | -2.05 | 1.9 | |
| 72 | 208590_x_at, 239572_at | GJA3 | gap junction protein, alpha 3, 46kDa | Hs.130313 | -1.85 | 1.9 | |
| 80 | 238219_at | C12orf50 | chromosome 12 open reading frame 50 | Hs.112930 | -1.80 | 2.1 | |
| 100 | 209294_x_at, 209295_at, 210405_x_at | TNFRSF10B | tumor necrosis factor receptor superfamily, member 10b | Hs.521456 | -1.73 | 2.1 | |

FIGURE 6 (continued)

| | | | | | |
|---|---|---|---|---|---|
| 144 | 239922_at | CCDC142 | coiled-coil domain containing 142 | Hs.430199 | -1.63 | 2.1 | |
| 157 | 205598_at | TRAIP | TRAF interacting protein | Hs.517972 | -1.61 | 2.1 | |
| 165 | 203393_at, 203394_s_at, 203395_s_at | HES1 | hairy and enhancer of split 1, (Drosophila) | Hs.250666 | -1.60 | 2.1 | |
| 174 | 205543_at | HSPA4L | heat shock 70kDa protein 4-like | Hs.135554 | -1.59 | 2.1 | |
| 199 | 205048_s_at, 205194_at, 244819_x_at | PSPH | phosphoserine phosphatase | Hs.512656 | -1.56 | 2.1 | |
| 207 | 206141_at | MOCS3 | molybdenum cofactor synthesis 3 | Hs.159410 | -1.55 | 2.1 | |
| 8 | 210072_at | CCL19 | chemokine (C-C motif) ligand 19 | Hs.50002 | 2.75 | 2.5 | Immune system process; cells expressing leukocytes |
| 33 | 240068_at | C21orf130 | chromosome 21 open reading frame 130 | Hs.106234 | -2.15 | 2.5 | |
| 39 | 205085_at | ORC1L | origin recognition complex, subunit 1-like (yeast) | Hs.17908 | -2.08 | 2.5 | |
| 46 | 1555292_at, 231880_at | FAM40B | family with sequence similarity 40, member B | Hs.489988 | -2.02 | 2.5 | |
| 64 | 202523_s_at, 202524_s_at | SPOCK2 | sparc/osteonectin, cwcv and kazal-like domains proteoglycan (testican) 2 | Hs.523009 | 1.90 | 2.5 | |
| 89 | 233767_at | --- | --- | Hs.636837 | 1.77 | 2.5 | |

FIGURE 6 (continued)

| | | | | | |
|---|---|---|---|---|---|
| 92 | 243154_at | --- | --- | Hs.86650 | 1.76 | 2.5 | |
| 96 | 1560100_at, 242138_at | DLX1 | distal-less homeobox 1 | Hs.407015 | -1.74 | 2.5 | |
| 103 | 206660_at | IGLL1 | immunoglobulin lambda-like polypeptide 1 | Hs.348935 | 1.72 | 2.5 | Immune system process; cells expressing B cells |
| 104 | 1569510_at | --- | --- | Hs.621242 | 1.72 | 2.5 | |
| 106 | 1570268_at | --- | --- | Hs.518877 | 1.71 | 2.5 | |
| 116 | 1561899_at, 244413_at | CLECL1 | C-type lectin-like 1 | Hs.560087 | 1.69 | 2.5 | |
| 146 | 239579_at | ABHD7 | abhydrolase domain containing 7 | Hs.201555 | -1.63 | 2.5 | |
| 155 | 208694_at, 210543_s_at, 215757_at | PRKDC | protein kinase, DNA-activated, catalytic polypeptide | Hs.491682 | -1.61 | 2.5 | |
| 183 | 1561737_at | --- | --- | Hs.573815 | 1.58 | 2.5 | |
| 195 | 230423_at | --- | --- | Hs.120204 | -1.56 | 2.5 | |
| 202 | 241483_at | --- | --- | Hs.62772 | 1.55 | 2.5 | |
| 236 | 1552623_at | HSH2D | hematopoietic SH2 domain containing | Hs.631617 | 1.52 | 2.5 | Immune system process; cells expressing T cells; mediates signaling through TCR and CD28 |
| 258 | 218984_at | PUS7 | pseudouridylate synthase 7 homolog (S. cerevisiae) | Hs.520619 | -1.49 | 2.5 | |
| 3 | 205113_at | NEFM | neurofilament, medium polypeptide 150kDa | Hs.458657 | -4.20 | 2.8 | |

FIGURE 6 (continued)

| 31 | 217549_at | --- | --- | Hs.527860 | 2.18 | 2.8 | |
|---|---|---|---|---|---|---|---|
| 48 | 236295_s_at | NLRC3 | NLR family, CARD domain containing 3 | Hs.592091 | 2.00 | 2.8 | Immune system process; cells expressing T cells; NOD3 |
| 101 | 227055_at | METTL7B | methyltransferase like 7B | Hs.51483 | -1.73 | 2.8 | |
| 113 | 220485_s_at | SIRPG | signal-regulatory protein gamma | Hs.590883 | 1.69 | 2.8 | Immune system process; cells expressing T cells; CD172g |
| 119 | 238504_at | C6orf57 | chromosome 6 open reading frame 57 | Hs.418495 | -1.68 | 2.8 | |
| 125 | 230874_at | --- | | Hs.596383 | -1.67 | 2.8 | |
| 130 | 1554717_a_at, 204491_at, 210836_x_at, 210837_s_at, 211840_s_at, 228962_at | PDE4D | phosphodiesterase 4D, cAMP-specific (phosphodiesterase E3 dunce homolog, Drosophila) | Hs.117545 | -1.66 | 2.8 | |
| 160 | 227051_at | --- | | Hs.43047 | -1.60 | 2.8 | |
| 178 | 204265_s_at, 214847_s_at | GPSM3 | G-protein signaling modulator 3 (AGS3-like, C. elegans) | Hs.520046 | 1.59 | 2.8 | Immune system process; cells expressing not clear |
| 203 | 1562997_a_at | --- | | Hs.436357 | -1.55 | 2.8 | |
| 219 | 208050_s_at, 209811_at, 209812_x_at, 211140_s_at, 226032_at, 226036_x_at, 34449_at | CASP2 | caspase 2, apoptosis-related cysteine peptidase (neural precursor cell expressed, developmentally down-regulated 2) | Hs.368982 | -1.54 | 2.8 | |

FIGURE 6 (continued)

| 227 | 1557370_s_at | MYCBP2 | MYC binding protein 2 | Hs.591221 | 1.53 | 2.8 | |
| --- | --- | --- | --- | --- | --- | --- | --- |
| 134 | 201960_s_at, 201959_s_at 223625_at, 227239_at, 231396_s_at, 244115_at | FAM126A | family with sequence similarity 126, member A | Hs.85603 | -1.65 | 3.2 | |
| 171 | 204252_at, 211803_at, 211804_s_at | CDK2 | cyclin-dependent kinase 2 | Hs.19192 | -1.59 | 3.2 | M Phase |
| 173 | 205519_at | WDR76 | WD repeat domain 76 | Hs.250154 | -1.59 | 3.2 | |
| 188 | 239509_at | --- | --- | Hs.111539 | -1.57 | 3.2 | |
| 218 | 205195_at, 205196_s_at, 209635_at | AP1S1 | adaptor-related protein complex 1, sigma 1 subunit | Hs.563509 | -1.54 | 3.2 | |

FIGURE 7

Table 3 (TOP 50 GENES)

| Probe # | AFFY ID(s) | Gene Symbol | Gene Title | UniGene ID | FC | q-value (%) | Top Functional Gene Category (DAVID) |
|---|---|---|---|---|---|---|---|
| 59 | 243175_at | UTS2D | urotensin 2 domain containing | Hs.518492 | -1.93 | 0.0 | |
| 112 | 241790_at | --- | --- | Hs.385861 | -1.69 | 0.0 | |
| 156 | 218039_at, 219978_s_at | NUSAP1 | nucleolar and spindle associated protein 1 | Hs.615092 | -1.61 | 0.0 | M Phase |
| 162 | 219148_at | PBK | PDZ binding kinase | Hs.104741 | -1.60 | 0.0 | M Phase |
| 187 | 218782_s_at, 222740_at, 228401_at, 235266_at | ATAD2 | ATPase family, AAA domain containing 2 | Hs.370834 | -1.57 | 0.0 | |
| 253 | 219556_at | C16orf59 | chromosome 16 open reading frame 59 | Hs.534491 | -1.50 | 0.0 | |
| 261 | 1554540_at, 242283_at | DNAH14 | dynein, axonemal, heavy chain 14 /// chromosome 1 open reading frame 67 /// similar to CG7092-PA | Hs.133977 | -1.49 | 0.0 | |
| 264 | 235949_at | --- | --- | Hs.133020 | -1.49 | 0.0 | |
| 1 | 236967_at | LOC645249 | hypothetical protein LOC645249 | Hs.224879 | -14.34 | 0.7 | |
| 50 | 222346_at, 227048_at | LAMA1 | laminin, alpha 1 | Hs.270364 | -1.99 | 0.7 | |

FIGURE 7 (continued)

| | | | | | |
|---|---|---|---|---|---|
| 68 | 217640_x_at | C18orf24 | chromosome 18 open reading frame 24 | Hs.134726 | -1.86 | 0.7 | M Phase |
| 97 | 228262_at | MAP7D2 | MAP7 domain containing 2 | Hs.127951 | -1.74 | 0.7 | |
| 110 | 203440_at, 203441_s_at | CDH2 | cadherin 2, type 1, N-cadherin (neuronal) | Hs.464829 | -1.71 | 0.7 | |
| 152 | 238452_at | FCRLB | Fc receptor-like B | Hs.517422 | -1.62 | 0.7 | |
| 154 | 212141_at, 212142_at, 222036_s_at, 222037_at | MCM4 | minichromosome maintenance complex component 4 | Hs.460184 | -1.61 | 0.7 | |
| 191 | 229490_s_at | --- | --- | Hs.133294 | -1.57 | 0.7 | |
| 192 | 1563137_at, 238445_x_at | MGAT5B | mannosyl (alpha-1,6-)-glycoprotein beta-1,6-N-acetyl-glucosaminyltransferase, isozyme B | Hs.144531 | -1.56 | 0.7 | |
| 208 | 204603_at | EXO1 | exonuclease 1 | Hs.498248 | -1.54 | 0.7 | M Phase |
| 214 | 219926_at | POPDC3 | popeye domain containing 3 | Hs.458336 | -1.54 | 0.7 | |
| 229 | 225203_at | PPP1R16A | protein phosphatase 1, regulatory (inhibitor) subunit 16A | Hs.521937 | -1.53 | 0.7 | |
| 234 | 202314_at, 216607_s_at | CYP51A1 | cytochrome P450, family 51, subfamily A, polypeptide 1 | Hs.417077 | -1.52 | 0.7 | |
| 235 | 201870_at | TOMM34 | translocase of outer mitochondrial membrane 34 | Hs.517066 | -1.52 | 0.7 | |
| 243 | 235736_at | --- | --- | Hs.178144 | -1.51 | 0.7 | |

FIGURE 7 (continued)

| | | | | | | |
|---|---|---|---|---|---|---|
| 246 | 204033_at | TRIP13 | thyroid hormone receptor interactor 13 | Hs.436187 | -1.51 | 0.7 |
| 6 | 234180_at | --- | --- | Hs.540997 | -3.40 | 0.8 |
| 88 | 1554474_a_at, 209708_at, 243697_at | MOXD1 | monooxygenase, DBH-like 1 | Hs.6909 | -1.77 | 0.8 |
| 93 | 223805_at, 236261_at, 238575_at | OSBPL6 | oxysterol binding protein-like 6 | Hs.318775 | -1.75 | 0.8 |
| 107 | 219898_at, 234303_s_at | GPR85 | G protein-coupled receptor 85 | Hs.152009 | -1.71 | 0.8 |
| 123 | 230312_at | --- | --- | Hs.88045 | -1.67 | 0.8 |
| 198 | 1557154_at, 1557155_a_at, 241440_at | FLJ30375 | Hypothetical gene supported by AK054937 | Hs.535724 | -1.56 | 0.8 |
| 228 | 1561082_at, 202007_at, 202008_s_at | NID1 | nidogen 1 | Hs.356624 | -1.53 | 0.8 |
| 239 | 200737_at, 227068_at, 217383_at, 217356_s_at, 200738_s_at | PGK1 | phosphoglycerate kinase 1 | Hs.78771 | -1.52 | 0.8 |
| 242 | 1552619_a_at, 222608_s_at | ANLN | anillin, actin binding protein | Hs.62180 | -1.51 | 0.8 | M Phase |
| 2 | 1568878_at | --- | --- | Hs.531359 | -6.90 | 1.2 |
| 56 | 208514_at, 236407_at | KCNE1 | potassium voltage-gated channel, Isk-related family, member 1 | Hs.121495 | -1.95 | 1.2 |

FIGURE 7 (continued)

| | | | | | |
|---|---|---|---|---|---|
| 61 | 235334_at | ST6GALNA C3 | ST6 (alpha-N-acetyl-neuraminyl-2,3-beta-galactosyl-1,3)-N-acetylgalactosaminide alpha-2,6-sialyltransferase 3 | Hs.337040 | -1.92 | 1.2 | |
| 163 | 1554403_a_at | --- | --- | Hs.553957 | -1.60 | 1.2 | |
| 182 | 202223_at | STT3A | STT3, subunit of the oligosaccharyltransferase complex, homolog A (S. cerevisiae) | Hs.504237 | -1.58 | 1.2 | |
| 213 | 244479_at | --- | --- | Hs.126664 | -1.54 | 1.2 | |
| 217 | 204727_s_at, 204728_s_at, 216228_s_at | WDHD1 | WD repeat and HMG-box DNA binding protein 1 | Hs.385998 | -1.54 | 1.2 | |
| 12 | 237731_at | LOC154092 | hypothetical protein LOC154092 | Hs.223718 | -2.59 | 1.4 | |
| 262 | 227165_at | C13orf3 | chromosome 13 open reading frame 3 | Hs.88523 | -1.49 | 1.4 | |
| 73 | 220892_s_at, 223062_s_at | PSAT1 | phosphoserine aminotransferase 1 | Hs.494261 | -1.84 | 1.6 | Cofactor Binding |
| 87 | 1562475_at, 216877_at, 216874_at | DKFZp686O 1327 | hypothetical gene supported by BC043549; BX648102 | Hs.42192 | -1.78 | 1.6 | |
| 127 | 235572_at | SPC24 | SPC24, NDC80 kinetochore complex component, homolog (S. cerevisiae) | Hs.381225 | -1.66 | 1.6 | M Phase |

FIGURE 7 (continued)

| 164 | 207329_at | MMP8 | matrix metallopeptidase 8 (neutrophil collagenase) | Hs.161839 | -1.60 | 1.6 |
|---|---|---|---|---|---|---|
| 43 | 206651_s_at | CPB2 | carboxypeptidase B2 (plasma) | Hs.512937 | -2.05 | 1.7 |
| 74 | 1559462_at | --- | --- | Hs.446446 | -1.83 | 1.7 |
| 85 | 1558522_at | --- | --- | Hs.594275 | -1.78 | 1.7 |

FIGURE 8

Table 4

| Probe # | AFFY ID(s) | Gene Symbol | Gene Title | UniGene ID | FC | q-value (%) | Top Functional Gene Category (DAVID) |
|---|---|---|---|---|---|---|---|
| 1 | 236967_at | LOC645249 | hypothetical protein LOC645249 | Hs.224879 | -14.34 | 0.7 | |
| 8 | 210072_at | CCL19 | chemokine (C-C motif) ligand 19 | Hs.50002 | 2.75 | 2.5 | Immune system process; cells expressing leukocytes |
| 103 | 206660_at | IGLL1 | immunoglobulin lambda-like polypeptide 1 | Hs.348935 | 1.72 | 2.5 | Immune system process; cells expressing B cells |
| 3 | 205113_at | NEFM | neurofilament, medium polypeptide 150kDa | Hs.458657 | -4.20 | 2.8 | |
| 154 | 212141_at, 212142_at, 222036_s_at, 222037_at | MCM4 | minichromosome maintenance complex component 4 | Hs.460184 | -1.61 | 0.7 | |
| 48 | 236295_s_at | NLRC3 | NLR family, CARD domain containing 3 | Hs.592091 | 2.00 | 2.8 | Immune system process; cells expressing T cells; NOD3 |
| 5 | 205242_at | CXCL13 | chemokine (C-X-C motif) ligand 13 (B-cell chemoattractant) | Hs.100431 | 3.93 | 3.6 | Immune system process; cells expressing leukocytes; BCA-1, B-cell chemoattractant |
| 17 | 206337_at | CCR7 | chemokine (C-C motif) receptor 7 | Hs.370036 | 2.37 | 3.6 | Response to stimulus; cells expressing leukocytes; CD197 |
| 26 | 205831_at | CD2 | CD2 molecule | Hs.523500 | 2.26 | 3.6 | Immune system process; cells expressing T cells |
| 27 | 206150_at | CD27 | CD27 molecule | Hs.355307 | 2.24 | 3.6 | Immune system process; cells expressing T cells |
| 32 | 1559754_at, 207339_s_at | LTB | Lymphotoxin beta (TNF superfamily, member 3) | Hs.376208 | 2.16 | 3.6 | Immune system process; cells expressing leukocytes |
| 34 | 1555779_a_at, 205049_s_at | CD79A | CD79a molecule, immunoglobulin-associated alpha | Hs.631567 | 2.13 | 3.6 | Immune system process; cells expressing B cells |

FIGURE 8 (continued)

| 54 | 1553856_s_at, 214615_at | P2RY10 | purinergic receptor P2Y, G-protein coupled, 10 | Hs.296433 | 1.96 | 3.6 | Cell communication; cells expressing leukocytes |
|---|---|---|---|---|---|---|---|
| 6 | 234180_at | --- | --- | Hs.540997 | -3.40 | 0.8 | |
| 113 | 220485_s_at | SIRPG | signal-regulatory protein gamma | Hs.590883 | 1.69 | 2.8 | Immune system process; cells expressing T cells; CD172g |
| 14 | 213539_at | CD3D | CD3d molecule, delta (CD3-TCR complex) | Hs.504048 | 2.44 | 4.8 | Immune system process; cells expressing T cells |
| 7 | 223750_s_at, 223751_x_at | TLR10 | toll-like receptor 10 | Hs.120551 | 2.91 | 4.2 | Immune system process; cells expressing leukocytes |

FIGURE 9

Table 5

| Affy ID | Gene Symbol | Gene Title | Entrez Gene ID | UniGene ID |
|---|---|---|---|---|
| 235949_at | --- | --- | --- | Hs.133020 |
| 215998_at | --- | --- | --- | Hs.155959 |
| 207734_at | LAX1 | lymphocyte transmembrane adaptor 1 | 54900 | Hs.272794 |
| 201115_at | POLD2 | polymerase (DNA directed), delta 2, regulatory subunit 50kDa | 5425 | Hs.306791 |
| 241790_at | --- | --- | --- | Hs.385861 |
| 1559462_at | --- | --- | --- | Hs.446446 |
| 206895_at, 211169_s_at | PPP1R3A | protein phosphatase 1, regulatory (inhibitor) subunit 3A | 5506 | Hs.458309 |
| 225687_at | FAM83D | family with sequence similarity 83, member D | 81610 | Hs.472716 |
| 202094_at, 202095_s_at, 210334_x_at | BIRC5 | baculoviral IAP repeat-containing 5 | 332 | Hs.514527 |
| 243175_at | UTS2D | urotensin 2 domain containing | 257313 | Hs.518492 |
| 1570268_at | --- | --- | --- | Hs.518877 |
| 219556_at | C16orf59 | chromosome 16 open reading frame 59 | 80178 | Hs.534491 |
| 1561899_at, 244413_at | CLECL1 | C-type lectin-like 1 | 160365 | Hs.560087 |
| 1557370_s_at, 201959_s_at, 201960_s_at | MYCBP2 | MYC binding protein 2 | 23077 | Hs.591221 |
| 1569510_at | --- | --- | --- | Hs.621242 |
| 241483_at | --- | --- | --- | Hs.62772 |
| 1552623_at | HSH2D | hematopoietic SH2 domain containing | 84941 | Hs.631617 |
| 233767_at | --- | --- | --- | Hs.636837 |
| 243154_at | --- | --- | --- | Hs.86650 |
| 1558626_at | --- | --- | --- | Hs.98028 |

METHODS FOR PREDICTING SURVIVAL IN METASTATIC MELANOMA PATIENTS

CROSS REFERENCE TO RELATED APPLICATIONS

This application claims priority under 35 USC §119(e) from U.S. Provisional Application Ser. No. 61/305,870, filed Feb. 18, 2010, which application is herein specifically incorporated by reference in its entirety.

GOVERNMENT SUPPORT

The research leading to the present inventions was funded in part by Grant Nos. P30 CA016087-29 and R37 AI044628 from the National Institutes of Health, and Grant No. IIS-0447773 from the National Science Foundation. The government has certain rights in the invention.

FIELD OF THE INVENTION

The present invention relates to indicators that can guide clinical decisions in treatment and prognosis of patients with metastatic melanoma. More particularly, methods and indicators are described herein that are useful in subcategorizing stage III melanoma tumors. The methods and indicators are particularly useful with regard to establishing more distinct criteria on which basis to differentiate stage IIIB and IIIC melanoma patients. Such indicators may be used as predictive of differential survival, prognosis and sensitivity to targeted cancer therapy. As described herein, gene expression profiling, determination of mitotic index (MI), and quantification of tumor infiltrating leukocytes (TILs) and CD3+ cells in metastatic lesions may be utilized to predict or assess drug response, drug sensitivity, and clinical outcome in metastatic melanoma patients.

BACKGROUND OF THE INVENTION

Melanoma is the deadliest form of skin cancer, and its incidence is on the rise (1-3). Treatment options for advanced melanoma are limited and rarely curative. While 5 year survival for stage III melanoma patients can reach up to 69% depending on the patient subcategory, the reported survival for stage IV disease is rarely longer than a year (3). Although long-term survival for patients with advanced melanoma is low despite currently available therapies, some patients can survive for prolonged periods with metastatic disease. The ability to predict survival in metastatic melanoma with greater accuracy could improve current treatment decisions and aid in the design of new therapies that might be tailored to specific subgroups of patients. The majority of innovative and improved prediction models, however, are geared toward evaluating the metastatic potential of primary tumors, as opposed to evaluating the progression potential of metastatic disease. It would potentially be useful to biologically subclassify melanoma that has already metastasized, beyond the use of the conventional Tumor, Node, Metastasis (TNM) staging, into categories that more accurately predict patient survival (4).

Many studies have shown the importance of the immune response in the equilibrium state of primary neoplasia but very few evidenced its importance in managing metastasis [Piras et al. (2005) Cancer 104: 1246-1254]. Both predictive potential and novelty of findings especially associated with immune regulation as well as proliferation suggest necessity of further development of this approach [Francken et al. (2004) Ann Surg Oncol 11: 426-433]. Presence of leukocytes within the lesions as an easy and highly predictive tool of patient prognosis has not been sufficiently explored, possibly due to the conflicting studies that show both beneficial and detrimental effects [Piras et al. (2005) Cancer 104: 1246-1254; Sato et al. (2005) Proc Natl Acad Sci USA 102: 18538-18543; Galon et al. (2006) Science 313: 1960-1964]. Establishing evidence of inflammation at the molecular and cellular level in the lesions is crucial for advancement of immunotherapies in melanoma. There is a need to characterize in detail the immune regulatory molecules that are associated with the increased survival since immunotherapy could be utilized to further boost an already beneficial molecular sub profile.

The citation of references herein shall not be construed as an admission that such is prior art to the present invention.

SUMMARY OF THE INVENTION

In a general aspect, the present invention relates to predicting survival in a patient with metastatic melanoma. More particularly, the invention relates to the discovery that the Mitotic Index (MI), the molecular or genetic signature, and levels of CD3+ cells and tumor infiltrating lymphocytes (TILS) of a metastatic melanoma sample isolated from a patient can be used as predictive indicators of survival duration for patients with metastatic melanoma and, moreover, can be used to design and select therapeutic regimens tailored to the molecular and cellular signature of metastatic melanoma.

In an aspect of the invention, a method for predicting survival or response to a therapeutic regimen in a patient with Stage IIIB or Stage IIIC melanoma is described, the method comprising: a) isolating a melanoma sample from the patient; and b) determining a mitotic index for the melanoma sample, wherein a low mitotic index is correlated with increased duration of survival or a positive response to a first therapeutic regimen in the patient and a high mitotic index is correlated with decreased duration of survival and a positive response to a second therapeutic regimen in the patient.

In an embodiment of the method, the low mitotic index is equivalent to less than 0.75 mitoses per high power field. As described herein, a high power field equals 0.196 mm$^2$.

In yet another embodiment of the method, the first therapeutic regimen promotes immune response in the patient.

In a further embodiment of the method, the second therapeutic regimen inhibits cell proliferation in the patient.

In another aspect of the invention, a method for predicting survival or response to a therapeutic regimen in a patient with Stage IIIB or Stage IIIC melanoma is described, the method comprising: a) isolating a melanoma sample from the patient; and b) determining the number of CD3+ cells in the melanoma sample, wherein an elevated number of CD3+ cells is correlated with increased duration of survival or a positive response to the therapeutic regimen in the patient.

In an embodiment of the method, the elevated number of CD3+ cells is higher than 80 CD3+ cells per 10 high power fields.

In a further embodiment, the therapeutic regimen promotes immune response in the patient.

In another aspect, a method for predicting survival in a patient with melanoma is described, the method comprising: a) isolating a melanoma sample from the patient; and b) determining expression of genes listed in Table 5 in the melanoma sample to generate a genetic signature for the melanoma sample, wherein detection of a genetic signature that matches the expression pattern of at least 6 of the genes listed in Table 5 is correlated with survival in the patient. Detection of a genetic signature indicative of an active immune response (i.e., an immune response genetic signature) is correlated with increased duration of survival and clinical responsiveness to immune therapy. Detection of a genetic signature indicative of low levels of cell proliferation is also correlated with increased duration of survival. In contrast, detection of a genetic signature indicative of cellular proliferation (i.e., a proliferative genetic signature) is correlated with decreased duration of survival and clinical responsiveness to therapeutic approaches that target proliferating cells, such as chemotherapy. In an embodiment thereof, the method further comprises determining a mitotic index for the melanoma sample, wherein a low mitotic index is correlated with increased duration of survival in the patient, whereas a high mitotic index is correlated with decreased duration of survival.

In a particular embodiment, the patient with melanoma has Stage IIIB or Stage IIIC melanoma.

In a further embodiment of the method, the melanoma sample has a genetic signature that matches at least 10 of the genes listed in Table 5; at least 15 of the genes listed in Table 5; at least 20 of the genes listed in Table 5; or all 21 of the genes listed in Table 5. Indeed, the method encompasses detection of a genetic signature that matches each whole integer from 6 to all 21 of the genes of Table 5, wherein detection of same is correlated with survival in the patient and predictive of response to various therapeutic regimens as described herein.

The expression level of the genes may be determined using a variety of techniques known in the art. In one embodiment, the expression level of the genes is determined using a microarray. In another embodiment, the expression level of the genes is determined using a method of RNA quantitation.

Methods described herein may further comprise determining the number of tumor infiltrating leukocytes (TILs) in the melanoma sample, wherein a high number of TILs is correlated with enhanced duration of survival in the patient or a positive response to a therapeutic regimen in the patient. In keeping with guidance presented herein, a high number of TILs is equivalent to TILs comprising >50% of tumor area in the melanoma sample. In an embodiment thereof, the therapeutic regimen promotes immune response in the patient.

Also encompassed herein is a method for predicting survival or response to a therapeutic regimen in a patient with Stage IIIB or Stage IIIC melanoma, said method comprising: a) isolating a melanoma sample from the patient; and b) determining expression of genes listed in any one of Table 1, Table 2, Table 3 or Table 4 in the melanoma sample, wherein detecting expression levels of at least six genes associated with either immune response or cell proliferation is correlated with duration of survival in the mammal and a positive response to a therapeutic regimen in the patient. As described herein, elevated expression levels of genes characteristic of active immune response and reduced expression levels of genes associated with cell proliferation are positively correlated with increased duration of survival in a mammal and predict that the mammal will respond favorably to therapy that promotes or activates immune response in the mammal. Increased or elevated levels of genes associated with cell proliferation are correlated with reduced duration of survival in the mammal and predict that the mammal will respond favorably to therapy that inhibits cellular proliferation in the mammal. In accordance with the methods presented herein, expression levels are calculated and may be expressed relative to a reference.

In another aspect, a method for predicting survival or response to a therapeutic regimen in a mammal with Stage IIIC melanoma is presented, the method comprising: a) isolating a melanoma sample from the patient; and b) determining the number of tumor infiltrating leukocytes (TILs) in the melanoma sample, wherein an elevated number of TILs is correlated with increased duration of survival or a positive response to the therapeutic regimen in the mammal. In an embodiment of the method, the high number of TILs is equivalent to TILs comprising >50% of tumor area in the melanoma sample. In another embodiment, the therapeutic regimen promotes immune response in the patient.

As described herein, the melanoma sample may be a tumor biopsy or cancer cell sample isolated from the patient.

In an embodiment of the method described herein, the patient or subject is a mammal. In a particular embodiment, the mammal is a human.

The invention also provides compositions comprising one or more detection agents for detecting the expression of genes that are predictive of survival duration and response to various therapeutic regimens in mammals with melanoma. More particularly, compositions described herein are useful for predicting survival duration in Stage IIIB and Stage IIIC melanoma patients, and for predicting which therapeutic regimen would confer maximal benefit to such patients. Compositions described herein may also be used to assess efficacy of a therapeutic regimen for a melanoma patient by monitoring changes in gene expression. As described herein, increases in the expression of genes associated with ongoing immune response and decreases in expression of genes associated with cell proliferation (as presented in any one of Tables 1-5) may be used as positive indicators that the therapeutic regimen is efficacious. Accordingly, a composition comprising detection agents for detecting the expression of all of the genes listed in any one of Tables 1-5 is encompassed herein. Also encompassed herein, is a composition comprising detection agents for detecting a subset of the genes listed in any one of Tables 1-5. Compositions comprising detection agents for detecting the expression of at least 6, at least 10, at least 15, at least 20, at least 50, at least 100, at least 150, or at least 200 of the genes listed in any one of Tables 1-5 are envisioned. It is understood that with regard to each of Tables 1-5, the total number of genes listed therein varies, so compositions targeting a particular gene signature as set forth in any one of Tables 1-5 reflect the total number of genes listed therein and subsets thereof. In a particular embodiment, compositions comprising detection agents for detecting the expression of at least 6, at least 10, at least 15, at least 20, or all 21 of the genes listed in Table 5 are envisioned. Also encompassed are compositions comprising detection agents for detecting the expression of at least 6, at least 10, at least 15, at least 20, at least 25, at least 30, at least 35, at least 40, at least 45, or all 50 of the genes listed in Table 3. Detection agents, which may be, e.g., nucleic acids or polypeptides, maybe in solution or bound to a solid surface, such as in the form of a microarray. Other embodiments of the invention include databases, computer readable media, computers containing the gene expression profile(s) described herein.

Accordingly, encompassed herein is a composition for diagnosing survival duration and response to a therapeutic regimen in a mammal with Stage IIIB or Stage IIIC melanoma, the composition comprising detection agents for assaying expression of at least six genes listed in any one Tables 1-5 and a suitable buffer. In a particular embodiment, such a composition comprises detection reagents for assaying expression of all of the genes listed in any one of Tables 2-5.

The present invention further provides a kit comprising a library of gene expression detection agents and reagents for evaluating gene expression levels. For example, the expression level may be determined by providing a kit containing appropriate reagents and an appropriate microarray for evaluating the level of expression of genes listed in any one of Tables 1-5, or subsets thereof as described herein, in the melanoma sample isolated from a mammalian subject. In other embodiments, the invention provides a kit including compositions of the present invention, and optionally instructions for their use. Such kits may have a variety of uses, including, for example, prediction of survival duration, choice of therapy, evaluation of efficacy of a therapy, and other applications, particularly with regard to Stage IIIB and Stage IIIC melanoma patients.

Accordingly, encompassed herein is a kit for diagnosing survival duration and response to a therapeutic regimen in a mammal with Stage IIIB or Stage IIIC melanoma, the kit comprising detection agents for assaying expression of at least six genes listed in any one Tables 1-5 and optionally, an instruction manual. In a particular embodiment, a kit comprises detection agents for assaying expression of all of the genes listed in Table 3, Table 4, or Table 5.

Other objects and advantages will become apparent to those skilled in the art from a review of the ensuing detailed description, which proceeds with reference to the following illustrative drawings, and the attendant claims.

BRIEF DESCRIPTION OF THE DRAWINGS

FIG. 5 presents a list of 266 genes that are significantly associated with post recurrence survival (Table 1).

FIG. 6 presents a list of 100 genes that are significantly associated with post recurrence survival (Table 2).

FIG. 7 presents a list of 50 genes that are significantly associated with post recurrence survival (Table 3).

FIG. 8 presents a list of 18 genes that are significantly associated with post recurrence survival (Table 4).

FIG. 9 presents a list of prevalidated gene predictors that are significantly associated with post recurrence survival (Table 5).

DETAILED DESCRIPTION

Figure 1:
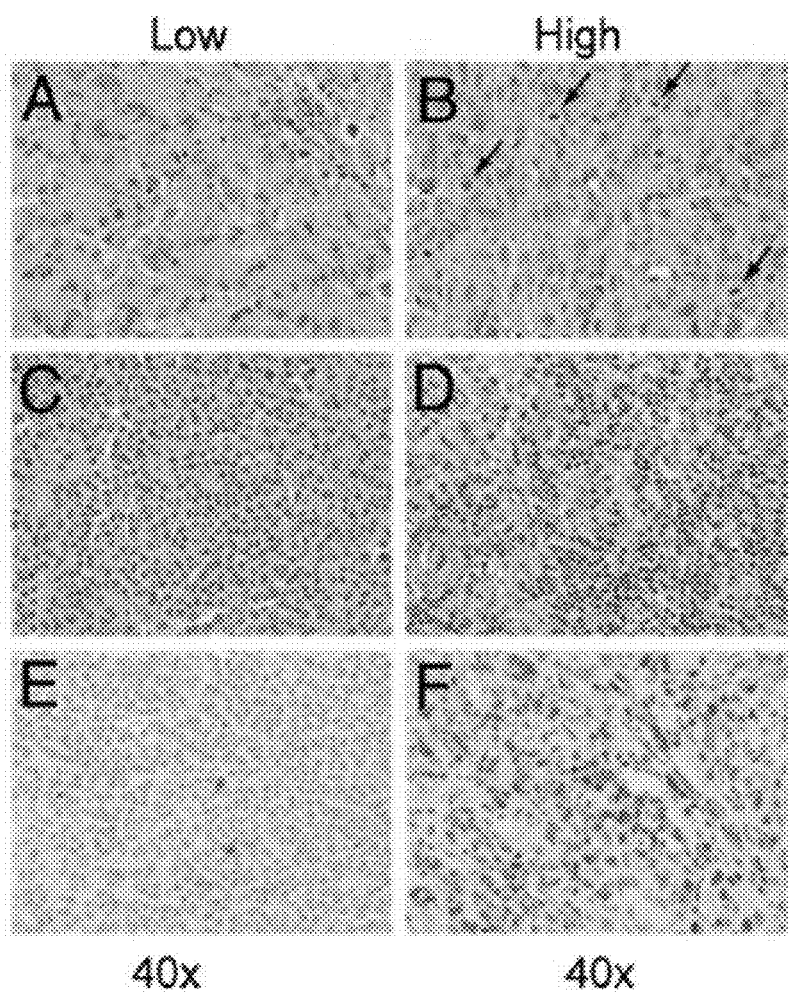
FIG. 1A-J shows that metastatic melanoma patient survival differs based on MI, TILs, and CD3 cell count. All available tissue specimens used for gene chip hybridization were also examined for the presence of mitoses; (A) reflects low and (B) reflects high levels of mitosis with bottom left corner showing a magnified section of the slide. Tissue specimens were also examined and scored for the presence of TILs. (C) shows a representative view of low and (D) shows a high level of TILs. Paraffin embedded samples were also stained for CD3; (E) shows low levels and (F) shows high levels of CD3+ cells present in the melanoma sample. Kaplan-Meier survival curves for groups based on MI (G, $P<0.0001$), TILs (H, $P=0.0163$), CD3 cell count (I, $P=0.0134$), and stage at recurrence/metastasis (J, overall $P=0.0006$, but the separation of Mb and IIIc is not significant $P=0.59$).
Figure 1:
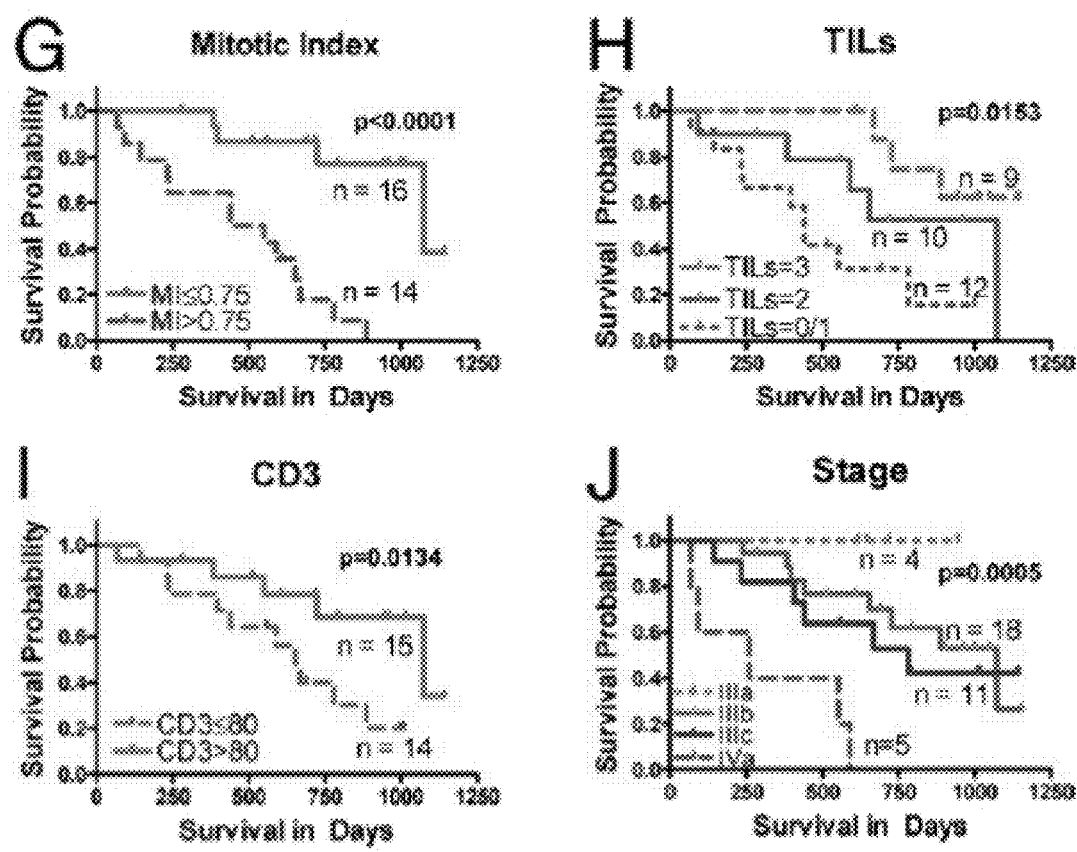

Although remission rates for metastatic melanoma are generally very poor, some patients can survive for prolonged periods following metastasis. The present inventors sought to investigate the molecular and cellular basis for this phenomenon by taking two complementary approaches: performing gene expression profiling of metastatic melanoma samples and classical immunohistochemistry.

The use of gene expression profiling has yielded an enormous amount of information leading to the definition of molecular signatures for a wide variety of tumor types (5-7). For breast cancer, gene expression profiles are already in use to classify tumors biologically in ways that impact decisions regarding the most appropriate form of treatment (8, 9). For melanoma, gene expression profiling has been used to establish molecular signatures of disease progression. This has been done by comparing normal skin to benign nevi and to primary and metastatic melanomas (10, 11). As described herein, the present inventors use gene expression profiling to define molecular signatures of different subsets of advanced melanoma associated with differing survival potential. The present inventors observe that increased expression of genes associated with immune response (relative to a reference) and decreased expression of genes associated with cell division (relative to a reference) are related to survival, and further explore the measurement of mitotic index (MI), tumor infiltrating leukocytes (TILs) and CD3+ cells in histologic sections of metastatic lesions as simple predictors of patient post-recurrence survival.

As described herein, the present inventors found a unique set of genes that differentiate among Stage IIIB and Stage IIIC melanoma patients who live longer as opposed to those who have relatively truncated lifespans. See, for example, Tables 1-5 (as depicted in FIGS. 5-9). The present inventors also discovered that determination of the mitotic index of a metastatic melanoma is an excellent method for evaluating survival potential. Use of a mitotic index as a predictor for survival in a patient with metastatic melanoma has not been described previously. More particularly, mitotic index has not been previously described as a predictor for survival in a patient diagnosed with Stage IIIB or Stage IIIC melanoma. Indeed, the results of Reddy et al. (J Cutan Pathol 22:248, 1995), for example, suggest that expression of cell proliferation markers does not appear to help predict prognosis in advanced level melanoma. Accordingly, the results presented herein are surprising in light of at least the findings of Reddy et al. The present inventors also demonstrate for the first time that the presence of certain immune parameters (e.g., CD3 cell count and TIL index) is linked to improved outcome in patients with metastatic melanoma. The TIL frequency is, for example, a significant predictor of survival in patients diagnosed with Stage IIIC melanoma. See, for example, FIG. 4D.

Accordingly, the present invention is directed in part to improved methods for predicting survival in patients with metastatic melanoma. The present findings also provide guidance on which basis patient populations can be selected for inclusion in clinical trials. Prior to the present invention, a clinical practitioner would have to evaluate patients on the basis of their disease stage and/or failure to respond to other therapies. The present criteria for parsing sub-populations from within the broader category of metastatic melanoma patients by gene expression profiling and/or evaluation of mitotic index and/or immune infiltrates will lead to improved patient selection for clinical trial and thus, lead in turn to more effective clinical trials.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A. TERMINOLOGY

The term "specific" may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

The term "comprise" generally used in the sense of include, that is to say permitting the presence of one or more features or components.

The term "consisting essentially of" refers to a product, particularly a peptide sequence, of a defined number of residues which is not covalently attached to a larger product. In the case of the peptide of the invention referred to above, those of skill in the art will appreciate that minor modifications to the N- or C-terminal of the peptide may however be contemplated, such as the chemical modification of the terminal to add a protecting group or the like, e.g. the amidation of the C-terminus.

The term "isolated" refers to the state in which specific binding members of the invention, or nucleic acid encoding such binding members will be, in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A DNA sequence is "operatively linked" to an expression control sequence when the expression control sequence controls and regulates the transcription and/or translation of that DNA sequence.

The term 'agent' means any molecule, including polypeptides, antibodies, polynucleotides, chemical compounds and small molecules. In particular the term agent includes compounds such as test compounds or drug candidate compounds.

The term 'agonist' refers to a ligand that stimulates the receptor the ligand binds to in the broadest sense.

The term 'assay' means any process used to measure a specific property of a compound. A 'screening assay' means a process used to characterize or select compounds based upon their activity from a collection of compounds.

The term 'preventing' or 'prevention' refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

'Therapeutically effective amount' means that amount of a drug, compound, or pharmaceutical agent that will elicit the biological or medical response of a subject that is being sought by a medical doctor or other clinician. The phrase "therapeutically effective amount" is used herein to mean an amount sufficient to reduce by at least about 30 percent, more preferably by at least 50 percent, most preferably by at least 90 percent, a clinically significant reduction in a symptom or symptoms associated with a disease or disorder.

The term 'treating' or 'treatment' of any disease or infection refers, in one embodiment, to ameliorating the disease or infection (i.e., arresting the disease or growth of the infectious agent or bacteria or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or infection, either physically, (e.g., stabilization of a discernible symptom), physiologically, (e.g., stabilization of a physical parameter), or both. In a further embodiment, 'treating' or 'treatment' relates to slowing the progression of a disease.

The phrase "pharmaceutically acceptable" refers to molecular entities and compositions that are physiologically tolerable and do not typically produce an allergic or similar untoward reaction, such as gastric upset, dizziness and the like, when administered to a human.

As used herein, "pg" means picogram, "ng" means nanogram, "ug" or "µg" mean microgram, "mg" means milligram, "ul" or "µl" mean microliter, "ml" means milliliter, "l" means liter.

As used herein, the term "melanoma" refers to a malignant tumor of melanocyte origin.

As used herein, the term "metastatic melanoma" refers to a melanoma, wherein melanoma cells have spread from the site of the primary melanoma tumor. In accordance with accepted nomenclature as set forth herein below and understood in the art, a subject or patient with metastatic melanoma would be classified as having Stage III or Stage IV melanoma.

As used herein, the term "biomarker" refers to a characteristic that is measured and evaluated as an indicator of normal biological processes, pathogenic processes or pharmacological responses (M. Danhof, Meeting Report, Markers of pharmacological and toxicological action, BioMedCentral, 2001).

As used herein, the term "prognostic biomarker" refers to a biomarker that is associated with a defined clinical outcome of an individual patient or group of patients, irrespective of whether or not the patient or group thereof are treated and irrespective of the type of therapy employed.

As used herein, the term "predictive biomarker" refers to a biomarker that predicts the clinical effect of a specific treatment.

As used herein, the term "proteomic biomarkers" refers to a protein expression pattern that is able to discriminate or predict.

As used herein, the term "increased duration of survival" refers to the propensity of a patient with a disease or condition to live longer than predicted compared to another patient diagnosed with the same disease or condition. With respect to the instant methods, in certain embodiments, the patient has had a Stage IIIB or Stage IIIC melanoma surgically resected (excised) and increased duration of survival of such a patient generally refers to the likelihood that the patient will live about 1.5 years or longer after surgical resection of the Stage IIIB or Stage IIIC melanoma.

As used herein, the term "decreased or reduced duration of survival" refers to the propensity of a patient with a disease or condition to die in a shorter period of time than predicted compared to another patient diagnosed with the same disease or condition. With respect to the instant methods, in certain embodiments, the patient has had a Stage IIIB or Stage IIIC melanoma surgically resected (excised) and decreased duration of survival of such a patient generally refers to the likelihood that the patient will live fewer than about 1.5 years (i.e., die within 1.5 years) after surgical resection of the Stage IIIB or Stage IIIC melanoma.

As used herein, the term "positive response to the therapeutic regimen" refers to a reduction or improvement in clinical symptoms of a disease or condition and/or enhanced immune response to a disease or condition following the therapeutic regimen. With respect to the instant methods, the reduction or improvement in clinical symptoms relates to those associated with Stage IIIB or Stage IIIC melanoma.

As used herein, the term "genetic signature" refers to a gene expression pattern of a sample. A genetic signature, therefore, refers to a pattern or profile of expression levels for a plurality of genes in a sample. The term may be used to refer to a comprehensive gene expression pattern for a sample or a relevant subset thereof. With respect to the present methods, a genetic signature for a melanoma sample may be determined for a subset of genes that relate to duration of survival or predicted response to a therapeutic regimen as described herein.

As used herein, the term "immune response genetic signature" refers to a gene expression pattern that is positively correlated with immune cells and enhanced immune responses.

As used herein, the term "cell proliferation genetic signature" refers to a gene expression pattern that is positively correlated with proliferating cells or a cellular environment conducive to cell proliferation.

As used herein with regard to gene expression, a "reference" refers to the average gene expression level for a particular gene in the short lived patient cohort (patients living less than 1.5 years post-surgical resection of their Stage IIIB or Stage IIIC melanoma) as described herein. Data for determination of the average of each of the genes listed in the Tables presented herein is publicly available and can be found at http://www.ncbi.nlm.nih.gov/geo/query/acc.cgi?acc=GSE19234.

B. DETAILED DISCLOSURE

The system most often used to stage melanoma is the American Joint Commission on Cancer (AJCC) Tumor/Node/Metastasis (TNM) system. Several tests and procedures are used to assign T, N, and M categories and a grouped stage. The TNM system for staging contains 3 key pieces of information. "T" stands for tumor and indicates how far it has grown within the skin and other factors. The T category is assigned a number (from 0 to 4) based on the tumor's thickness (how far down it has grown). It is also assigned a small letter "a" if it is not ulcerated or a "b" if it is ulcerated. Ulceration means the layer of skin covering the melanoma is absent. This is seen under a microscope after a biopsy. "N" stands for spread to nearby lymph. The N category is assigned a number (from 0 to 3) based on whether the melanoma cells have spread to lymph nodes or are found in the lymphatic channels connecting the lymph nodes. It is also assigned a small letter: "a" if melanoma cells can only be seen with the microscope or "b" if they can be seen with the naked eye. A letter "c" is assigned if there are very small areas of melanoma in the nearby skin or if the melanoma is in skin lymphatic channels around the tumor (but not in the nodes themselves). The M category is based on whether the melanoma has metastasized (spread) to distant organs, which organs it has reached, and sometimes on blood levels of a substance called LDH.

There are, furthermore, two types of staging for melanoma: clinical and pathologic staging. Clinical staging is based on what is found on physical exam, biopsy of the melanoma, and any imaging tests that are done. Pathologic staging uses all of this information, plus what is found during biopsies of lymph nodes or other organs. Therefore, the clinical stage (determined before the node biopsy) may actually be lower than the pathologic stage (determined after the node biopsy).

The T category is based on the thickness of the melanoma and other key factors seen in the skin biopsy. This is an important part of determining a patient's prognosis. With regard to tumor thickness, a pathologist looking at the skin biopsy measures the thickness of the melanoma under the microscope using a micrometer. This technique is called the Breslow measurement. The thinner the melanoma, the better the prognosis. In general, melanomas less than 1 millimeter (mm) in depth have a very small chance of spreading. As the melanoma becomes thicker, it has a greater chance of spreading. To determine mitotic rate, a pathologist counts the number of cells that are in the process of dividing (mitosis) in a specified amount of melanoma tissue. A higher mitotic rate (having more cells that are dividing) means that the cancer is more likely to grow and spread. The mitotic rate is used to help stage thin melanomas (T1; see below). If the melanoma is ulcerated (the outermost covering layer of skin is absent), the prognosis tends to be worse.

The possible values for T are: T0: No evidence of primary tumor; Tis: Melanoma in situ (The tumor remains in the epidermis); T1a: The melanoma is less than or equal to 1.0 mm thick (1.0 mm=$\frac{1}{25}$ of an inch), without ulceration and with a mitotic rate of less than $1/mm^2$; T1b: The melanoma is less than or equal to 1.0 mm thick. It is ulcerated and/or the mitotic rate is equal to or greater than $1/mm^2$; T2a: The melanoma is between 1.01 and 2.0 mm thick without ulceration; T2b: The melanoma is between 1.01 and 2.0 mm thick with ulceration; T3a: The melanoma is between 2.01 and 4.0 mm thick without ulceration; T3b: The melanoma is between 2.01 and 4.0 mm thick with ulceration; T4a: The melanoma is thicker than 4.0 mm without ulceration; T4b: The melanoma is thicker than 4.0 mm with ulceration.

The possible values for N depend on whether or not a sentinel lymph node biopsy was done. The clinical staging of the lymph nodes is listed below; it is done without the sentinel node biopsy and is designated as follows: NX: Nearby (regional) lymph nodes cannot be assessed; N0: No spread to nearby lymph nodes; N1: Spread to 1 nearby lymph node; N2: Spread to 2 or 3 nearby lymph nodes, OR spread of melanoma to nearby skin or toward a nearby lymph node area (without reaching the lymph nodes); N3: Spread to 4 or more lymph nodes, OR spread to lymph nodes that are clumped together, OR spread of melanoma to nearby skin or toward a lymph node area and into the lymph node(s).

Following a lymph node biopsy, the pathologic stage can be determined. The involvement of any lymph nodes can be subdivided as follows: any Na (N1a, N2a, etc.) means that the melanoma in the lymph node is so small that it is only seen under the microscope; any Nb (N1b, N2b, etc.) means that the melanoma in the lymph node is visible to the naked eye; N2c means the melanoma has spread to very small areas of nearby skin (satellite tumors) or has spread to skin lymphatic channels around the tumor (without reaching the lymph nodes).

The M values are: M0: No distant metastasis; M1a: Distant metastases to skin or subcutaneous (below the skin) tissue or distant lymph nodes; M1b: Metastases to lung; M1c: Metastases to other organs, OR distant spread to any site along with an elevated blood LDH level.

Using the TNM system, a doctor will use each letter (T, N, and M) and a corresponding number, as follows:

Stage 0

Tis, N0, M0: The melanoma is in situ, meaning that it involves the epidermis but has not spread to the dermis (lower layer).

Stage IA

T1a, N0, M0: The melanoma is less than 1.0 mm in thickness. It is not ulcerated and has a mitotic rate of less than $1/mm^2$. It appears to be localized in the skin, and has not been found in lymph nodes or distant organs.

Stage IB

T1b or T2a, N0, M0: The melanoma is less than 1.0 mm in thickness and is ulcerated or has a mitotic rate of at least $1/mm^2$, OR it is between 1.01 and 2.0 mm and is not ulcerated. It appears to be localized in the skin and has not been found in lymph nodes or distant organs.

Stage IIA

T2b or T3a, N0, M0: The melanoma is between 1.01 mm and 2.0 mm in thickness and is ulcerated, OR it is between 2.01 and 4.0 mm and is not ulcerated. It appears to be localized in the skin and has not been found in lymph nodes or distant organs.

Stage IIB

T3b or T4a, N0, M0: The melanoma is between 2.01 mm and 4.0 mm in thickness and is ulcerated, OR it is thicker than 4.0 mm and is not ulcerated. It appears to be localized in the skin and has not been found in lymph nodes or distant organs.

Stage IIC

T4b, N0, M0: The melanoma is thicker than 4.0 mm and is ulcerated. It appears to be localized in the skin and has not been found in lymph nodes or distant organs.

Stage IIIA

T1a to T4a, N1a or N2a, M0: The melanoma is not ulcerated. It has spread to 1 to 3 lymph nodes near the affected skin area, but the nodes are not enlarged and the melanoma is found only when they are viewed under the microscope. There is no distant spread. The thickness of the melanoma is not a factor, although it is usually thick in people with stage III melanoma.

Stage IIIB

T1b to T4b, N1a or N2a, M0: The melanoma is ulcerated. It has spread to 1 to 3 lymph nodes near the affected skin area, but the nodes are not enlarged and the melanoma is found only when they are viewed under the microscope. There is no distant spread.

T1a to T4a, N1b or N2b, M0: The melanoma is not ulcerated. It has spread to 1 to 3 lymph nodes near the affected skin area. The nodes are enlarged because of the melanoma. There is no distant spread.

T1a/b to T4a/b, N2c, M0: The melanoma may or may not be ulcerated. It has spread to small areas of nearby skin or lymphatic channels around the original tumor, but the nodes do not contain melanoma. There is no distant spread.

Stage IIIC

T1b to T4b, N1b or N2b, M0: The melanoma is ulcerated. It has spread to 1 to 3 lymph nodes near the affected skin area. The nodes are enlarged because of the melanoma. There is no distant spread.

Any T, N3, M0: The melanoma may or may not be ulcerated. It has spread to 4 or more nearby lymph nodes, OR to nearby lymph nodes that are clumped together, OR it has spread to nearby skin or lymphatic channels around the original tumor and to nearby lymph nodes. The nodes are enlarged because of the melanoma. There is no distant spread.

Stage IV

Any T, Any N, M1: The melanoma has spread beyond the original area of skin and nearby lymph nodes to other organs such as the lung, liver, or brain, or to distant areas of the skin or lymph nodes. Neither the lymph node status nor thickness is considered in this stage, but typically the melanoma is thick and has also spread to lymph nodes.

The above information pertaining to melanoma staging was adapted from the American Cancer Society website, which was last revised in August 2010.

In light of the above, it is apparent that metastatic melanoma is a biologically diverse disease. Stage III patients present a particularly challenging patient population for clinicians since the melanoma has, by definition, started to metastasize. Accordingly, the prognosis for Stage III melanoma patients is generally poor. Some Stage III melanoma patients do, however, exhibit enhanced survival potential, but contributing factors to such features in Stage III patients were largely unknown in advance of the present findings. Additional indicators and methods for differentiating patients diagnosed with Stage III melanoma so as to identify patients having enhanced survival potential and/or enhanced responsiveness to therapeutic intervention are, therefore, required to improve Stage III patient care and it is to this objective that the present disclosure is directed. Identification of the indicators/biomarkers and methods for using same as described herein makes it possible to tailor clinical trials to the molecular and cellular profile of each patient. Indicators/biomarkers as described herein may also be used to tailor therapeutic intervention for individual Stage III melanoma patients, to evaluate efficacy of therapeutic intervention for individual Stage III melanoma patients, and to predict Stage III melanoma patient survival with greater accuracy.

Figure 2:
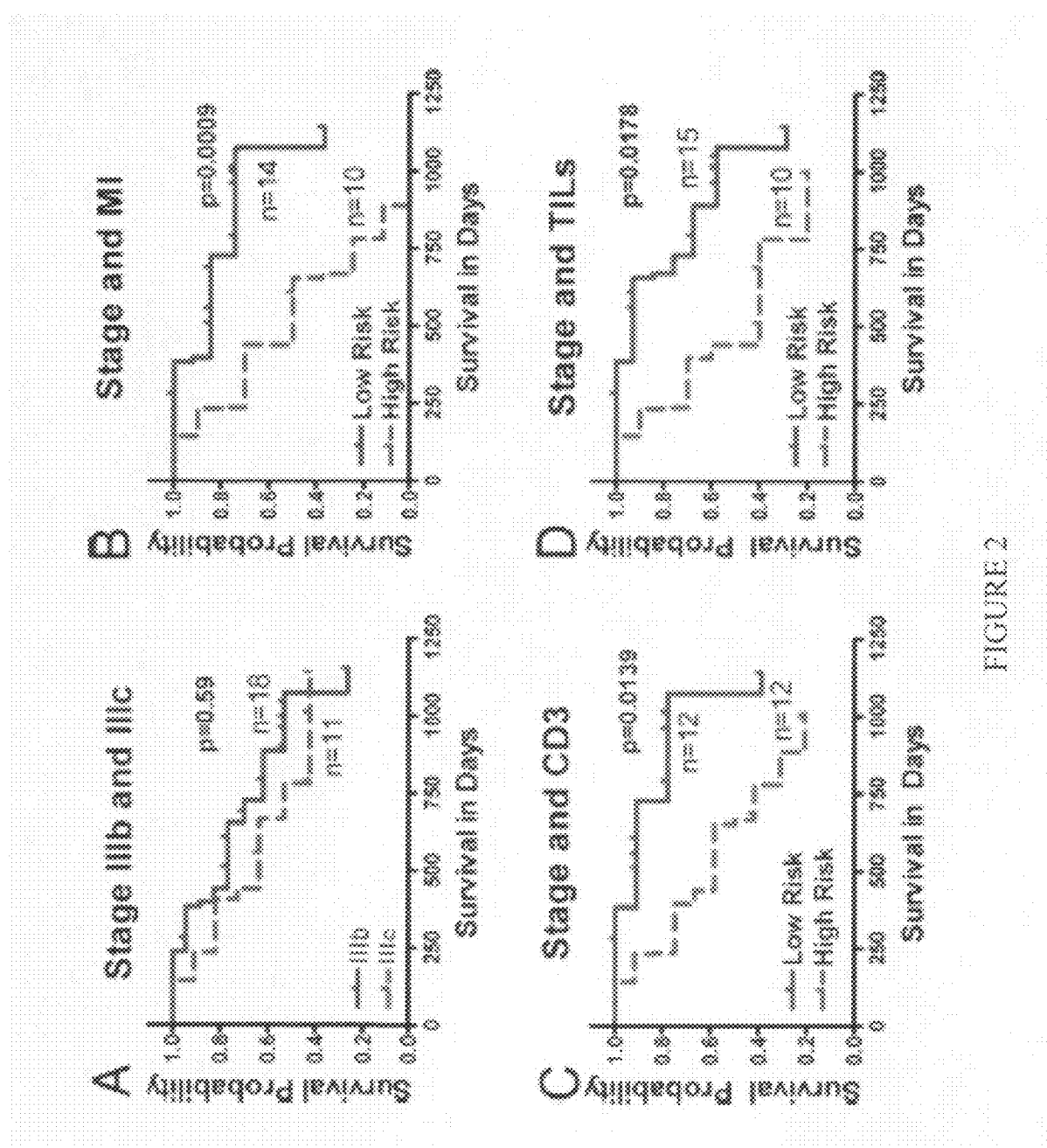
FIG. 2A-D shows that MI, CD3 counts, and TILs are useful indicators for subclassifying Stage IIIb and IIIc patients to predict survival time. Patients with staging of IIIb and IIIc are represented in (A). As shown therein, their survival capabilities cannot be distinguished using only staging criteria ($P=0.59$). By incorporating MI, CD3, and TILs (B-D) in the model, it is possible to improve the ability to separate stage IIIb/IIIc patients based on their survival ($P=0.0009$, $P=0.0139$, and $P=0.0178$, respectively).

As alluded to herein above, although remission rates for metastatic melanoma are generally very poor, some patients can survive for prolonged periods following metastasis. As described herein, the present inventors used gene expression profiling, mitotic index (MI), and quantification of tumor infiltrating leukocytes (TILs) and CD3+ cells in metastatic lesions to search for molecular and cellular bases for this observation and to develop improved methods for predicting patient survival. The present inventors identified a group of 266 genes associated with postrecurrence survival. See Table 1 as depicted in FIG. 5. Genes positively associated with survival were predominantly immune response related (e.g., ICOS, CD3d, ZAP70, TRAT1, TARP, GZMK, LCK, CD2, CXCL13, CCL19, CCR7, VCAM1), while genes negatively associated with survival were cell proliferation related (e.g., PDE4D, CDK2, GREF1, NUSAP1, SPC24). See, e.g., Tables 1-5 as depicted in FIGS. 5-9. Furthermore, any of the four parameters, including prevalidated gene expression signature (see, e.g., Table 5; FIG. 9), TILs, CD3, and in particular MI (see, e.g., FIGS. 1 and 2 and Tables 6 and 7), improved the ability of Tumor, Node, Metastasis (TNM) staging to predict postrecurrence survival. MI was the most significant contributor (HR=2.13, P=0.0008). An immune response gene expression signature and presence of TILs and CD3+ cells signify immune surveillance as a mechanism for prolonged survival in these patients and indicate improved patient subcategorization beyond current TNM staging.

It is noteworthy that the current diagnostic parameters as set forth above and in accordance with standard practice in the field of clinical oncology do not include assessment of mitotic index (MI), or quantification of tumor infiltrating leukocytes (TILs), or CD3+ cells in metastatic lesions isolated from Stage IIIB and Stage IIIC melanoma patients. Indeed, of these parameters, only MI is recommended for melanoma staging and/or diagnostic purposes and such recommendations are limited to evaluation of Stage IA and IB patients. As set forth above, the differentiating mitotic index for TNM staging with respect to Stage IA and IB patients is the number of mitoses per 1 mm$^2$. This differs from that of the present method which counts the number of mitoses per high power field (HPF; which equals 0.196 mm$^2$). Thus, 0.75 mitoses per HPF, as described herein, equals 3.83 mitoses per 1 mm$^2$. This is a significant differentiating factor of nearly four-fold relative to that described in connection with TNM staging of Stage I melanoma. It is, moreover, significant that the results of Reddy et al. (J Cutan Pathol 22:248, 1995), for example, suggest that expression of cell proliferation markers is not correlated with or predictive of prognosis in advanced level melanoma. Accordingly, the results presented herein pertaining to mitotic index are surprising at least in light of the findings of Reddy et al.

Quantification of TILs and/or CD3+ cells in metastatic lesions of any stage of melanoma is not recommended for melanoma staging. Accordingly, Stage IIIB and Stage IIIC melanoma staging does not include an assessment of such parameters, nor is there any reason, in advance of the guidance presented in the present disclosure, for an ordinarily skilled practitioner to believe that assessing such parameters would be useful for predicting duration of survival or positive response to therapeutic intervention of Stage IIIB and Stage IIIC melanoma patients. It is only with the guidance presented herein that evidence demonstrating a nexus between Stage IIIB and/or Stage IIIC melanoma patient survival and/ or positive response to prospective therapeutic intervention and assessing MI, and/or quantifying TILs and/or CD3+ cells in metastatic lesions isolated from these patients is established. With an appreciation of the nexus, ordinarily skilled practitioners can assess these parameters and use this information to predict survival and/or clinical response of Stage IIIB and Stage IIIC melanoma patients under their care.

As described herein in the Examples, the presence of TILs is established by visual analysis of hematoxylin and eosin (H&E)-stained melanoma samples and indexed to 4 categories (0=0-5%, 1=5-25%, 2=25-50% and 3=>50%) each designating the percentage of tumor section that was represented by TILs. As with CD3+ T cells, only the portion of tumor at least 2 HPFs away from the tumor's interface with the normal lymph node parenchyma was examined for this assessment.

In accordance with the present findings, Stage IIIB or Stage IIIC melanoma patients having elevated MI indices in their metastatic lesions are predicted to have short survival duration (less than 1.5 years) post-diagnosis with Stage IIIB or Stage IIIC melanoma and are good candidates for treatment with therapeutic intervention targeting highly proliferative cells, such as chemotherapy and/or B-Raf inhibitors (e.g., GDC-0879, PLX-4720, Sorafenib, Tosylate, or PLX4032). See, for example, Agarwala Expert Rev Anticancer Therapy 9:587, 2009; Yang et al. Hematol Oncol Clin N Am 23:583, 2009; Bhatia et al. [Oncology (Williston Park) 23:488, 2009]; and Mouawad et al. Crit Rev Oncol/Hematol 74:27, 2010 regarding additional therapeutic approaches, each of which references is incorporated herein in its entirety.

Also in accordance with the present findings, Stage IIIB or Stage IIIC melanoma patients having elevated levels of CD3+ cells in their metastatic lesions exhibit features characteristic of a robust immune response and are predicted to live longer than 1.5 years post-diagnosis with Stage IIIB or Stage IIIC melanoma and are good candidates for immune therapy. Stage IIIC melanoma patients having elevated levels of TILs in their metastatic lesions also exhibit features characteristic of a robust immune response and are predicted to live longer than 1.5 years post-diagnosis with Stage IIIC melanoma and are good candidates for immune therapy. Larger studies may confirm the initial studies presented herein that Stage IIIB melanoma patients having elevated levels of TILs in their metastatic lesions also exhibit features characteristic of a robust immune response and are predicted to live longer than 1.5 years post-diagnosis with Stage IIIB melanoma and are good candidates for immune therapy.

Exemplary immune therapy regimens are known in the art and include, without limitation: melanoma associated antigens (MAA) delivered with adjuvants (Toll like receptor agonists; Montanide or GM-CSF); viral vectors expressing MAA; dendritic cell targeted therapies such as MMA-fused to anti-Dec 205 receptor; and adoptive T cell therapy that targets MAA expressed in the tumors. See, for example, Gnjatic et al. Cancer J. 16:382, 2010; Rosenberg et al. Curr Opin Immunol. 21:233, 2009; and Bhatia et al. Oncology (Williston Park) 23:488, 2009, each of which references is incorporated herein in its entirety. Adoptive immunity reactive with NY-ESO-1 has also been demonstrated to be highly effective in metastatic melanoma patients whose tumors express NY-ESO-1 (~25% melanoma patients). See, for example, Jäger et al. Proc Natl Acad Sci USA. 103:14453, 2006; Hunder et al. N Engl J. Med. 358:2698; 2008; Tsuji et al. J Immunol. 186:1218, 2011; and Robbins et al. J Clin Oncol epub Jan. 31, 2011, each of which references is incorporated herein in its entirety. Biologics such as interferon-α (IFN-α), interleukin-2 (IL-2), combinations of IFN-α and IL-2, anti-CTLA-4 and anti-PD-1 are also envisioned. See also, for example, Bhatia et al. Oncology (Williston Park) 23:488, 2009; Agarwala Expert Rev Anticancer Therapy 9:587, 2009; Yang et al. Hematol Oncol Clin N Am 23:583, 2009; and Mouawad et al. Crit Rev Oncol/Hematol 74:27, 2010, each of which references is incorporated herein in its entirety.

The present inventors, moreover, envision that assessing the genetic signatures of Stage IIIB and Stage IIIC melanoma patients and comparison to those genetic signatures identified herein (as set forth in, for example, Tables 1-5), which are associated with survival (enhanced or and/or potential positive response to therapeutic intervention, can also be used to predict survival and/or responsiveness of patients diagnosed with Stage IIIB or Stage IIIC melanoma to various therapeutic regimens. Stage IIIB and Stage IIIC melanoma patients having a genetic signature characteristic of an active immune response, as typified by higher expression levels of genes associated with the immune response, are predicted to live longer than 1.5 years post-diagnosis of Stage IIIB or Stage IIIC melanoma and are good candidates for immune therapy. In accordance with guidance presented herein, upregulation or enhanced expression of genes associated with a robust immune response as listed in any one of Tables 1-4 and downregulation or reduced expression of genes associated with cellular proliferation as listed in any one of Tables 1-4 is indicative of longer survival duration and is predictive of a positive outcome following immune therapy for Stage IIIB or Stage IIIC melanoma patients. In contrast, upregulation or enhanced expression of genes indicative of cellular proliferation as listed in any one of Tables 1-4 is correlated with reduced survival duration and is predictive of a positive outcome following therapy that targets rapidly proliferating cells (e.g., chemotherapy). Therapeutic regimens designed to target rapidly proliferating cells are known in the art and described herein below. As described herein, a genetic signature comprising altered expression of at least 6 genes listed in any one of Tables 1-4, either altered so as to increase expression relative to a reference for an immune response gene or altered so as to decrease expression relative to a reference for a cell proliferation gene, is indicative of longer survival duration and is predictive of a positive outcome following immune therapy for Stage IIIB or Stage IIIC melanoma patients. A genetic signature comprising altered expression of at least 6 genes listed in any one of Tables 1-4, altered so as to increase expression relative to a reference for a cell proliferation gene, is indicative of shorter survival duration and is predictive of a positive outcome following, e.g, chemotherapy for Stage IIIB or Stage IIIC melanoma patients.

As also described herein, the expression pattern of at least six of the genes listed in Table 5 (prevalidated gene predictors) is correlated to survival duration for melanoma patients, particularly those diagnosed with Stage IIIB or Stage IIIC melanoma. As indicated in the Examples, Table 5 lists genes that are positively or negatively correlated with survival; statistical analyses used to generate this list take into account the duration of survival time and thus, lend weight to expression patterns that correlate with prolonged survival time. As detailed herein, Stage IIIB and Stage IIIC melanoma patients having a genetic signature indicative of an active immune response, as typified by higher expression levels of genes associated with immune responses, are predicted to live longer and may be good candidates for immune therapy. Accordingly, identification of a genetic signature reflecting upregulation or enhanced expression of genes associated with or indicative of a robust immune response as indicated in Table 5 and downregulation or reduced expression of genes indicative of cellular proliferation as listed in Table 5 is indicative of longer survival duration and may be predictive of a positive outcome following immune therapy. In contrast, a genetic signature reflecting upregulation or enhanced expression of genes indicative of cellular proliferation as listed in Table 5 is correlated with reduced survival duration and may be predictive of a positive outcome following therapy that targets rapidly proliferating cells (e.g., chemotherapy). A determination that a melanoma sample isolated from a Stage IIIB or Stage IIIC patient has a genetic signature consistent with at least 6 genes included in the prevalidated gene expression signature listed in Table 5 could, therefore, be used to predict survival duration and/or be used to choose a therapeutic regimen designed to target the genetic signature of the melanoma in the patient from whom the melanoma is isolated. A genetic signature suggestive of an active immune response would direct a practitioner to choose a therapeutic regimen that would promote the ongoing immune response (e.g., immune therapy), whereas a genetic signature suggestive of cell proliferation would direct a practitioner to choose a therapeutic regimen that would inhibit cell proliferation (e.g., chemotherapy).

Accordingly, methods are encompassed herein that call for analysis of a genetic signature of a melanoma sample based on a match of at least 6, at least 10, at least 15, at least 20, at least 50, at least 100, at least 150, at least 200, at least 250, or 266 (and all whole integers between 1 and 266) of the genes listed in any one of Tables 1-5. It is understood that the total number of genes listed in each of Tables 1-5 varies, so the matching criteria for an analysis of a gene signature will depend on the total number of genes listed in a particular Table and subsets thereof. With regard to Table 5, for example, methods for assessing the expression of at least 6, at least 10, at least 15, at least 20, or all 21 of the genes listed in Table 5 are envisioned. With regard to Table 3, for example, methods for assessing the expression of at least 6, at least 10, at least 15, at least 20, at least 25, at least 30, at least 35, at least 40, at least 45, or all 50 of the genes listed in Table 3 are envisioned.

Stage IIIB and Stage IIIC melanoma patients having a genetic signature characteristic of a high proliferative index, as typified by higher expression levels of genes associated with the cellular proliferation, are predicted to live fewer than 1.5 years post-diagnosis of Stage IIIB or Stage IIIC melanoma and are good candidates for chemotherapy and/or B-Raf specific or MEK inhibitors. In accordance with guidance presented herein, upregulation or enhanced expression of at least six of the genes associated with a high proliferative rate or index as listed in any one of Tables 1-5 is indicative of shorter survival duration and predictive of a positive outcome for Stage IIIB or Stage IIIC melanoma patients following therapeutic regimens involving chemotherapy and/or B-Raf inhibitors. Exemplary B-Raf inhibitors are known in the art and include, e.g., GDC-0879, PLX-4720, Sorafenib, Tosylate, and PLX4032.

It is noteworthy that the standard of care for patients with advanced melanoma is largely focused on surgical resection. This is due in large part to the fact that prior to the present disclosure there was little information available on which basis a clinician could stratify patients to predict what, if any, therapeutic intervention would confer benefit to a patient diagnosed with Stage IIIB or Stage IIIC melanoma. With regard to melanomas diagnosed at Stage IIIB or Stage IIIC melanoma, wherein lymph nodes are enlarged near the melanoma or wherein several nodules of melanoma are identified leading away from the tumor (stage III-in-transit), additional testing is performed. Enlarged lymph nodes are biopsied, either by excision or by fine needle aspiration. If enlarged lymph nodes that drain the tumor are detected, a computed axial tomography (CT) scan of the pelvis is recommended. A chest x-ray and assessment of blood lactacte dehydrogenase (LDH) levels are also routinely performed. Other scans may be done depending on the site of the melanoma and the patient's symptoms.

If a lymph node biopsy reveals melanoma therein, all the lymph nodes in that localized area are completely removed along with a wide excision of the melanoma.

After all melanoma has been surgically removed, adjuvant therapy may be considered. Prior to the advances of the present methods, however, there was little guidance on which basis to evaluate which treatment was best for a Stage IIIB or Stage IIIC melanoma patient. Accordingly, many Stage IIIB or Stage IIIC melanoma patients do not receive any further treatment following surgical resection, but rather undergo close observation thereafter. Patients can also opt to enroll in a clinical trial or undergo treatment via interferon injection. Radiation may also be merited if the melanoma in any lymph node area was multinodal or grew outside the lymph nodes into surrounding tissue.

If several melanomas are observed tracking away from the main tumor (in transit), they are biopsied and ideally all removed. If complete eradication of detectable disease is not possible, treatment options include: laser therapy or direct injection of Bacille Calmette Guerin (BCG) or interferon into the melanoma. These therapies are, however, largely ineffectual. If the melanoma is on an extremity (e.g., a limb), the area can be perfused with a melphalan solution heated to 102° to 104° F. Tumor necrosis factor may also be added. Again, without the benefit of the present discovery, little guidance existed to assist in the choice of potential treatments, so some stage III-in-transit patients would consider entering a clinical trial in the hopes that an experimental protocol would confer benefit. Other possible treatments include: radiation therapy to the area, or systemic treatment, such as chemotherapy or cytokine treatment or both.

In short, options available to Stage IIIB or Stage IIIC melanoma patients are largely limited to surgical resection, followed by careful observation by a clinician, or entry into a clinical trial for further treatment or interferon injections. With the guidance presented herein, however, clinicians have the tools and methods required to stratify Stage IIIB or Stage IIIC melanoma patients to predict survival duration and response to various therapeutic regimens. Indeed, the tools and methods described herein may be used to categorize Stage IIIB or Stage IIIC melanoma patients as good candidates (positive responders) for immune therapy to promote the patients' ongoing immune responses or as good candidates (positive responders) for treatment with inhibitors of cell proliferation to combat high proliferative rates of their melanomas.

Gene Expression Analysis

Genetic signatures are provided herein that may be used to determine prognosis, predict survival, and evaluate response to therapeutic intervention for Stage IIIB and Stage IIIC melanoma patients. As described herein, the genetic signatures described herein may be used to analyze gene expression in melanoma samples isolated from Stage IIIB and Stage IIIC melanoma patients to subclassify or stratify such patients into short-lived and long-lived patients (determine survival index) and/or predict which patients would benefit from therapeutic intervention and tailor the therapeutic intervention to the genetic signature of each patient's melanoma. Analysis of a genetic signature of a melanoma sample isolated from Stage IIIB or Stage IIIC melanoma patient can also be used to identify which therapeutic intervention would confer optimal benefit to such a patient. Methods for analyzing gene expression include methods based on hybridization analysis of polynucleotides, sequencing of polynucleotides, and analysis of protein expression (e.g., proteomics-based methods). Commonly used methods are for the quantification of mRNA expression in a sample include northern blotting and in situ hybridization (Parker & Barnes, Methods in Molecular Biology 106:247-283, 1999); RNAse protection assays (Hod, Biotechniques 13:852 854, 1992); and PCR-based methods, such as reverse transcription polymerase chain reaction (RT-PCR) (Weis et al., Trends in Genetics 8:263 264, 1992). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

Microarrays

As described herein, evaluating gene expression of a melanoma sample can be performed with microarrays. Microarrays permit simultaneous analysis of a large number of gene expression products. Typically, polynucleotides of interest are plated, or arrayed, on a microchip substrate. The arrayed sequences are then hybridized with nucleic acids (e.g., DNA or RNA) from cells or tissues of interest (e.g., cutaneous tissue samples). The source of mRNA typically is total RNA (e.g., total RNA isolated from human melanoma samples, and normal skin samples). If the source of mRNA is a primary tumor, mRNA can be extracted, for example, from frozen or archived paraffin-embedded and fixed (e.g. formalin-fixed) tissue samples.

In various embodiments of the microarray technique, probes to at least 6, 10, 25, 50, 100, 150, 200, or 266 genes (e.g., genes listed in Tables 1-5 herein, which distinguish Type IIIB and IIIC melanoma into subcategories predictive of survival and responsiveness to therapy) are immobilized on an array substrate (e.g., a porous or nonporous solid support, such as a glass, plastic, or gel surface). The probes can include DNA, RNA, copolymer sequences of DNA and RNA, DNA and/or RNA analogues, or combinations thereof.

In some embodiments, a microarray includes a support with an ordered array of binding (e.g., hybridization) sites for each individual gene. The microarrays can be addressable arrays, and more preferably positionally addressable arrays, i.e., each probe of the array is located at a known, predetermined position on the solid support such that the identity (i.e., the sequence) of each probe can be determined from its position in the array.

Each probe on the microarray can be between 10-50,000 nucleotides, e.g., between 300-1,000 nucleotides in length. The probes of the microarray can consist of nucleotide sequences with lengths: less than 1,000 nucleotides, e.g., sequences 10-1,000, or 10-500, or 10-200 nucleotides in length. An array can include positive control probes, e.g., probes known to be complementary and hybridizable to sequences in the test sample, and negative control probes, e.g., probes known to not be complementary and hybridizable to sequences in the test sample.

Methods for attaching nucleic acids to a surface are known. Methods for immobilizing nucleic acids on glass are described, e.g., Schena et al, Science 270:467-470, 1995; DeRisi et al, Nature Genetics 14:457-460, 1996; Shalon et al., Genome Res. 6:639-645, 1996; and Schena et al., Proc. Natl. Acad. Sci. U.S.A. 93:10539-11286, 1995). Techniques are known for producing arrays with thousands of oligonucleotides at defined locations using photolithographic techniques are described by Fodor et al., 1991, Science 251:767-773, 1991; Pease et al., Proc. Natl. Acad. Sci. U.S.A. 91:5022-5026, 1994; Lockhart et al., Nature Biotechnology 14:1675, 1996; U.S. Pat. Nos. 5,578,832; 5,556,752; and 5,510,270). Other methods for making microarrays have been described. See, e.g., Maskos and Southern, Nuc. Acids. Res. 20:1679-1, 684, 1992. In principle, and as noted supra, any type of array, for example, dot blots on a nylon hybridization membrane (see Sambrook et al., Molecular Cloning, A Laboratory Manual, 2nd Ed., Vols. 1-3, Cold Spring Harbor Laboratory, Cold Spring Harbor, N.Y. (1989)) could be used.

The polynucleotide molecules to be analyzed may be from any clinically relevant source, and are expressed RNA or a nucleic acid derived therefrom (e.g., cDNA or amplified RNA derived from cDNA that incorporates an RNA polymerase promoter), including naturally occurring nucleic acid molecules, as well as synthetic nucleic acid molecules. For example, the test polynucleotide molecules include total cellular RNA, poly(A)+ messenger RNA (mRNA), or fraction thereof, cytoplasmic mRNA, or RNA transcribed from cDNA (i.e., cRNA). Methods for preparing RNA are known and are described, e.g., in Sambrook et al., Molecular Cloning, A Laboratory Manual ($2^{nd}$ Ed.), Vols. 1-3, Cold Spring Harbor Laboratory, Cold Spring Harbor, N.Y., 1989. RNA can be fragmented by methods known in the art, e.g., by incubation with $ZnCl_2$, to generate fragments of RNA.

Test polynucleotide molecules that are poorly expressed in particular cells can be enriched using normalization techniques (Bonaldo et al., Genome Res. 6:791-806, 1996).

The test polynucleotides may be detectably labeled at one or more nucleotides. Any method known in the art may be used to detectably label the polynucleotides.

Nucleic acid hybridization and wash conditions are chosen so that the test polynucleotide molecules specifically bind or specifically hybridize to the complementary polynucleotide sequences of the array, preferably to a specific array site, wherein its complementary nucleic acid is located. General parameters for specific (i.e., stringent) hybridization conditions for nucleic acids are described in Sambrook et al., supra, and in Ausubel et al., Current Protocols in Molecular Biology, vol. 2, Current Protocols Publishing, New York, 1994. Typically, stringent conditions for short probes (e.g., 10 to 50 nucleotide bases) will be those in which the salt concentration is at least about 0.01 to 1.0 M at pH 7.0 to 8.3 and the temperature is at least about 30° C. Stringent conditions can also be achieved with the addition of destabilizing agents such as formamide. When fluorescently labeled probes are used, the fluorescence emissions at each site of a microarray can be detected by scanning confocal laser microscopy or other methods (see Shalon et al., Genome Research 6:639-645, 1996; Schena et al., Genome Res. 6:639-645, 1996; and Ferguson et al., Nature Biotech. 14:1681-1684, 1996). Signals are recorded and typically analyzed by computer. Methods for evaluating microarray data and classifying samples are described in U.S. Pat. No. 7,171,311.

PCR-Based Methods

Combinations of genes predictive of prognosis, survival, or responsiveness of Stage IIIB and Stage IIIC melanoma can also be analyzed by PCR. PCR is useful to amplify and detect transcripts from a melanoma sample. Various PCR methodologies are useful for gene expression analyses.

Reverse Transcriptase PCR (RT-PCR). RT-PCR is a sensitive quantitative method that can be used to compare mRNA levels in different samples (e.g., Stage IIIB or Stage IIIC melanoma samples) to examine gene expression signatures.

To perform RT-PCR, mRNA is isolated from a sample (e.g., total RNA isolated from a human metastatic melanoma sample). mRNA can be extracted, for example, from frozen or archived paraffin-embedded and fixed (e.g. formalin-fixed) tissue samples. Methods for mRNA extraction are known in the art. See, e.g., Ausubel et al., Current Protocols in Molecular Biology, John Wiley and Sons, 1997. Methods for RNA extraction from paraffin embedded tissues are disclosed, for example, in Rupp and Locker, Lab Invest. 56:A67, 1987, and De Andres et al., BioTechniques 18:42044, 1995. Purification kits for RNA isolation from commercial manufacturers, such as Qiagen, can be used. For example, total RNA from a sample can be isolated using Qiagen RNeasy mini-columns.

Other commercially available RNA isolation kits include MasterPure™. Complete DNA and RNA Purification Kit (EPICENTRE™, Madison, Wis.), and, Paraffin Block RNA Isolation Kit (Ambion, Inc.). Total RNA from tissue samples can be also isolated using RNA Stat-60 (Tel-Test) or by cesium chloride density gradient centrifugation.

Isolated RNA is reverse transcribed into cDNA. The cDNA is amplified in a PCR reaction. Two commonly used reverse transcriptases are avian myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the conditions and desired readout. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction. The PCR reaction typically employs the Taq DNA polymerase, which has a 5'-3' nuclease activity but lacks a 3'-5' proofreading endonuclease-activity. Two oligonucleotide primers are used to generate an amplicon in the PCR reaction.

Guidelines for PCR primer and probe design are described, e.g., in Dieffenbach et al., "General Concepts for PCR Primer Design" in: PCR Primer, A Laboratory Manual, Cold Spring Harbor Laboratory Press, New York, 133-155, 1995; Innis and Gelfand, "Optimization of PCRs" in: PCR Protocols, A Guide to Methods and Applications, CRC Press, London, 5-11, 1994; and Plasterer, T. N. Primerselect: Primer and probe design. Methods Mol. Biol. 70:520-527, 1997. Factors considered in PCR primer design include primer length, melting temperature (Tm), and G/C content, specificity, complementary primer sequences, and 3'-end sequence. PCR primers are generally 17-30 bases in length, and Tm's between 50-80° C., e.g. about 50 to 70° C. are typically preferred.

For quantitative PCR, a third oligonucleotide, or probe, is used to detect nucleotide sequence located between the two PCR primers. The probe is non-extendible by Taq DNA polymerase enzyme, and typically is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative analysis.

RT-PCR can be performed using commercially available equipment, such as an ABI PRISM 7700™ Sequence Detection System (Perkin-Elmer-Applied Biosystems, Foster City, Calif., USA), or Lightcycler®. (Roche Molecular Biochemicals, Mannheim, Germany). Samples can be analyzed using a real-time quantitative PCR device such as the ABI PRISM 7700™. Sequence Detection System™.

To minimize errors and the effect of sample-to-sample variation, RT-PCR is usually performed using an internal standard. A suitable internal standard is expressed at a constant level among different tissues, and is unaffected by the experimental variable. RNAs frequently used to normalize patterns of gene expression are mRNAs for the housekeeping genes glyceraldehyde-3-phosphate-dehydrogenase (GAPDH) and β-actin.

A variation of the RT-PCR technique is real time quantitative PCR, which measures PCR product accumulation through a dual-labeled fluorigenic probe (i.e., TaqMan™ probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., Genome Res. 6:986-994, 1996.

Gene expression can be examined using fixed, paraffin-embedded tissues as the RNA source. Briefly, in one exemplary method, sections of paraffin-embedded tumor tissue samples are cut (~10 μm thick). RNA is extracted, and protein and DNA are removed. After analysis of the RNA concentration, RNA repair and/or amplification steps may be performed, if necessary, and RNA is reverse transcribed using gene specific promoters followed by RT-PCR. Methods of examining expression in fixed, paraffin-embedded tissues, are described, for example, in Godfrey et al., J; Molec. Diagn. 2: 84-91, 2000; and Specht et. al., Am. J. Pathol. 158: 419-29, 2001.

Another approach for gene expression analysis employs competitive PCR design and automated, high-throughput matrix-assisted laser desorption ionization time-of-flight (MALDI-TOF) MS detection and quantification of oligonucleotides. This method is described by Ding and Cantor, Proc. Natl. Acad. Sci. USA 100:3059-3064, 2003. See also the MassARRAY-based gene expression profiling method, developed by Sequenom, Inc. (San Diego, Calif.).

Additional PCR-based techniques for gene expression analysis include, e.g., differential display (Liang and Pardee, Science 257:967-971, 1992); amplified fragment length polymorphism (iAFLP) (Kawamoto et al., Genome Res. 12:1305-1312, 1999); BeadArray™ technology (Illumina, San Diego, Calif.; Oliphant et al., Discovery of Markers for Disease (Supplement to Biotechniques), June 2002; Ferguson et al., Analytical Chemistry 72:5618, 2000); BeadsArray for Detection of Gene Expression (BADGE), using the commercially available Luminex100 LabMAP system and multiple color-coded microspheres (Luminex Corp., Austin, Tex.) in a rapid assay for gene expression (Yang et al., Genome Res. 11:1888-1898, 2001); and high coverage expression profiling (HiCEP) analysis (Fukumura et al., Nucl. Acids. Res. 31(16) e94, 2003).

Serial Analysis of Gene Expression (SAGE)

Gene expression in Stage IIIB and Stage IIIC melanoma samples can also be determined by serial analysis of gene expression (SAGE), which is a method that allows the simultaneous and quantitative analysis of a large number of gene transcripts, without the need of providing an individual hybridization probe for each transcript (see, e.g. Velculescu et al., Science. 270:484-487, 1995; and Velculescu et al., Cell 88:243-51, 1997). Briefly, a short sequence tag (about 10-14 nucleotides) is generated that contains sufficient information to uniquely identify a transcript, provided that the tag is obtained from a unique position within each transcript. Many transcripts are then linked together to form long serial molecules that can be sequenced, revealing the identity of the multiple tags simultaneously. The expression pattern of a population of transcripts can be quantitatively evaluated by determining the abundance of individual tags, and identifying the gene corresponding to each tag.

Analysis of Expression Data

The raw expression files pertaining to gene expression levels for patient cohorts described herein can be downloaded from http://www.ncbi.nlm.nih.gov/geo/guery/acc.cgi?acc=GSE19234. After normalization (using PLIER algorithm), therefore, any gene mentioned in the tables presented herein can be evaluated for relative expression level as compared to the average expression level for the gene in question determined for the short-lived cohort of patients in the database (reference). If the number generated on a chip from a new patient is, for example, an immune gene that is 1.5 fold higher than the average of that gene for the patients who died within 540 days since recurrence (short-lived cohort) in the database provided, then the patient is predicted to have a long duration of survival. If a proliferative gene is examined and the new patient's chip data reveal that this gene is 1.5 lower than the reference (the average expression level of that gene for the patients who died within 540 days since recurrence in the database provided), then this patient is predicted to have a long survival duration.

For comparison to the PV gene predictor, at least 6 genes should be evaluated as described in the methods. Positive and negative correlations for survival are indicated in Tables 1-4 for most of the genes listed in Table 5. Briefly, Cox proportional hazards model is fitted with the first principal component of the 6 genes in the training set as a predictor (see database online), and survival since metastatic excision as a dependent variable (see database online). Based on this model, hazard ratios are estimated for the training set and the test set cases divided into low risk and high risk, using the median training set hazard ratio as a cutoff point. New patient expression of at least 6 genes is evaluated by calculating the first principal component of the 6 genes to see if the patient can be considered low or high risk.

Protein Detection Methodologies

Immunohistochemical methods are also suitable for detecting the expression of the melanoma signature genes described herein. Antibodies, most preferably monoclonal antibodies, specific for a gene product are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

Proteomic methods can allow examination of global changes in protein expression in a sample. Proteomic analysis typically involves separation of individual proteins in a sample by 2-D gel electrophoresis (2-D PAGE), and identification of individual proteins recovered from the gel, e.g. my mass spectrometry or N-terminal sequencing, and analysis of the data using bioinformatics. Proteomics methods can be used alone or in combination with other methods for evaluating gene expression.

In various aspects, the expression of certain genes in a cutaneous sample is detected to provide clinical information (e.g., prognostic information, classification of the Stage IIIB or Stage IIIC tumor from which the sample is derived as a melanoma associated with prolonged or truncated longevity). Thus, gene expression assays include measures to correct for differences in RNA variability and quality. For example, an assay typically measures and incorporates the expression of certain normalizing genes, such known housekeeping genes, e.g., GAPDH, β-actin, and Cyp1. Alternatively, normalization can be based on the mean or median signal (Ct) of all of the assayed genes or a large subset thereof (global normalization approach). In some embodiments, a normalized test RNA (e.g., from a patient sample) is compared to the amount found in a metastatic melanoma, non-metastatic melanoma, and/or normal skin sample reference set. The level of expression measured in a particular test sample can be determined to fall at some percentile within a range observed in reference sets.

Kits

The technology herein includes kits for evaluating gene expression (e.g., RNA or protein) in melanoma samples. A "kit" refers to a combination of physical elements, e.g., probes, including without limitation specific primers, labeled nucleotic acid probes, antibodies, protein-capture agent(s), reagent(s), instruction sheet(s) and other elements useful to practice the technology described herein. These physical elements can be arranged in any way suitable for carrying out the invention.

A kit for analyzing protein expression can include specific binding agents, such as immunological reagents (e.g., an antibody, e.g., a labeled antibody) for detecting proteins expressed of one or more genes described herein (e.g., one or more genes from Table 1, Table 2, Table 3, Table 4, or Table 5). For example, the kit can include an antibody that detects expression of any of the genes listed in Tables 1-5, including an antibody that detects expression of CCL19, an antibody that detects expression of IGLL1, and an antibody that detects expression of NEFM, in a tissue section.

Kits for analyzing RNA expression include, for example, a set of oligonucleotide probes for detecting expression of a set of genes described herein (e.g., six or more genes from Table 1, Table 2, Table 3, Table 4, or Table 5). The probes can be provided on a solid support, as in an array (e.g., a microarray), or in separate containers. The kits can include a set of oligonucleotide primers useful for amplifying a set of genes described herein, e.g., to perform PCR analysis. Kits can include further buffers, enzymes, labeling compounds, and the like.

Diagnostic Assays

The present invention also relates to a variety of diagnostic applications, including methods for determining the prognosis of a Stage IIIB or Stage IIIC melanoma patient and methods for assessing predicted overall survival in a Stage IIIB or Stage IIIC melanoma patient, wherein the genetic signature, Mitotic Index (MI), and levels of tumor infiltrating lymphocytes (TILs) and CD3+ cells are detected and determined in a tumor biopsy, cellular sample, or metastatic melanoma cell sample.

As demonstrated herein, the molecular signature of Stage IIB and Stage IIIC melanoma patients having relatively prolonged life spans (survival greater than 1.5 years post-surgery) differs from those Stage IIB and Stage IIIC melanoma patients having shorter life spans (survival less than 1.5 years post-surgery). In brief, relatively prolonged life span is associated with elevated levels of genes associated with immune responses as compared to short lived metastatic melanoma cohorts. Enhanced expression of transcripts encoding, for example, MHC class II molecules (HLA-DOB, HLA-DPB1), T cell-associated molecules (ICOS, CD3d, ZAP70, TRAT1, TARP, GZMK, LCK, CD27), chemokines, chemokine receptors and adhesion molecules (CD11A, CXCL13, CCL19, CCR7, VCAM1, AMICA1) and a number of other innate and adaptive immune response molecules (CD79A, LTB, CLEC4G, CLECL1, FCER1A, IKZF1, TAP1, IRF1, IRF8, GBP2, IL4R, IL2RG, IKZF1, C3, MYADM, TLR10, NLRC5, FCAMR, BTLA, NLRC3, CD48) is correlated with relatively prolonged life span. Such expression patterns are positively correlated with immune cells and enhanced immune responses. Relatively prolonged life span is also associated with decreased levels of genes associated with cell proliferation as compared to short lived metastatic melanoma cohorts. Decreased expression of genes broadly characterized as pertaining to "cell proliferation", including ANLN, PDE4D, CDK2, CXCL1, CGREF1, NUSAP1, and SPC24, is correlated with relatively prolonged life span.

As demonstrated by the findings presented herein, relatively prolonged life span (survival greater than 1.5 years post-surgery) in Stage IIIB and Stage IIIC melanoma patients is also associated with reduced MI and increased levels of CD3+ cells in metastatic melanoma samples of such patients as compared to samples from shorter lived cohorts (survival less than 1.5 years post-surgery).

The present findings also reveal that relatively prolonged life span (survival greater than 1.5 years post-surgery) in Stage IIIC melanoma patients is also associated with increased levels of TILs in metastatic melanoma samples of such patients as compared to samples from shorter lived cohorts (survival less than 1.5 years post-surgery). This also appears to apply to Stage IIIB melanoma patients, although this assessment would benefit from analysis of larger patient cohorts.

Figure 3:
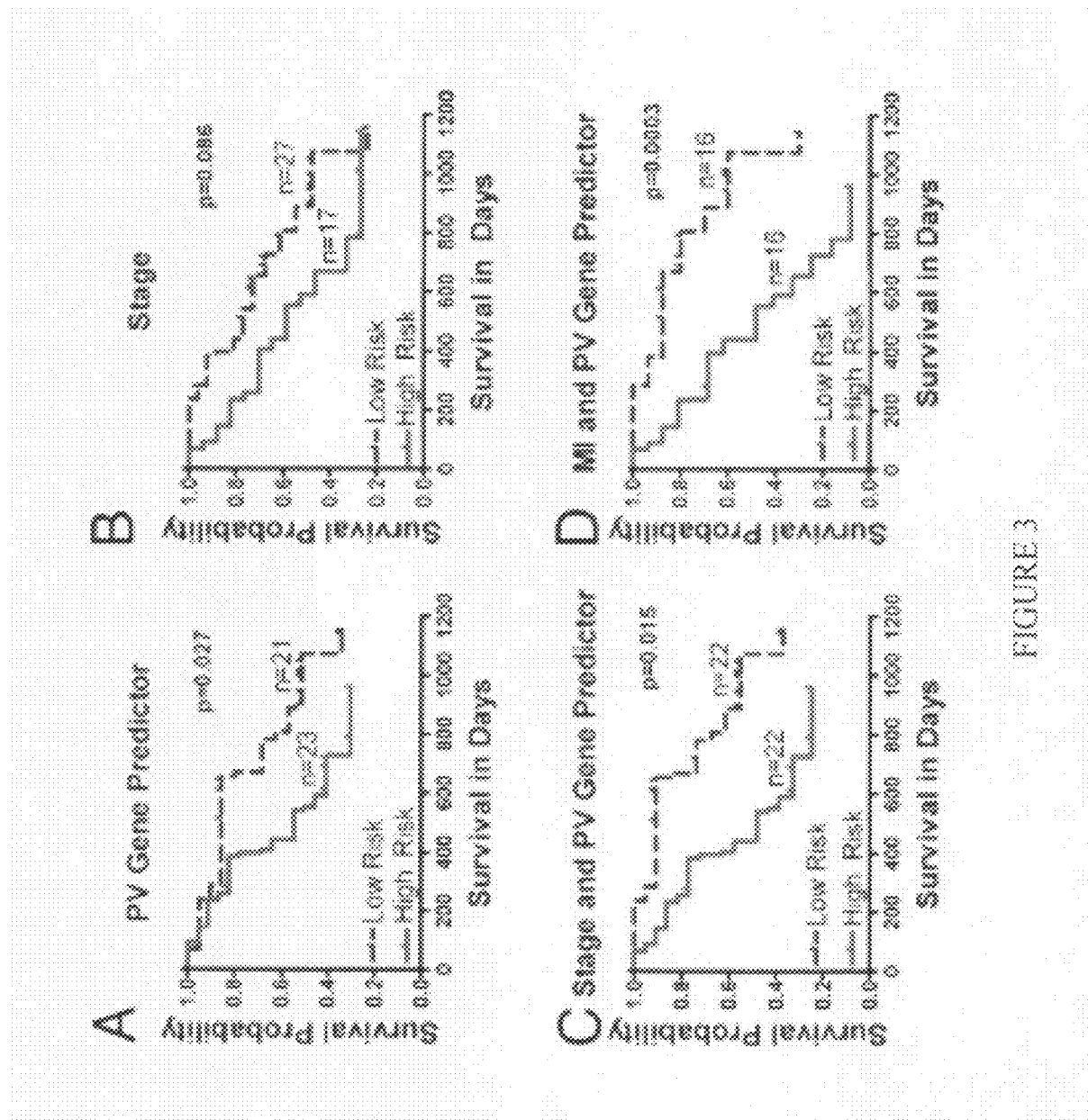
FIG. 3A-D shows that gene signature (PV) and MI are capable of improving current outcome prediction model through machine learning. Predicted high-risk and low-risk groups obtained using (A) prevalidated gene expression predictor ($P=0.027$), (B) Stage alone ($P=0.086$), (C) combination of Stage and prevalidated gene predictor ($P=0.015$) and (D) combination of MI and prevalidated gene predictor ($P=0.0003$).

Also shown herein, expression analysis of samples by comparison to the PV gene predictor signature disclosed herein and expression of subsets comprising at least six genes listed therein, reveals superior capability for predicting patient outcome as compared to TNM staging, whether PV gene predictor analysis is performed alone, or in combination with MI, which yields even more statistically significant results. See, for example, FIG. 3.

As alluded to herein above, expression analysis by comparison to the PV gene predictor signature provides useful information on which basis a therapeutic regimen in the adjuvant setting (following removal of detectable disease) can be chosen which is tailored to the genetic signature of the Stage IIIB or Stage IIIC melanoma. If expression analysis reveals that the genetic signature of a Stage IIIB or Stage IIIC melanoma matches the PV gene predictor signature with regard to at least 6 genes included therein and correlates with an immune response genetic signature, the method predicts that the patient will have a longer duration of survival and will respond favorably to immune therapy to boost their ongoing immune response. If, on the other hand, expression analysis reveals that the genetic signature of a Stage IIIB or Stage IIIC melanoma matches the PV gene predictor signature with regard to at least 6 genes included therein and correlates with a cell proliferation genetic signature, the method predicts that the patient will have a shorter duration of survival and should be treated aggressively with inhibitors of cell proliferation to combat the highly proliferative state of the melanoma tumor. Expression analysis by comparison to the PV gene predictor signature post-therapeutic intervention may also indicate whether the therapy chosen is adversely affecting the melanoma on a genetic basis and thus, conferring benefit to the patient The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

Methods

Sample Population. Under an Institutional Review Board approved protocol, the present inventors enrolled the first 38 patients and collected 44 melanoma samples, since some patients had 2 or 3 recurrences. Patient median age at 1st recurrence was 62.5 years, with a range from 30 to 92 years. Sixty-three percent of patients were males and 37% were females. All of the patients underwent surgery, 32% received chemotherapy, 24% underwent radiation therapy, and 13% underwent immunotherapy. Eighteen percent of patients presented at stage I, 29% at stage II, 47% at stage III, and 3% at stage IV. For validation, data on an independent cohort of 29 patients available online at ArrayExpress database (www.ebi.ac.uk/arrayexpress) under accession number E-TABM-403 were used. Another independent cohort to validate our findings using MI, TILs, and CD3 consisted of 52 randomly selected samples from patients with stage IIIb and IIIc melanoma.

MI, CD3 Cell Count, and TILs. The inventors assessed TILs and MI in hematoxylin and eosin (H&E)-stained tissue sections and performed immunohistochemistry staining to assess tumor infiltrating CD3 positive cells. Since many of the tissue samples were from lymph node metastases, any lymphocytes in the vicinity of tumor borders were excluded. Tumor slides were examined by 2 pathologists who were both blinded to the patients' clinical data. MI was established by counting mitoses in 10 high power fields (HPF) per tumor section and then averaging the number by HPF (1.96 mm$^2$). CD3 positive cells were counted only within the tumor at least 2 HFPs away from the tumor's interface with the normal lymph node parenchyma. CD3+ cells in 10 high power fields per tumor section were counted and that number is reported. On H&E stains we established presence of TILs and indexed to 4 categories (0=0-5%, 1=5-25%, 2=25-50% and 3=50%+) each showing the percentage of tumor section that was represented by TILs. As with CD3+ T cells, only the portion of tumor at least 2 HPFs away from the tumors' interface with the normal lymph node parenchyma was examined. 44 tissue samples from 38 patients were hybridized to Genechips. However, MI, TILs, and CD3 were only available for 30, 31, and 29 of the 38 patients, respectively, with complete data on all 3 parameters available for a total of 28 patients. This explains the differing numbers in the tables. For example, n=30 in Table 7 that describes a model based on MI. Table 12A describes the 44 samples (not patients) and Table 12B describes 32 samples (not patients).

Statistical Methods/Clinical Data Analysis. The clinical data were summarized numerically and graphically to verify the normality assumption and for outlier detection. Box-Cox transformations were used to transform variables with deviations from normality, such as MI and CD3 cell count (30). The variable TILs were treated as ordered in the analysis. TNM stage was dichotomized in the analysis due to small sample size. For clinical data analysis, the unit of analysis was the patient and not recurrence/metastasis. However, all reported results hold for per recurrence analysis. For each patient with multiple samples, the sample corresponding to the earliest recurrence/metastasis was used in the analysis. Cox proportional hazards model was used for prediction. The median estimated hazard ratio was used to divide the patients into low and high risk groups. All analyses were performed using the R language for statistical computing (31).

Gene Chip Processing. Post surgery collected tissue was placed in RNA later (Qiagen) at 4° C. overnight, then stored at −80° C. Before whole RNA extraction (RNeasy Mini Kit, Qiagen), touch preparations were performed to ensure that the specimen obtained was mostly tumor tissue. RNA quality was assessed using an Agilent 2100 Bioanalyzer (Agilent Technologies). Double stranded cDNA synthesis was performed using a SuperScript double-stranded cDNA synthesis kit from Invitrogen. In vitro transcription of biotin-labeled cRNA probes was done using an IVT labeling kit (Affymetrix). Fragmented biotin-labeled cRNA was hybridized on Affymetrix Human Genome U 133 Plus 2.0 chips, in the Rockefeller University Genomics Core laboratory.

Gene Chip Data Preprocessing. The raw gene expression values were normalized using probe logarithmic error intensity estimate. Probes were grouped by their Unigene symbols and the median of expression levels of all probes in a group was taken to be the expression level of the transcript (32). This step resulted in the reduction of a number of features from 54,675 to 23,940. The signals were then further quantile normalized (33).

Significance Analysis of Microarrays. SAM (12) was used to identify genes that are significantly associated with postrecurrence survival using time from recurrence to death (or censored) as the outcome variable. One thousand permutations of the data were used to estimate the FDR (13) and to select differentially expressed genes. Additionally, the patients were dichotomized into 2 groups: those with prolonged survival (>1.5 years) and those with "shorter survival" (<1.5 years). A 2-sample nonparametric comparison was used in SAM to identify genes that are differentially expressed between these 2 groups. The significant gene lists resulting from the 2 types of analyses (survival and 2-sample comparison) were then compared.

Prevalidated Gene Expression Predictor. To derive a gene expression signature of postrecurrence survival, the method of PV was used (15, 16). PV outputs a prediction for each patient based on the model that is estimated without using that patient's data. Per recurrence analysis was used herein because PV facilitates reduction in bias that might arise due to the dependence among multiple recurrences of the same patient. An 11-fold PV was used to construct a gene expression predictor of postrecurrence survival. The 44 samples were divided into 11 groups of 4 samples randomly, but in such a way that samples from the same patient were always grouped together to reduce bias. At each PV fold, one of the 11 groups of 4 samples was set aside as a test set and the remaining 40 samples were used as a training set. The training set was analyzed using SAM to select the top 3 up-regulated and top 3 down-regulated genes, resulting in an output of 6 top genes. The inventors calculated the first principal component of the 6 genes in the training data. The inventors fit the Cox proportional hazards model with the first principal component of the 6 genes in the training set as a predictor, and survival since metastatic excision as a dependent variable. Based on this model, the inventors estimated hazard ratios for the training set and divided the test set cases into low risk and high risk, using the median training set hazard ratio as a cutoff point. This procedure was repeated 11 times, each time reserving a different set of 4 samples for the test set. Note that for each patient, the above PV procedure outputs a prediction based on the model that was estimated without using that patient's data and, therefore, no overfitting occurs. Varying the number of genes selected by SAM between 4 and 20 produced similar PV predictors. The resulting PV gene expression predictor was compared to the other clinical predictors in a multivariable Cox regression model.

Gene Selection via Signal-to-Noise Ratio. To select the informative genes which should be included in the model, the signal-to-noise ratio (SNR), a feature selection method found to perform well in gene expression experiments, was used (5, 18). The signal-to-noise ratio favors genes that have nonoverlapping distributions with far apart means. The inventors experimented with the top 10, 30, 50, 100, 300, 500, and 1,000 genes, and used 1.5- and 2-fold change to further narrow down the set of candidate genes. We found that the best performance measures do not improve with the inclusion of more than the top 50 genes (Table 11). Although different methods were applied, the overlap between SAM genes and top 50 SNR genes is remarkably high.

Prediction, Performance Evaluation, and Estimation of Statistical Significance.

Due to their ability to handle datasets with a small number of highly dimensional examples with correlated features, support vector machines (SVM) are a popular supervised learning method to analyze gene expression data (17, 18). To estimate the prediction accuracy, the inventors used leave-one-out crossvalidation. Here one example is systematically held out and the model is built on all of the remaining examples and tested on the example which was hidden while the model was learned. We report the following performance measurements: prediction accuracy, sensitivity, specificity and AUC. In each leave-one-out iteration, values of Unigene features were normalized to have zero mean and unit variance using z-score normalization. In experiments described herein, results with and without the use of PCA are reported. The inventors set the amount of retained variance after performing PCA to 0.95.

Immunohistochemistry. Immunohistochemistry was performed on formalin fixed, paraffin embedded tissues using mouse anti-human CD3, clone PS-1 (Ventana Medical Systems). In brief, sections were deparaffinized in xylene, rehydrated through graded alcohols and rinsed in distilled water. Heat induced epitope retrieval was performed in 10 mM citrate buffer pH 6.0 for 10 min in a 1200-Watt microwave oven at 90% power. CD3 was applied undiluted and incubated for 30 min. Primary antibody was detected with Ventana's biotinylated goat anti-mouse secondary followed by application of streptavidin-horseradish-peroxidase conjugate. The complex was visualized with 3,3 diaminobenzidene and enhanced with copper sulfate. Slides where washed in distilled water, counterstained with hematoxylin, dehydrated, and mounted with permanent media.

Results

Gene Expression Profiling of Metastatic Melanoma Lesions Identifies Genes Associated with Survival. To evaluate the association between gene expression profiles and survival in patients with metastatic melanoma, the present inventors evaluated 44 metastatic melanoma tissue samples from 38 patients who were followed clinically for a median of 20 months (2-38 months range) after excision of the metastatic lesion. Thirty-nine of the tumor samples were taken from patients with stage III disease, with 5 samples from patients with stage IV disease (Table 8). We evaluated the association of gene expression profiles of patient tumors and survival based on time from excision of the metastatic lesion to last follow-up or death. Using the Significant Analysis of Microarrays (SAM) (12) with a false discovery rate (FDR) (13) of 5.34% and filtering for at least a 1.5 fold change in expression between patients with prolonged survival (>1.5 years) compared to those with shorter survival, we identified a set of 266 genes (FIG. 5, Table 1) that are significantly associated with postrecurrence survival.

To gain insight into the functional classes of these 266 genes, the inventors analyzed them using the National Institute of Allergy and Infectious Diseases/National Institutes of Health Database for Annotation, Visualization and Integrated Discovery (DAVID) Bioinformatics Resource 2008 (Table 9). In the group of patients with prolonged survival, the top functional annotation cluster for up-regulated transcripts was "immune system process" (top enrichment score of 13.42, representing 40 transcripts). The transcripts included those encoding MHC class II molecules (HLA-DOB, HLA-DPB1), T cell-associated molecules (ICOS, CD3d, ZAP70, TRAT1, TARP, GZMK, LCK, CD27), chemokines, chemokine receptors and adhesion molecules (CD11A, CXCL13, CCL19, CCR7, VCAM1, AMICA1) and a number of other innate and adaptive immune response molecules (CD79A, LTB, CLEC4G, CLECL1, FCER1A, IKZF1, TAP1, IRF1, IRF8, GBP2, IL4R, IL2RG, IKZF1, C3, MYADM, TLR10, NLRC5, FCAMR, BTLA, NLRC3, CD48). The upregulation of immune system transcripts in metastatic lesions of patients with longer survival suggests that the immune response may keep tumor growth and metastasis in check in these patients.

Genes that were down-regulated in patients with prolonged survival belonged to multiple functional annotation clusters, with the top 2 enrichment scores of 1.61 and 1.17 representing about 10 transcripts involved in (but not limited to) "cell cycle phase," "M phase," "cofactor binding," "cell division," "cytoskeleton," and "aminotransferase" (Table 9). Genes in this category, which could be more broadly characterized as "cell proliferation", included ANLN, PDE4D, CDK2, CXCL1, CGREF1, NUSAP1, and SPC24. The up-regulation of genes associated with cell division in patients with high mortality risk, suggests that higher rates of mitosis within metastatic lesions is associated with more rapid tumor growth and spread of metastatic disease.

Tumor Infiltrating Leukocytes and Tumor Cell Mitoses Are Predictive of Patient Survival. To determine if a simple, independent method could demonstrate an association of immune or proliferative parameters with patient survival, the inventors examined histological sections from the same pathology specimens used for gene expression analysis. The inventors quantified 3 different parameters—TILs, MI and CD3+ T cell count (CD3), and assessed whether any or all of these were independently associated with survival (FIG. 1A-F).

Patients were divided into 3 groups based on the prevalence of TILs within their tumor (<25% TILs, 25 to 50% TILs, and >50% TILs as assessed by percentage of the lesion area represented by leukocytes, see methods). In addition, using the median value as the cutoff point, patients were divided into 2 groups each based on CD3 count (lower and higher than 80 CD3+ cells per 10 High Power Fields (HPFs) and MI (lower and higher than 0.75 Mitoses per HPF, Table 10). Median survival estimates along with the 95% confidence intervals for these groups are provided in Table 10. Shown in FIGS. 1G, H, I, and J are Kaplan-Meier survival curves for the groups defined by MI, TILs, CD3 counts and TNM stage at the time of surgery, respectively. All 3 histological parameters were significantly associated with survival: patients with lower MI survived significantly longer (P<0.0001, log rank test) as did patients with higher TIL indices (P=0.0163) and CD3 counts (P=0.0134). Please note that due to some missing histological specimens, certain figures and tables have differing specimen numbers (see Methods).

TNM staging in our cohort was effective in separating patients with stage IIIA (n=4) and stage IV (n=5) disease by survival (P=0.0006, log rank test). However, the vast majority (n=29) of patients in the cohort had stage IIIB or IIIC disease, and here TNM staging showed no differential association with survival (P=0.59) (FIGS. 1J, and 2A).

To assess if any of the 3 histologic parameters, CD3 count, MI, or TILs, could significantly improve upon the ability of TNM staging in predicting postrecurrence survival, the inventors fitted 3 multivariable Cox regression models. Each model involved one of these predictors (CD3 count or MI or TILs) and TNM stage as independent variables and postrecurrence survival as the dependent variable (Table 6A-C). Adding any of the 3 histologic parameters significantly improved upon the ability of TNM stage to predict survival: MI was the strongest contributor (HR=2.13, P=0.0008) followed by CD3 count (HR=0.80, P=0.0022) and TILs (HR=0.26, P=0.0067). Using these models, patients were divided into "low" and "high" risk groups using the median hazard ratio as a cut-off point. Kaplan-Meier survival curves of low and high risk groups among stage IIIB/IIIC patients based on each of these 3 models are shown in FIG. 2B-D. For comparison, Kaplan-Meier survival curves for stage IIIB/IIIC patients based on TNM stage alone are provided in FIG. 2A. Adding any of the 3 parameters to TNM stage resulted in the ability to segregate stage IIIB and IIIC patients into high and low risk groups with significantly different survival probabilities. The median survival times were 1073 days in the low-risk group (95% confidence interval, 1073 to "not reached") and 496 days in the high-risk group (95% confidence interval, 237 to "not reached") based on the model with TNM and MI as predictors. Out of 15 patients in stage IIIb, 11 segregated into low risk and 4 into high risk. In the case of 9 IIIc patients, 3 segregated into low risk and 6 into high risk (Table 7). The clinical characteristics of the low and high risk groups predicted by the model with TNM and MI as predictors are provided in Table 7.

TABLE 6

Hazard ratios (HRs) and 95% Confidence Intervals (CIs) for TNM stage, MI, CD3 count, and TIL based on 3 multivariable Cox proportional hazards models of postrecurrence survival

|  | HR (95% CI) | p value |
|---|---|---|
| A |  |  |
| TNM stage* IIIA/IIIB vs. IIIC/IV | 2.05 (0.76, 5.54) | 0.16 |
| Mitotic Index | 2.13 (1.38, 3.32) | 0.0008 |
| B |  |  |
| TNM stage* IIIA/IIIB vs. IIIC/IV | 1.82 (0.70, 4.74) | 0.22 |
| TILs | 0.26 (0.10, 0.69) | 0.0067 |
| C |  |  |
| TNM stage* IIIA/IIIB vs. IIIC/IV | 1.27 (0.46, 3.56) | 0.64 |
| CD3 count | 0.80 (0.70, 0.92) | 0.0022 |

All three histologic parameters, MI, CD3, and TILs, add to the ability of TNM stage in predicting postrecurrence survival. A: HRs and 95% CIs for TNM stage and MI based on a Cox regression model involving these variables. B: HRs and 95% CIs for TNM stage and TIL based on a Cox regression model involving these variables. C: HRs and 95% CIs for TNM stage and CD3 count based on a Cox regression model involving these variables.
*Due to a small sample size, TNM stage was dichotomized (IIIA/B vs. IIIC/IV). The other three variables were dichotomized for convenience using medians as cut-off points.

Figure 4:
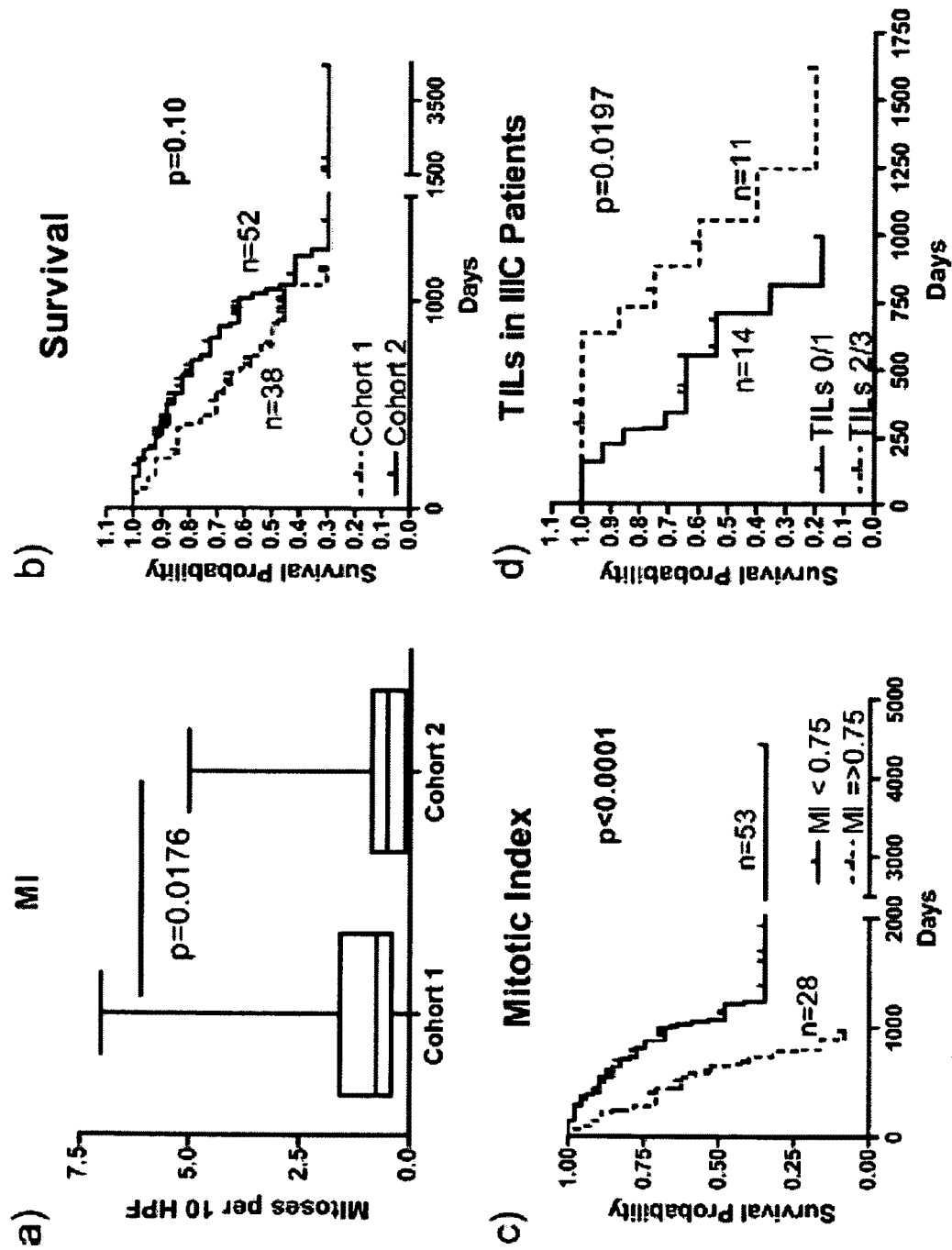
FIG. 4A-D reveals that MI aids staging in combined initial and validation patient cohorts in predicting their survival. Fifty-two additional patient samples with stage IIIb and IIIc were examined for MI and TILs. They had significantly lower MI (A) ($P=0.0176$) and longer overall survival (B) ($P=0.10$) than the initial cohort. When the initial and validation cohort were combined (n=90) MI was a significant predictor of survival (C) ($P<0.0001$). TILs were a significant predictor of survival (D) ($P=0.0197$) only in IIIc patients in the validation cohort.

An independent cohort of patients was evaluated to see if these observations could be validated. Accordingly, 52 additional metastatic melanoma samples taken from 25 stage IIIb and 27 stage IIIc patients were analyzed. MI of the patients in the validation cohort was significantly lower than that of the patients in the original cohort studied (P=0.0176, FIG. 4a) while postrecurrence survival was longer, although not statistically significant (P=0.10, FIG. 4b). TNM stage was a significant predictor of survival in the validation cohort (P=0.003). MI alone was not significant in additionally separating survival in the validation cohort. To examine this further, the inventors then combined the 2 cohorts into an expanded cohort of 90 patient samples; using the original MI cutoff of 0.75, patients were separable into high and low risk groups with significantly different survival (FIG. 4c, P<0.0001). For stage IIIb/c patients in the combined cohort, multivariate Cox proportional hazards model showed that MI was a more important predictor of survival [HR=3.08, 95% CI: (1.38, 6.90), P=0.0062] than TNM stage [HR=2.13, 95% CI: (1.02, 4.47), P=0.05]. Furthermore, TIL frequency was a significant predictor of survival in IIIc patients in the validation cohort (FIG. 4d, P=0.0197) but not for stage IIIb patients.

Prevalidated Gene Expression Predictor of Survival in Metastatic Melanoma. To test if gene expression signatures bear predictive prognostic potential in metastatic melanoma, the inventors derived a gene expression predictor of survival using principal component analysis (PCA) (14) applied to the genes selected by SAM as described in the methods section. The method of prevalidation (PV) was used to derive the gene expression predictor and to compare its prediction accuracy to that of MI, TILs, CD3 cell count and TNM stage (15, 16). Kaplan-Meier survival curves of low-risk and high-risk groups predicted by the PV gene expression predictor are shown in FIG. 3A. The survival in the 2 groups was significantly different (log rank P=0.027) indicating that gene expression profiles can predict survival in metastatic melanoma.

To confirm this observation using a different learning method, metastatic melanoma expression data was tested

TABLE 7

Clinical characteristics of low and high risk groups predicted based on a Cox multivariable regression model of survival since recurrence/metastasis (R/M) with MI, and TNM stage as predictors (N = 30)

|  |  | Low risk (N = 16) | High risk (N = 14) | Statistical test |
|---|---|---|---|---|
| Sex | Female | 5 (31%) | 6 (43%) | Fisher's P value = 0.71 |
|  | Male | 11 (69%) | 8 (57%) |  |
| Age at recurrence |  | Mean = 65 (SD = 18) | Mean = 59 (SD = 21) | Wilcoxon rank sum P = 0.38 |
| CD3 cell count | ≤80 | 4 (25%) | 10 (83%) | Fisher's P value = 0.0063 |
|  | >80 | 12 (75%) | 2 (17%) |  |
|  | missing | 0 | 2 |  |
| Mitotic index | ≤0.75 | 15 (94%) | 1 (7%) | Fisher's P value < 0.0001 |
|  | >0.75 | 1 (6%) | 13 (93%) |  |
| TILs index | 0-25% | 4 (25%) | 8 (57%) | Fisher's P value = 0.22 |
|  | 25-50% | 6 (37.5%) | 4 (29%) |  |
|  | 50-100% | 6 (37.5%) | 2 (14%) |  |
| Stage at recurrence/metastasis | IIIA | 2 (12.5%) | 0 | Fisher's P value = 0.0137 |
|  | IIIB | 11 (69%) | 4 (29%) |  |
|  | IIIC | 3 (19%) | 6 (43%) |  |
|  | IV | 0 | 4 (29%) |  |
| Radiation | Yes | 4 (25%) | 2 | Fisher's P value = 0.67 |
|  | No | 12 (75%) | 10 |  |
|  | Missing | 0 | 2 |  |
| Immunotherapy | Yes | 0 | 2 (17%) | Fisher's P value = 0.17 |
|  | No | 16 (100%) | 10 (83%) |  |
|  | Missing | 0 | 2 |  |
| Chemotherapy | Yes | 8 (50%) | 3 (25%) | Fisher's P value = 0.25 |
|  | No | 8 (50%) | 9 (75%) |  |
|  | Missing | 0 | 2 |  | using the Support Vector Machine algorithm (17, 18), with and without PCA. We obtained the best performance using the top 50 genes determined using the signal-to-noise ratio gene selection method, with measurements decorrelated using PCA: 78.57% sensitivity, 71.43% specificity, and 81.38% area under the ROC curve (AUC) (Table 11).

As an additional confirmatory method, the gene signature identified herein (FIG. 5, Table 1) was tested on recently published test samples (n=29) that were completely independent of our study (19). This data set was very similar to that of the present investigation as it contained relative mRNA levels of metastatic melanoma lesions from patients with mostly stage IIIb and IIIc disease, with time to recurrence as one of the study variables. We observed 61.54% sensitivity, 62.50% specificity, and 70.67% AUC when we applied our list of 266 genes (only 137 of which were present on their chips) to their data set. For comparison purposes, the same signal-to-noise-ratio method described above was performed, but this time using their data set for both training and testing, reporting the best results using the top 20 genes: 69.23% sensitivity, 68.75% specificity, and 70.67% AUC. Comparing these 2 sets of results indicates that close to the maximal predictability power was achieved using the initial selection of genes from our data set, despite extremely different platforms on which the 2 datasets were generated. This confirms the potential of metastatic melanoma gene expression profiles to predict patient outcome.

Metastatic Melanoma Risk Predictor. To see if PV gene expression predictor could add to the predictive power of TNM staging, the inventors performed a multivariate Cox proportional hazards model with survival since surgery as a dependent variable, and TNM stage and PV gene expression predictor as independent variables. The PV gene expression predictor was significant (HR=2.71, P=0.03), and TNM stage was borderline significant (HR=2.06, P=0.08). Shown in FIGS. 3B and C are Kaplan-Meier survival curves for low and high risk groups predicted using models with stage at R/M only and with PV gene expression predictor and TNM stage together. This model segregated 11 stage IIIb and 6 stage IIIc tissue samples into high risk group, while putting 12 IIIb and 6 IIIc tissue samples into low risk group. Using gene expression analysis of metastatic melanoma patient samples, the inventors are able to add to the predictive power of TNM stage as TNM stage alone was not able to separate patients with stage IIIB and IIIC (Table 12A).

The inventors then performed a multivariate Cox proportional hazards model with survival since surgery as a dependent variable and stage, MI and PV gene expression predictor as independent variables (CD3 and TILs were not used as they were less predictive than MI). MI was the most significant predictor (HR=2.54, P=0.0002), but the PV gene expression predictor was also significant (HR=3.64, P=0.019), while stage was not (HR=1.64, P=0.30). When stage was removed from the model, both MI (HR=2.53, P=0.0001) and PV gene expression predictor (HR=3.91, P=0.013) were still significant. Kaplan-Meier estimated survival curves for low-risk and high-risk groups predicted using this final model are shown in FIG. 3D. Table 12B shows the clinical characteristics of the patients according to the risk groups obtained using this best model. The rates of postrecurrence survival at 2 years (i.e., 730 days) in the low-risk and high-risk groups were 70% [95% CI is (49%, 100%)] and 14% [95% CI is (4.8%, 57%)], respectively. The median survival times were 1,073 days in the low-risk group (95% CI, 805 to "not reached") and 440 days in the high-risk group (95% CI, 237 to "not reached"). The survival in the 2 groups was significantly different (log rank P=0.0003).

Using gene expression analysis of metastatic melanoma patient samples, the present inventors are able to add to the predictive power of TNM staging, since stage alone was not able to separate patients with stage IIIB and IIIC disease. As described herein, the best way to enhance survival prediction is by quantifying the MI, which has the added benefit of being much easier to perform than gene expression analysis. Thus, MI provides a relatively simple and effective way to further differentiate a patient's ability to fight metastatic melanoma, either used alone or in combination with gene expression analysis.

Table 8 shows patients' characteristics and stage at tissue retrieval

| Sex | Age (rec) | Treatment | Status | Stage at retrieval |
|---|---|---|---|---|
| M | 87* | Surgery, Chemo | Alive, NED | IIIB, IIIB |
| M | 79 | Surgery, XRT | Alive, MM | IIIC |
| M | 56 | Surgery | Alive, NED | IIIB |
| F | 84 | Chemo | Died, MM | IV (1b) |
| M | 51 | Surgery, XRT, Chemo | Died, MM | IIIC |
| M | 35 | Surgery, Chemo, XRT, Immuno | Died, MM | IIIB |
| M | 86* | Surgery, Immuno, Chemo | Died, MM | IIIB, IV (1c) |
| M | 51 | Surgery, XRT | Alive, NED | IIIC |
| F | 49 | Surgery, Chemo | Alive, MM | IIIA |
| F | 90 | Surgery | Died, MM | IIIB |
| F | 49 | N/A | Died, MM | IV (1c) |
| M | 54 | Surgery, Chemo | Alive, NED | IIIC |
| F | 54 | Surgery | Alive, MM | IIIB |
| F | 82 | Surgery, Chemo | Alive, NED | IIIB |
| M | 60 | Surgery | Alive, NED | IIIB |
| F | 68 | Surgery, XRT | Alive, MM | IIIB |
| F | 48 | Surgery, XRT, Chemo | Died, MM | IIIB |
| M | 65 | N/A | Died, MM | IIIC |
| M | 78* | Surgery | Died, MM | IIIB, IIIB |
| F | 40* | Surgery, XRT | Died, MM | IIIB, IIIB, IIIB |
| F | 78 | Surgery, Chemo | Died, MM | IIIB |
| M | 74* | N/A | Died, MM | IIIC, IIIC |
| M | 69 | Surgery, Immuno | Died, MM | IV (1b) |
| M | 44 | Surgery | Alive, NED | IIIB |
| M | 43 | Surgery, Immuno | Alive, NED | IIIC |
| M | 30 | Surgery, Chemo | Alive, NED | IIIA |
| M | 60 | Surgery, XRT, Immuno | Alive, NED | IIIA |
| M | 92 | Surgery | Died, MM | IIIB |
| M | 83 | Surgery | Alive, MM | IIIB |
| F | 50 | Surgery | Died, MM | IIIC |
| M | 30 | Surgery | Died, MM | IIIB |
| F | 38 | Surgery | Died, MM | IV (1b) |
| F | 77 | Surgery, XRT | Alive, NED | IIIA |
| M | 70 | Surgery, Chemo | Alive, MM | IIIB |
| M | 52 | Surgery | Died, MM | IIIC |
| M | 79 | Surgery, XRT, Chemo | Alive, NED | IIIB |
| M | 69 | Surgery | Alive, NED | IIIC |
| F | 77 | Surgery | Died, MM | IIIC |

Patient sex, age at disease recurrence (rec), treatment, status at the time of analysis, and stage are represented above.
*Denotes patients with multiple samples, MM = metastatic melanoma, NED = no evidence of disease, XRT = radiation therapy, Chemo = chemotherapy.

Table 9 shows functional annotation clustering using DAVID

| GO term identifier | Class | | | Count | P value | Benjamini |
|---|---|---|---|---|---|---|
| Annotation Cluster 1 Enrichment Score: 13.42 | Up-Regulated genes | | | | | |
| GOTERM_BP_ALL | immune system process | | | 40 | 1.10E−19 | 5.90E−16 |

-continued

| GO term identifier | Class | Count | P value | Benjamini |
|---|---|---|---|---|
| GOTERM_BP_ALL | immune response | 31 | 2.50E−14 | 6.50E−11 |
| GOTERM_BP_ALL | response to stimulus | 44 | 2.00E−08 | 2.10E−05 |
| Down-regulated genes | | | | |
| Annotation Cluster 1 Enrichment Score: 1.61 | | | | |
| SP_PIR_KEYWORDS | aminotransferase | 3 | 4.00E−03 | 9.90E−01 |
| GOTERM_MF_ALL | transaminase activity | 3 | 9.10E−03 | 1.00E+00 |
| INTERPRO | Pyridoxal phosphate-dependent transferase, major region, subdomain 1 | 3 | 1.20E−02 | 1.00E+00 |
| GOTERM_MF_ALL | transferase activity, transferring nitrogenous groups | 3 | 1.20E−02 | 1.00E+00 |
| GOTERM_MF_ALL | pyridoxal phosphate binding | 3 | 2.60E−02 | 1.00E+00 |
| SP_PIR_KEYWORDS | pyridoxal phosphate | 3 | 2.60E−02 | 1.00E+00 |
| GOTERM_MF_ALL | vitamin binding | 3 | 1.20E−01 | 1.00E+00 |
| GOTERM_MF_ALL | cofactor binding | 3 | 2.60E−01 | 1.00E+00 |
| Annotation Cluster 2 Enrichment Score: 1.17 | | | | |
| GOTERM_BP_ALL | M phase | 7 | 1.20E−03 | 1.00E+00 |
| GOTERM_BP_ALL | Mitosis | 6 | 2.50E−03 | 1.00E+00 |
| GOTERM_BP_ALL | M phase of mitotic cell cycle | 6 | 2.60E−03 | 9.90E−01 |
| GOTERM_BP_ALL | Cell cycle phase | 7 | 3.60E−03 | 9.90E−01 |
| GOTERM_BP_ALL | Mitotic cell cycle | 6 | 1.00E−02 | 1.00E+00 |
| GOTERM_BP_ALL | Cell division | 5 | 1.90E−02 | 1.00E+00 |
| SP_PIR_KEYWORDS | Mitosis | 4 | 2.00E−02 | 1.00E+00 |
| GOTERM_BP_ALL | Cell cycle process | 8 | 3.60E−02 | 1.00E+00 |
| SP_PIR_KEYWORDS | Cell division | 4 | 6.10E−02 | 1.00E+00 |
| GOTERM_BP_ALL | Cell cycle | 8 | 7.70E−02 | 1.00E+00 |
| SP_PIR_KEYWORDS | Cell cycle | 5 | 1.10E−01 | 1.00E+00 |
| GOTERM_CC_ALL | Cytoskeletal part | 5 | 3.60E−01 | 1.00E+00 |
| GOTERM_BP_ALL | Cytoskeleton organization and biogenesis | 4 | 3.80E−01 | 1.00E+00 |
| GOTERM_BP_ALL | Regulation of progression through cell cycle | 4 | 3.80E−01 | 1.00E+00 |
| GOTERM_BP_ALL | Regulation of cell cycle | 4 | 3.80E−01 | 1.00E+00 |
| GOTERM_CC_ALL | Microtubule cytoskeleton | 3 | 5.10E−01 | 1.00E+00 |
| GOTERM_CC_ALL | Cytoskeleton | 6 | 5.30E−01 | 1.00E+00 |
| GOTERM_CC_ALL | Nonmembrane-bound organelle | 8 | 7.40E−01 | 1.00E+00 |
| GOTERM_CC_ALL | Intracellular non-membrane-bound organelle | 8 | 7.40E−01 | 1.00E+00 |
| GOTERM_BP_ALL | Organelle organization and biogenesis | 5 | 7.40E−01 | 1.00E+00 |

Table output from DAVID/National Institutes of Health program of the genes that are significantly associated with patient survival, representing top functional category of the upregulated genes, and the top two functional categories of the down-regulated genes.

Table 10 shows estimates of survival for groups based on TIL index, CD3 cell count, MI, and TNM stage (N_38)

| | Group (N) | Median survival (days) and 95% CI |
|---|---|---|
| TIL index (% of cells within the tumor lesion, N = 31*) | 0-25 (12) | 440 (237, NA)** |
| | 25-50 (10) | 1,073 (590, NA) |
| | 50-100 (9) | NA (887, NA) |
| CD3 cell count (cells per 10 HPF, N = 29*) | ≤80 (14) | 653 (440, NA) |
| | >80 (15) | 1,073 (725, NA) |
| Mitotic index (mitoses per HPF, N = 30*) | ≤0.75 (16) | 1,073 (1,073, NA) |
| | >0.75 (14) | 496 (237, NA) |
| TNM Stage (at time of surgery, N = 38) | IIIA (4) | NA |
| | IIIB (18) | 1,073 (725, NA) |
| | IIIC (11) | 780 (440, NA) |
| | IV (5) | 259 (92, NA) |

*Indicates the number of nonmissing values for each measurement.
**NA indicates that the estimate could not be obtained due to small sample size.

Table 11 shows performance of the SVM-based classification algorithm as a function of gene selection and preprocessing methods

| Genes included | Initial gene pool | PCA performed | Sensitivity, % | Specificity, % | Balanced accuracy, % | AUC. % |
|---|---|---|---|---|---|---|
| 10 | All | No | 64.29 | 42.86 | 53.57 | 45.41 |
| 10 | All | Yes | 67.86 | 42.86 | 55.36 | 44.90 |
| 10 | 1.5x | No | 64.29 | 42.86 | 53.57 | 46.68 |
| 10 | 1.5x | Yes | 67.86 | 42.86 | 55.36 | 46.94 |
| 10 | 2x | No | 67.86 | 57.14 | 62.5 | 67.60 |
| 10 | 2x | Yes | 78.57 | 64.29 | 71.43 | 69.64 |
| 30 | All | No | 71.43 | 42.86 | 57.14 | 64.03 |
| 30 | All | Yes | 67.86 | 28.57 | 48.21 | 51.53 |

| Genes included | Initial gene pool | PCA performed | Sensitivity, % | Specificity, % | Balanced accuracy, % | AUC, % |
|---|---|---|---|---|---|---|
| 30 | 1.5x | No | 71.43 | 42.86 | 57.14 | 69.64 |
| 30 | 1.5x | Yes | 60.71 | 35.71 | 48.21 | 57.40 |
| 30 | 2x | No | 71.43 | 64.29 | 67.86 | 70.15 |
| 30 | 2x | Yes | 71.43 | 71.43 | 71.43 | 71.94 |
| 50 | All | No | 71.43 | 42.86 | 57.14 | 68.88 |
| 50 | All | Yes | 67.86 | 35.71 | 51.79 | 60.71 |
| 50 | 1.5x | No | 71.43 | 50 | 60.71 | 71.68 |
| 50 | 1.5x | Yes | 71.43 | 50 | 60.71 | 67.60 |
| 50 | 2x | No | 75.00 | 64.29 | 69.64 | 75.77 |
| 50 | 2x | Yes | 78.57 | 71.43 | 75.00 | 81.38 |
| 100 | All | No | 71.43 | 50.00 | 60.71 | 66.07 |
| 100 | All | Yes | 57.14 | 50.00 | 53.57 | 61.73 |
| 100 | 1.5x | No | 67.86 | 50.00 | 58.93 | 70.92 |
| 100 | 1.5x | Yes | 67.86 | 50.00 | 58.93 | 68.62 |
| 100 | 2x | No | 82.14 | 64.29 | 73.21 | 72.45 |
| 100 | 2x | Yes | 78.57 | 57.14 | 67.86 | 78.32 |
| 300 | All | No | 71.43 | 50.00 | 60.71 | 72.19 |
| 300 | All | Yes | 71.43 | 50.00 | 60.71 | 69.13 |
| 300 | 1.5x | No | 82.14 | 57.14 | 69.64 | 74.74 |
| 300 | 1.5x | Yes | 78.57 | 50.00 | 64.29 | 71.94 |
| 300 | 2x | No | 71.43 | 64.29 | 67.86 | 71.68 |
| 300 | 2x | Yes | 67.86 | 57.14 | 62.5 | 75.00 |
| 500 | All | No | 67.86 | 57.14 | 62.5 | 74.23 |
| 500 | All | Yes | 75.00 | 57.14 | 66.07 | 71.43 |
| 500 | 1.5x | No | 67.86 | 57.14 | 62.5 | 70.92 |
| 500 | 1.5x | Yes | 75.00 | 57.14 | 66.07 | 74.23 |
| 500 | 2x | No | 75.00 | 57.14 | 66.07 | 70.41 |
| 500 | 2x | Yes | 75.00 | 50.00 | 62.5 | 73.98 |
| 1000 | All | No | 71.43 | 57.14 | 64.29 | 68.62 |
| 1000 | All | Yes | 78.57 | 42.86 | 60.71 | 74.74 |
| 1000 | 1.5x | No | 67.86 | 57.14 | 62.50 | 69.90 |
| 1000 | 1.5x | Yes | 75.00 | 50.00 | 62.50 | 71.43 |
| 1000 | 2x | No | 78.57 | 64.29 | 71.43 | 70.92 |
| 1000 | 2x | Yes | 75.00 | 50.00 | 62.5 | 68.37 |

We varied the number of genes selected (10-1000), fold change thresholds (none, 1.5-and 2-fold difference) and whether principal component analysis (PCA) was used. The reported performance measures are sensitivity, specificity, balanced accuracy, and AUC. The highlighted combination of parameters (expression values of the top 50 genes which had at least 2-fold difference in expression, decorrelated using PCA) had the peak performance.

Table 12A shows clinical characteristics, PV gene expression and stage

| | | Low risk (N = 21) | High risk (N = 23) | Statistical test |
|---|---|---|---|---|
| Sex | Female | 8 (38%) | 8 (35%) | Fisher's P value = 1.00 |
| | Male | 13 (62%) | 15 (65%) | |
| Age at recurrence | | Mean = 61 (SD = 18) | Mean = 66 (SD = 19) | Wilcoxon rank sum P = 0.41 |
| CD3 cell count | <80 | 9 (56%) | 7 (47%) | Fisher's P value = 0.72 |
| | ≥80 | 7 (44%) | 8 (53%) | |
| | Missing | 5 | 8 | |
| Mitotic index | <0.75 | 7 (44%) | 9 (56%) | Fisher's P value = 0.72 |
| | ≥0.75 | 9 (56%) | 7 (44%) | |
| | Missing | 5 | 7 | |
| TILs index | 0-25% | 7 (41%) | 7 (44%) | Fisher's P value = 0.01 |
| | 25-50% | 2 (12%) | 8 (50%) | |
| | 50-100% | 8 (27%) | 1 (6%) | |
| | Missing | 4 | 7 | |
| Stage at recurrence/metastasis | IIIA | 2 (9.5%) | 2 (9%) | Fisher's P value = 0.67 |
| | IIIB | 12 (57%) | 11 (48%) | |
| | IIIC | 6 (28.5%) | 6 (26%) | |
| | IV | 1 (5%) | 4 (17%) | |
| Radiation | Yes | 7 (39%) | 3 (14%) | Fisher's P value = 0.14 |
| | No | 11 (61%) | 19 (86%) | |
| | Missing | 3 | 1 | |
| Immunotherapy | Yes | 2 (11%) | 3 (14%) | Fisher's P value = 1.00 |
| | No | 16 (89%) | 19 (86%) | |
| | Missing | 3 | 1 | |
| Chemotherapy | Yes | 7 (39%) | 7 (32%) | Fisher's P value = 0.74 |
| | No | 11 (61%) | 15 (68%) | |
| | Missing | 3 | 1 | |

Clinical characteristics of low and high risk groups predicted based on a Cox multivariable regression model of survival since R/M as a dependant variable and the PV and TNM stage as predictors (N = 44).

Table 12B shows clinical characteristics, PV gene expression and MI

| | | Low risk (N = 16) | High risk (N = 16) | Statistical test |
|---|---|---|---|---|
| Sex | Female | 6 (38%) | 6 (38%) | Fisher's P value = 1.00 |
| | Male | 10 (62%) | 10 (62%) | |
| Age at recurrence | | Mean = 65 (SD = 20) | Mean = 59 (SD = 20) | Wilcoxon rank sum P = 0.31 |
| CD3 cell count | <80 | 7 (44%) | 9 (64%) | Fisher's P value = 0.30 |
| | ≥80 | 9 (56%) | 5 (36%) | |
| | Missing | 0 | 2 | |
| Mitotic index | <0.75 | 11 (69%) | 5 (31%) | Fisher's P value = 0.08 |
| | ≥0.75 | 5 (31%) | 11 (69%) | |
| TILs index | 0-25% | 5 (31%) | 9 (56%) | Fisher's P value = 0.06 |
| | 25-50% | 4 (25%) | 6 (38%) | |
| | 50-100% | 7 (44%) | 1 (6%) | |

|  |  | Low risk (N = 16) | High risk (N = 16) | Statistical test |
|---|---|---|---|---|
| Stage at recurrence/metastasis | IIIA | 2 (12.5%) | 0 (0%) | Fisher's P value = 0.09 |
|  | IIIB | 10 (62.5%) | 7 (44%) |  |
|  | IIIC | 4 (25%) | 5 (31%) |  |
|  | IV | 0 (0%) | 4 (25%) |  |
| Radiation | Yes | 4 (27%) | 3 (20%) | Fisher's P value = 1.00 |
|  | No | 11 (73%) | 12 (80%) |  |
|  | Missing | 1 | 1 |  |
| Immunotherapy | Yes | 0 (0%) | 2 (13%) | Fisher's P value = 0.48 |
|  | No | 15 (100%) | 13 (87%) |  |
|  | Missing | 1 | 1 |  |
| Chemotherapy | Yes | 8 (53%) | 4 (27%) | Fisher's P-Value = 0.26 |
|  | No | 7 (47%) | 11 (73%) |  |
|  | Missing | 1 | 1 |  |

Clinical characteristics of low and high risk groups predicted based on a Cox multivariable regression model of survival since R/M as a dependant variable and the PV and MI as predictors (N = 32).

Discussion

A number of studies analyzing human cancers have shown the importance of the immune response in the equilibrium state of primary neoplasia, but the importance of the immune system in keeping metastatic disease in check is less well understood (20-22). In melanoma, these types of studies have been heavily weighted toward stage I and stage II disease (20, 23). One study, however, has shown a correlation between TILs in resected lymph node metastases and patient survival (24). Similarly, studies of metastatic colorectal cancer, ovarian cancer, and follicular lymphoma have all demonstrated a better prognosis linked to the presence of infiltrating immune cells within tumor lesions (21, 22, 25). Only one other study has examined stage III melanoma by gene expression profiling and that study also linked up-regulation of certain genes associated with the immune system (e.g., HLA-E, PILRA, GTPBP2, IGKC) to time to tumor progression (19) and patient survival. However, that study did not directly address the influence of MI, TILs, or gene signatures on the improvement of TNM staging.

Despite these findings, the evaluation of the presence of leukocytes within metastatic lesions as a potentially easy and predictive tool of patient prognosis has not been sufficiently explored. This is possibly due to the conflicting studies that have shown both beneficial and detrimental effects of their presence (20-22). The present inventors show herein that, based on evaluation of TILs, CD3, and mRNA expression levels in the tumor, there is a comprehensive immune response in the tumors of stage III patients who survive for longer periods of time. We find an array of immune parameters among which are chemokines and adhesion molecules like CXCL13, CCL19, CCR7, VCAM1, and AMICA1 whose presence suggests active recruitment of the immune system into tumor sites. Establishing mechanisms underlying immune cell recruitment and activation at the molecular and cellular levels in metastatic lesions could be an important step toward advancement of immunotherapies in melanoma. For example, we detected higher levels of ICOS mRNA levels in the samples of patients who live longer, and the elevation of CD4+ICOS$^{hi}$ IFNγ secreting T cells has been recently documented in the lesions of prostate cancer patients treated with anti-CTLA-4 antibody (26). Importantly, the gene signatures described herein were validated using an independent dataset from a study with a similar patient population that was published independently (19). Our data suggest that the immune response is in fact important in controlling advanced melanoma and indicate that its signature or quantification through TIL and CD3 counts can further subcategorize the staging system of recurrent tumors.

Another often forgotten and clinically underutilized parameter is MI. Its association with worse prognosis in melanoma has been examined (27), but in the current 6th edition of American Joint Committee on Cancer (AJCC) staging system it does not play a role (28), as a majority of the studies pertained to primary lesions. These studies have shown that MI in primary lesions is significantly associated with tumor thickness and ulceration that are the core determinants of the current staging system. However, MI will be included in the 7th edition of the AJCC staging system to address the classification of stage I melanoma (29). In the present study of metastatic lesions, MI was the strongest indicator of patient survival and was the best single factor that improved current staging, significantly improving the separation between stage IIIB and IIIC patients, that we further validated by expanding patient samples with an additional 52 specimens. Our data support the use of MI in staging more advanced melanoma as well, following epidemiologic validation of this finding.

The present inventors postulate that the progression of metastatic melanoma is manifested by the balance of uncontrolled proliferation (MI) and the comprehensive presence of the immune system (TILs, CD3, and the wide array of immune network molecules detected at the mRNA level). Whether the low proliferative capacity in certain patients allows them to develop an immune response or whether the immune system functions to control proliferation is not clear. Data presented herein indicate that metastatic melanoma is biologically diverse and that there is a need to tailor clinical trials toward the molecular and cellular profile of each patient. Potentially, patients with an existent immune presence in the tumor lesions are more prone to further stimulation of T cells to fight the tumor burden. On the other hand, the biggest benefit from chemotherapy may be seen in the patients whose tumors have high mitotic rates. If so, then subcategorizing patients based on metastatic lesion immune cell infiltration and MI before clinical trial recruitment might yield much more profound results than seen to date.

This invention may be embodied in other forms or carried out in other ways without departing from the spirit or essential characteristics thereof. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this Specification, each of which is incorporated herein by reference in its entirety, including those listed below.

REFERENCES

1. Gray-Schopfer V, Wellbrock C, Marais R (2007) Melanoma biology and new targeted therapy. *Nature* 445:851-857.
2. Thompson J F, Scolyer R A, Kefford R F (2005) Cutaneous melanoma. *Lancet* 365:687-701.
3. Fecher L A, Cummings S D, Keefe M J, Alani R M (2007) Toward a molecular classification of melanoma. *J Clin Oncol* 25:1606-1620.
4. Balch C M, Soong S J (2008) Predicting outcomes in metastatic melanoma. *J Clin Oncol* 26:168-169.
5. Golub T R, et al. (1999) Molecular classification of cancer: Class discovery and class prediction by gene expression monitoring. *Science* 286:531-537.
6. Mills K (2008) Gene expression profiling for the diagnosis and prognosis of acute myeloid leukaemia. *Front Biosci* 13:4605-4616.
7. van't Veer L J, Bernards R (2008) Enabling personalized cancer medicine through analysis of gene-expression patterns. *Nature* 452:564-570.
8. Henry N L, Hayes D F (2007) Use of gene-expression profiling to recommend adjuvant chemotherapy for breast cancer. *Oncology (Williston Park)* 21: 1301-1309; discussion 1311, 1314-1319.
9. Nahleh Z A (2008) Molecularly targeted therapy in breast cancer: The new generation. *Recent Pat Anticancer Drug Discov* 3:100-110.
10. Haqq C, et al. (2005) The gene expression signatures of melanoma progression. *Proc Natl Acad Sci USA* 102:6092-6097.
11. Jaeger J, et al. (2007) Gene expression signatures for tumor progression, tumor subtype, and tumor thickness in laser-microdissected melanoma tissues. *Clin Cancer Res* 13:806-815.
12. Tusher V G, Tibshirani R, ChuG (2001) Significance analysis of microarrays applied to the ionizing radiation response. *Proc Natl Acad Sci USA* 98:5116-5121.
13. Benjamini Y, Hochberg Y (1995) Controlling the false discovery rate: A practical and powerful approach to multiple testing. *J R Stat Soc B* 57: 289-300.
14. Mardia K V, Kent J T, Bibby J M (1979) *Multivariate Analysis* (Academic Press, New York).
15. Hofling H, Tibshirani R (2008) A study of pre-validation. *Annals of Applied Statistics* 2:643-664.
16. Tibshirani R J, Efron B (2002) Pre-validation and inference in microarrays. *Stat Appl Genet Mol Biol* 1, Article 1.
17. Brown M P, et al. (2000) Knowledge-based analysis of microarray gene expression data by using support vector machines. *Proc Natl Acad Sci USA* 97:262-267.
18. Furey T S, et al. (2000) Support vector machine classification and validation of cancer tissue samples using microarray expression data. *Bioinformatics* 16:906-914.
19. John T, et al. (2008) Predicting clinical outcome through molecular profiling in stage III melanoma. *Clin Cancer Res* 14:5173-5180.
20. Piras F, et al. (2005) The predictive value of CD8, CD4, CD68, and human leukocyte antigen-D-related cells in the prognosis of cutaneous malignant melanoma with vertical growth phase. *Cancer* 104:1246-1254.
21. Sato E, et al. (2005) Intraepithelial CD8_tumor-infiltrating lymphocytes and a high CD8_/regulatory T cell ratio are associated with favorable prognosis in ovarian cancer. *Proc Natl Acad Sci USA* 102:18538-18543.
22. Galon J, et al. (2006) Type, density, and location of immune cells within human colorectal tumors predict clinical outcome. *Science* 313:1960-1964.
23. Clemente C G, et al. (1996) Prognostic value of tumor infiltrating lymphocytes in the vertical growth phase of primary cutaneous melanoma. *Cancer* 77:1303-1310.
24. Mihm M C, Jr, Clemente C G, CascinelliN (1996) Tumor infiltrating lymphocytes in lymph node melanomametastases: A histopathologic prognostic indicator and an expression of local immune response. *Lab Invest* 74:43-47.
25. Dave S S, et al. (2004) Prediction of survival in follicular lymphoma based on molecular features of tumor-infiltrating immune cells. *N Engl J Med* 351:2159-2169.
26. Chen H, et al. (2009) Anti-CTLA-4 therapy results in higher CD4_ICOShi T cell frequency and IFN-gamma levels in both nonmalignant and malignant prostate tissues. *Proc Natl Acad Sci USA* 106:2729-2734.
27. Attis M G, Vollmer R T (2007) Mitotic rate in melanoma: A reexamination. *Am J Clin Pathol* 127:380-384.
28. Francken, et al. (2004) The prognostic importance of tumor mitotic rate confirmed in 1317 patients with primary cutaneous melanoma and long follow-up. *Ann Surg Oncol* 11:426-433.
29. Balch C M, Gershenwald J E, Soong S-J, Sober A, Kirkwood J (2009) in *Cutaneous Melanoma*, ed Balch C M, Houghton A, Sober A, and Soong S-J (Quality Medical Publishing, St. Louis).
30. Box G E, Cox D R (1964) An analysis of transformations. *J R Stat Soc B* 26:211-246.
31. RDC Team (2008) *R: A Language and Environment for Statistical Computing* (R Foundation for Statistical Computing, Vienna).
32. Pavlidis P, Lewis D P, Noble W S (2002) Exploring gene expression data with class scores. *Pac Symp Biocomput*, 474-485.
33. Irizarry R A, et al. (2003) Exploration, normalization, and summaries of high density oligonucleotide array probe level data. *Biostatistics* 4:249-264.

What is claimed is:

1. A method for treating a mammal with Stage IIIB or Stage IIIC melanoma, said method comprising: a) isolating a melanoma sample from the mammal; b) quantitating a mitotic index for the melanoma sample by examining tissue sections of the melanoma sample using a microscope having high power field capability; c) comparing the mitotic index determined in step b) with a mitotic index median value determined for a plurality of Stage IIIB and Stage IIIC melanoma samples; d) stratifying the mammal into a first sub-category of mammals having melanoma samples with a low mitotic index or a second sub-category of mammals having melanoma samples with a high mitotic index; and e) treating the mammal with a first therapeutic regimen that promotes immune response in the mammal if the mammal is stratified in the first sub-category of mammals and/or treating the mammal with a second therapeutic regimen that inhibits cell proliferation in the mammal if the mammal is stratified in the second sub-category of mammals.

2. The method of claim 1, wherein the low mitotic index is equivalent to less than 0.75 mitoses per high power field and the high mitotic index is equivalent to more than 0.75 mitoses per high power field.

3. The method of claim 2, wherein the high power field equals 0.196 mm$^2$.

4. The method of claim 1, further comprising determining the number of tumor infiltrating leukocytes (TILs) in the melanoma sample, wherein a high number of TILs is correlated with enhanced duration of survival in the mammal.

5. The method of claim 4, wherein the high number of TILs is equivalent to TILs comprising >50% of tumor area in the melanoma sample.

6. The method of claim 4, wherein the high number of TILs is correlated with a positive response to a therapeutic regimen that promotes immune response in the mammal.

7. A method for treating a mammal with Stage IIIB or Stage IIIC melanoma, said method comprising: a) isolating a melanoma sample from the mammal; b) quantitating a mitotic index for the melanoma sample by examining tissue sections of the melanoma sample using a microscope having high power field capability and comparing the mitotic index determined for the melanoma sample to a mitotic index median value determined for a plurality of Stage IIIB and Stage IIIC melanoma samples to stratify the mammal into a first sub-category of mammals having melanoma samples with a low mitotic index equivalent to less than 0.75 mitoses per high power field or a second sub-category of mammals having melanoma samples with a high mitotic index equivalent to more than 0.75 mitoses per high power field; and c) treating the mammal with a first therapeutic regimen that promotes immune response in the mammal if the mammal is stratified in the first sub-category of mammals and/or treating the mammal with a second therapeutic regimen that inhibits cell proliferation in the mammal if the mammal is stratified in the second sub-category of mammals.

8. The method of claim 7, wherein the second therapeutic regimen comprises administration of at least one of chemotherapy, B-Raf specific inhibitors, MEK inhibitors, cytokines, or localized radiation therapy.

9. The method of claim 7, wherein the first therapeutic regimen comprises administration of at least one of immune therapy or biologics.

10. The method of claim 9, wherein the immune therapy comprises at least one of melanoma associated antigens (MAA) with adjuvants, viral vectors expressing MAA, dendritic cell targeted therapies, or adoptive T cell therapy that targets tumor expressed MAA or NY-ESO-1.

11. The method of claim 9, wherein the biologics comprise at least one of interferon-α (IFN-α), interleukin-2 (IL-2), combinations of IFN-α and IL-2, anti-CTLA-4 or anti-PD-1.

12. The method of claim 7, wherein the high power field equals 0.196 mm$^2$.

13. The method of claim 1, wherein the second therapeutic regimen comprises administration of at least one of chemotherapy, B-Raf specific inhibitors, MEK inhibitors, cytokines, or localized radiation therapy.

14. The method of claim 1, wherein the first therapeutic regimen comprises administration of at least one of immune therapy or biologics.

15. The method of claim 14, wherein the immune therapy comprises at least one of melanoma associated antigens (MAA) with adjuvants, viral vectors expressing MAA, dendritic cell targeted therapies, or adoptive T cell therapy that targets tumor expressed MAA or NY-ESO-1.

16. The method of claim 14, wherein the biologics comprise at least one of interferon-α (IFN-α), interleukin-2 (IL-2), combinations of IFN-α and IL-2, anti-CTLA-4 or anti-PD-1.

17. A method for treating a mammal with Stage IIIB or Stage IIIC melanoma, said method comprising: a) isolating a melanoma sample from the mammal; b) quantitating a mitotic index for the melanoma sample by examining tissue sections of the melanoma sample using a microscope having high power field capability and comparing the mitotic index determined for the melanoma sample to a mitotic index median value determined for a plurality of Stage IIIB and Stage IIIC melanoma samples to stratify the mammal into a first sub-category of mammals having melanoma samples with a low mitotic index or a second sub-category of mammals having melanoma samples with a high mitotic index; and c) treating the mammal with a first therapeutic regimen that promotes immune response in the mammal if the mammal is stratified in the first sub-category of mammals and/or treating the mammal with a second therapeutic regimen that inhibits cell proliferation in the mammal if the mammal is stratified in the second sub-category of mammals.

18. The method of claim 17, wherein the low mitotic index is equivalent to less than 0.75 mitoses per high power field and the high mitotic index is equivalent to more than 0.75 mitoses per high power field.

19. The method of claim 17, wherein the high power field equals 0.196 mm$^2$.

20. The method of claim 17, wherein the second therapeutic regimen comprises administration of at least one of chemotherapy, B-Raf specific inhibitors, MEK inhibitors, cytokines, or localized radiation therapy.

21. The method of claim 17, wherein the first therapeutic regimen comprises administration of at least one of immune therapy or biologics.

22. The method of claim 21, wherein the immune therapy comprises at least one of melanoma associated antigens (MAA) with adjuvants, viral vectors expressing MAA, dendritic cell targeted therapies, or adoptive T cell therapy that targets tumor expressed MAA or NY-ESO-1.

23. The method of claim 21, wherein the biologics comprise at least one of interferon-α (IFN-α), interleukin-2 (IL-2), combinations of IFN-α and IL-2, anti-CTLA-4 or anti-PD-1.

* * * * *